US009611515B2

(12) United States Patent
Alvizo et al.

(10) Patent No.: US 9,611,515 B2
(45) Date of Patent: Apr. 4, 2017

(54) PENTOSE FERMENTATION BY A RECOMBINANT MICROORGANISM

(71) Applicant: Codexis, Inc., Redwood City, CA (US)

(72) Inventors: Oscar Alvizo, Fremont, CA (US); Mathew G. Miller, San Carlos, CA (US); Benjamin N. Mijts, San Carlos, CA (US); Galit Meshulam-Simon, Los Altos, CA (US); Robert McDaniel, Palo Alto, CA (US)

(73) Assignee: Codexis, Inc., Redwood City, CA (US)

( * ) Notice: Subject to any disclaimer, the term of this patent is extended or adjusted under 35 U.S.C. 154(b) by 0 days.

(21) Appl. No.: 14/443,580

(22) PCT Filed: Nov. 14, 2013

(86) PCT No.: PCT/US2013/070009
§ 371 (c)(1),
(2) Date: May 18, 2015

(87) PCT Pub. No.: WO2014/081605
PCT Pub. Date: May 30, 2014

(65) Prior Publication Data
US 2015/0337340 A1  Nov. 26, 2015

Related U.S. Application Data

(60) Provisional application No. 61/728,398, filed on Nov. 20, 2012.

(51) Int. Cl.
| | |
|---|---|
| *C12N 1/00* | (2006.01) |
| *C12N 15/00* | (2006.01) |
| *C12P 7/06* | (2006.01) |
| *C12P 5/02* | (2006.01) |
| *C07H 21/04* | (2006.01) |
| *C12N 9/04* | (2006.01) |
| *C12N 9/92* | (2006.01) |
| *C12N 9/12* | (2006.01) |
| *C12P 7/10* | (2006.01) |

(52) U.S. Cl.
CPC .... *C12Y 207/01017* (2013.01); *C12N 9/0006* (2013.01); *C12N 9/1205* (2013.01); *C12N 9/92* (2013.01); *C12P 7/06* (2013.01); *C12P 7/10* (2013.01); *C12Y 101/01009* (2013.01); *C12Y 503/01005* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| | | |
|---|---|---|
| 4,486,553 A | 12/1984 | Wesch |
| 5,605,793 A | 2/1997 | Stemmer |
| 5,789,210 A * | 8/1998 | Ho ..................... C12N 9/0006 435/163 |
| 5,811,238 A | 9/1998 | Stemmer et al. |
| 5,830,721 A | 11/1998 | Stemmer et al. |
| 5,834,252 A | 11/1998 | Stemmer et al. |
| 5,837,458 A | 11/1998 | Minshull et al. |
| 5,928,905 A | 7/1999 | Stemmer et al. |
| 6,096,548 A | 8/2000 | Stemmer |
| 6,117,679 A | 9/2000 | Stemmer |
| 6,132,970 A | 10/2000 | Stemmer |
| 6,165,793 A | 12/2000 | Stemmer |
| 6,180,406 B1 | 1/2001 | Stemmer |
| 6,251,674 B1 | 6/2001 | Tobin et al. |
| 6,277,638 B1 | 8/2001 | Stemmer |
| 6,287,861 B1 | 9/2001 | Stemmer et al. |
| 6,287,862 B1 | 9/2001 | delCardayre et al. |
| 6,291,242 B1 | 9/2001 | Stemmer |
| 6,297,053 B1 | 10/2001 | Stemmer |
| 6,303,344 B1 | 10/2001 | Patten et al. |
| 6,309,883 B1 | 10/2001 | Minshull et al. |
| 6,319,713 B1 | 11/2001 | Patten et al. |
| 6,319,714 B1 | 11/2001 | Crameri et al. |
| 6,323,030 B1 | 11/2001 | Stemmer |
| 6,326,204 B1 | 12/2001 | delCardayre et al. |
| 6,335,160 B1 | 1/2002 | Patten et al. |
| 6,335,198 B1 | 1/2002 | delCardayre et al. |
| 6,344,356 B1 | 2/2002 | Stemmer |
| 6,352,859 B1 | 3/2002 | delCardayre et al. |
| 6,355,484 B1 | 3/2002 | Patten et al. |
| 6,358,740 B1 | 3/2002 | Patten et al. |

(Continued)

FOREIGN PATENT DOCUMENTS

| | | |
|---|---|---|
| EP | 0 137 280 B1 | 3/1992 |
| EP | 0479426 A1 | 4/1992 |

(Continued)

OTHER PUBLICATIONS

Hahn-Hagerdal et al. Metabolic engineering of *Saccharomyces cerevisiae* for Engineering/Biotechnology, vol. 73, p. 53-84, 2001. xylose utilization, Advances in Biochemical.*
Altschul, S.F., et al., "Gapped Blast and PSI-BLAST: a new generation of protein database search programs," Nucleic Acids Res., 25(17):3389-3402 [1997].
Amore, R., et al., "The fermentation of xylose—an analysis of the expression of Bacillus and Actinoplanes xylose isomerase genes in yeast," Appl. Microbiol. Biotechnol., 30:351-357 [1989].
Blaiseau, P-L, et al., "Primary structure of a chitinase-encoding gene (chi1) from the filamentous fungus Aphanocladium album: similarity to bacterial chitinases," Gene, 120:243-248 [1992].
Boel, E., "Two different types of intervening sequences in the glucoamylase gene from Aspergillus niger," EMBO J., 3:1581-85 [1984].
Botstein, D., et al., "Strategies and Applications of in Vitro Mutagenesis," Science, 229(4719):1193-1201 [1985].

(Continued)

Primary Examiner — Iqbal H Chowdhury
(74) Attorney, Agent, or Firm — Codexis, Inc.

(57) ABSTRACT

The present invention provides methods and compositions suitable for use in the isomerization of xylose to xylulose, as well as methods and compositions suitable for use in the conversion of xylose to xylitol and xylulose, including nucleic acid constructs, recombinant fungal host cells, and related materials.

11 Claims, 11 Drawing Sheets

(56) References Cited

U.S. PATENT DOCUMENTS

| | | |
|---|---|---|
| 6,358,742 B1 | 3/2002 | Stemmer |
| 6,365,377 B1 | 4/2002 | Patten et al. |
| 6,365,408 B1 | 4/2002 | Stemmer |
| 6,368,861 B1 | 4/2002 | Crameri et al. |
| 6,372,497 B1 | 4/2002 | Stemmer |
| 6,376,246 B1 | 4/2002 | Crameri et al. |
| 6,379,964 B1 | 4/2002 | del Cardayre et al. |
| 6,387,702 B1 | 5/2002 | Stemmer |
| 6,391,552 B2 | 5/2002 | Stemmer |
| 6,391,640 B1 | 5/2002 | Minshull et al. |
| 6,395,547 B1 | 5/2002 | Stemmer |
| 6,406,855 B1 | 6/2002 | Patten et al. |
| 6,406,910 B1 | 6/2002 | Patten et al. |
| 6,413,745 B1 | 7/2002 | Patten et al. |
| 6,413,774 B1 | 7/2002 | Stemmer |
| 6,420,175 B1 | 7/2002 | Stemmer |
| 6,423,542 B1 | 7/2002 | Crameri et al. |
| 6,426,224 B1 | 7/2002 | Crameri et al. |
| 6,436,675 B1 | 8/2002 | Welch et al. |
| 6,444,468 B1 | 9/2002 | Stemmer et al. |
| 6,455,253 B1 | 9/2002 | Patten et al. |
| 6,479,652 B1 | 11/2002 | Crameri et al. |
| 6,482,647 B1 | 11/2002 | Stemmer |
| 6,489,146 B2 | 12/2002 | Stemmer et al. |
| 6,506,602 B1 | 1/2003 | Stemmer |
| 6,506,603 B1 | 1/2003 | Stemmer |
| 6,519,065 B1 | 2/2003 | Colbourne et al. |
| 6,521,453 B1 | 2/2003 | Crameri et al. |
| 6,528,311 B1 | 3/2003 | delCardayre et al. |
| 6,573,098 B1 | 6/2003 | Stemmer |
| 6,576,467 B1 | 6/2003 | Stemmer |
| 6,579,678 B1 | 6/2003 | Patten et al. |
| 6,586,182 B1 | 7/2003 | Patten et al. |
| 6,602,986 B1 | 8/2003 | Stemmer et al. |
| 6,613,514 B2 | 9/2003 | Patten et al. |
| 6,653,072 B1 | 11/2003 | Patten et al. |
| 6,716,631 B1 | 4/2004 | delCardayre et al. |
| 6,946,296 B2 | 9/2005 | Patten et al. |
| 6,961,664 B2 | 11/2005 | Selifonov et al. |
| 6,995,017 B1 | 2/2006 | Stemmer |
| 7,024,312 B1 | 4/2006 | Selifonov et al. |
| 7,058,515 B1 | 6/2006 | Selifonov et al. |
| 7,105,297 B2 | 9/2006 | Minshull et al. |
| 7,148,054 B2 | 12/2006 | delCardayre et al. |
| 7,288,375 B2 | 10/2007 | Stemmer et al. |
| 7,421,347 B2 | 9/2008 | Selifonov et al. |
| 7,430,477 B2 | 9/2008 | Selifonov et al. |
| 7,534,564 B2 | 5/2009 | Patten et al. |
| 7,620,500 B2 | 11/2009 | Mundorff et al. |
| 7,620,502 B2 | 11/2009 | Selifonov et al. |
| 7,629,170 B2 | 12/2009 | delCardayre et al. |
| 7,702,464 B1 | 4/2010 | Emig et al. |
| 7,747,391 B2 | 6/2010 | Gustafsson et al. |
| 7,747,393 B2 | 6/2010 | Fox |
| 7,751,986 B2 | 7/2010 | Gustafsson et al. |
| 7,776,598 B2 | 8/2010 | Patten et al. |
| 7,783,428 B2 | 8/2010 | Gustafsson et al. |
| 7,795,030 B2 | 9/2010 | Minshull et al. |
| 7,853,410 B2 | 12/2010 | Selifonov et al. |
| 7,868,138 B2 | 1/2011 | Stemmer et al. |
| 7,873,499 B2 | 1/2011 | Selifonov et al. |
| 7,904,249 B2 | 3/2011 | Selifonov et al. |
| 7,957,912 B2 | 6/2011 | Selifonov et al. |
| 8,143,050 B2 | 3/2012 | Yang et al. |
| 2008/0057541 A1 | 3/2008 | Hill et al. |
| 2008/0220990 A1 | 9/2008 | Fox |
| 2009/0061484 A1 | 3/2009 | Scott et al. |
| 2009/0209009 A1 | 8/2009 | Tolan et al. |
| 2009/0312196 A1 | 12/2009 | Colbeck et al. |
| 2011/0081698 A1* | 4/2011 | Noda ............... C12N 15/81 435/165 |
| 2012/0003703 A1 | 1/2012 | Mitchell et al. |
| 2012/0045793 A1 | 2/2012 | Shock et al. |
| 2012/0077216 A1 | 3/2012 | Zhang et al. |
| 2012/0083019 A1 | 4/2012 | Baidyaroy et al. |
| 2012/0088271 A1 | 4/2012 | Haerizadeh et al. |
| 2012/0107881 A1 | 5/2012 | Dhawan et al. |

FOREIGN PATENT DOCUMENTS

| | | |
|---|---|---|
| WO | 93/03159 A1 | 2/1993 |
| WO | 95/22625 A1 | 8/1995 |
| WO | 96/00787 A1 | 1/1996 |
| WO | 97/00078 A1 | 1/1997 |
| WO | 97/35966 A1 | 10/1997 |
| WO | 98/27230 A1 | 6/1998 |
| WO | 98/31837 A1 | 7/1998 |
| WO | 00/04190 A1 | 1/2000 |
| WO | 00/42651 A1 | 7/2000 |
| WO | 01/75767 A2 | 10/2001 |
| WO | 2007/136762 A2 | 11/2007 |
| WO | 2009/152336 A1 | 12/2009 |
| WO | 2010/070549 A1 | 6/2010 |
| WO | 2010/148148 A2 | 12/2010 |
| WO | 2011/041594 A1 | 4/2011 |
| WO | 2011/066457 A2 | 6/2011 |
| WO | 2011/143632 A2 | 11/2011 |
| WO | 2011/150318 A1 | 12/2011 |
| WO | 2012/024662 A2 | 2/2012 |
| WO | 2012/024698 A1 | 2/2012 |
| WO | 2012/027282 A2 | 3/2012 |
| WO | 2012/044868 A1 | 4/2012 |
| WO | 2012/061432 A1 | 5/2012 |

OTHER PUBLICATIONS

Brat, D., et al., "Functional Expression of a Bacterial Xylose Isomerase in *Saccharomyces cerevisiae*," Appl. Environ. Microbiol. 75(8):2304-2311 [Feb. 13, 2009].

Brigham, J.S., et al., "Hemicellulases: Diversity and Applications," in Handbook on Bioethanol (C. Wyman ed.) pp. 119-141, Taylor and Francis, Washington DC, (1995).

Carter, P., "Site-directed mutagenesis," Biochem. J., 237:1-7 [1986].

Case, M.E, et al., "Efficient transformation of Neurospora crassa by utilizing hybrid plasmid DNA," Proc. Natl. Acad. Sci. USA, 76(10):5259-5263 [1979].

Christians, F.C., et al., "Directed evolution of thymidine kinase for AZT phosphorylation using DNA family shuffling, " Nat. Biotechnol., 17:259-264 [1999].

Crameri A., et al., "DNA shuffling of a family of genes from diverse species accelerates directed evolution," Nature 391:288-291 [1998].

Crameri, A., et al., "Improved green fluorescent protein by molecular evolution using DNA shuffling," Nat. Biotechnol., 14:315-319 [1996].

Crameri A., et al., "Molecular evolution of an arsenate detoxification pathway by DNA shuffling," Nat. Biotechnol., 15:436-438 [1997].

Dale, S.J. et al., "Oligonucleotide-Directed Random Mutagenesis Using the Phosphorothioate Method," Meth. Mol. Biol., 57:369-74 [1996].

Dayhoff, M.O. et al., in Atlas of Protein Sequence and Structure, "A model of evolutionary change in proteins," vol. 5, Suppl. 3, Natl. Biomed. Res. Round, Washington D.C. [1978], pp. 345-352.

Foreman, P.K., et al., "Transcriptional Regulation of Biomass-degrading Enzymes in the Filamentous Fungus Trichoderma reesei," J. Biol. Chem., 278(34):31988-31997 (2003).

Gardonyi, M., et al., "The *Streptomyces rubiginosus* xylose isomerase is misfolded when expressed in *Saccharomyces cerevisiae*," Enzyme Microb. Technol., 32:252-259 [2003].

Glenn, J.K., et al., "Mn(II) Oxidation Is the Principal Function of the Extracellular Mn-Peroxidase from Phanerochaete chrysosporium'," Arch. Biochem. Biophys., 251(2):688-696 [1986].

Harvey, P.J., et al., "Veratryl alcohol as a mediator and the role of radical cations in lignin biodegradation by Phanerochaete chrysosporium," FEBS Lett., 195(1,2):242-246 [1986].

Henaut and Danchin in Neidhardt et al. [eds.], *Escherichia coli* and *Salmonella*, "Analysis and predictions from *Escherichia coli* Sequences, or *E. coli* in silico," ASM Press, Washington D.C., [1987], pp. 2047-2066.

(56) References Cited

OTHER PUBLICATIONS

Henikoff, S., et al., "Amino acid substitution matrices from protein blocks," Proc. Natl. Acad. Sci. USA, 89:10915-10919 [1992].
Henriksen, A.L.S.*, et al., "Study of the glucoamylase promoter in Aspergillllus niger using green fluorescent protein," Microbiol., 145:729-34 [1999].
Hjersted, J.L., et al., "Genome-Scale Analysis of *Saccharomyces cerevisiae* Metabolism and Ethanol Productionin Fed-Batch Culture," Biotechnol. Bioengineer., 97(5):1190-1204 [2007].
Johnstone, I.L., et al., "Cloning an Aspergillus nidulans developmental gene by transformation," EMBO J.,4 (5):1307-1311 [1985].
Kelly, J.M., et al., "Transformation of Asoergillus niger by the amdS gene of Aspergillus nidulans," EMBO J., 4 (2):475-479 [1985].
Kent, W.J., "BLAT—The BLAST-Like Alignment Tool," Genome Res., 12:656-664 [2002].
Kinsey, J.A., et al., "Transformation of Neurospora crassa with the Cloned am (Glutamate Dehydrogenase) Gene," Mol. Cell. Biol., 4:117-122 [1984].
Kramer, B., et al., "Different base/base mismatches are corrected with different efficiencies by the methyl-directed DNA mismatch-repair system of *E. coli*," Cell, 38:879-887 [1984].
Kuyper, M., et al., "High-level functional expression of a fungal xylose isomerase: the key to e/cient ethanolic fermentation of xylose by *Saccharomyces cerevisiae*?," FEMS Yeast Res., 4:69-78 [2003].
Kuyper, M., et al., "Metabolic engineering of a xylose-isomerase-expressing *Saccharomyces cerevisiae* strain for rapid anaerobic xylose fermentation," FEMS Yeast Res., A445:399-409 [2005].
Limon, C., et al., "Primary structure and expression pattern of the 33-kDa chitinase gene from the nucoparasitic fungus Trichocherma harzianum," Curr. Genet., 28:478-83 [1995].
Ling, M.M., et al., "Approaches to Dna Mutagenesis: An Overview," Anal. Biochem., 254(2):157-78 [1997].
Madhaven, A., et al., "Alcoholic fermentation of xylose and mixed sugars using recombinant *Saccharomyces cerevisiae* engineered for xylose utilization," Appl. Microbiol. Biotechnol., 82:1067-1078 [2009].
Manivasakam, P., et al., "Nonhomologous End Joining during Restriction Enzyme-Mediated DNA Integration in *Saccharomyces cerevisiae*," Mol. Cell Biol., 18(3):1736-1745 [1998].A46.
Matsushika, A., et al., "Expression of protein engineered NADP+-dependent xylitol dehydrogenase increases ethanol production from xylose in recombinant *Saccharomyces cerevisiae*," Appl. Microbiol. Biotechnol., 81:243-55 [2008].
Matsushika, A., et al., "Ethanol production from xylose in engineered *Saccharomyces cerevisiae* strains: current state and perspectives," Appl. Microbiol. Biotechnol., 84:37-53 [2009].
McInerney, J.O., "GCUA: general codon usage analysis," Bioformatics, 14(4):372-73 [1998].
Minshull, J., et al., "Protein evolution by molecular breeding," Curr. Op. Chem. Biol., 3:284-290 [1999].
Moes, C.J., et al., "Cloning and Expression of the Clostridium thermosulfurogenes D-Xylose Isomerase Gene (xyk4) in *Saccharomyces cerevisiae*," Biotech. Lett.,18(3):269-274 [1996].
Nakamura, Y., et al., "Codon usage tabulated from international DNA sequence databases: status for the year 2000," Nucl. Acids Res., 28:292 [2000].
Nunberg, J.H., et al., "Molecular Cloning and Characterization of the Glucoamylase Gene of Aspergillus awamori " Mol. Cell Biol., 4(11):2306-2315 [1984].
Park, J.B., et al., "The human glutaredoxin gene: determination of its organization, transcription start point, and promoter analysis," Gene, 197:189-93 [1997].
Romanos, M.A., et al., "Foreign Gene Expression in Yeast: a Review," Yeast 8:423-488 [1992].
Runquist, D., et al., "Comparison of heterologous xylose transporters in recombinant *Saccharomyces cerevisiae* " Biotechnol. Biofuels, 3:5 [2010].

Salheimo, M., et al., "Swollenin, a Trichoderma reesei protein with sequence similarity to the plant expansins, exhibits disruption activity on cellulosic materials," Eur. J. Biochem., 269:4202-4211 [2002].
Sarthy, A. V., et al., "Expression of the *Escherichia coli* Xylose Isomerase Gene in *Saccharomyces cerevisiae*," Appl. Environ. Microbiol., 53(9):1996-2000 [1987].
Sauer, U., "Evolutionary Engineering of Industrially Important Microbial Phenotypes," Adv. Biochem. Engineer. Biotechnol. 73:129-169 [2001].
Sedlak, M., et al., "Characterization of the effectiveness of hexose transporters for transporting xylose during glucoseand xylose co-fermentation by a recombinantSaccharomyces yeast," Yeast 21:671-684 [2004].
Sheir-Neiss, G., et al., "Characterization of the secreted cellulases of Trichoderma reesei wild type and mutants during controlled fermentations," Appl. Microbiol. Biotechnol., 20:46-53 [1984].
Smith, M., "In Vitro Mutagenesis," Ann. Rev. Genet., 19:423-462 [1985].
Sonderegger, M., et al., "Molecular Basis for Anaerobic Growth of *Saccharomyces cerevisiae* on Xylose, Investigated by Global Gene Expression and Metabolic Flux Analysis," Appl. Environ. Microbiol., 70(4):2307-2317 [2004].
Stemmer, W.P.C., "DNA shuffling by random fragmentation and reassembly: In vitro recombination for molecular evolution," Proc. Nat. Acad. Sci. USA, 91:10747-10751 [1994].
Stemmer, W.P.C., "Rapid evolution of a protein in vitro by DNA shuffling," Nature, 370:389-391 [1994].
Stenico, M., et al., "Codon usage in Caenorhabditis elegans: delineation of translational selection and mutational biases," Nucl. Acids Res. 22(13):2437-46 [1994].
Teixiera, M.C., et al., "Genome-Wide Identification of *Saccharomyces cerevisiae* Genes Required for Maximal Tolerance to Ethanol," Appl. Environ. Microbiol., 75(18):5761-5772 [2009].
Tilburn, J., et al., "Transformation by integration in Aspergillus nidulans," Gene 26:205-221 [1983].
Tiwari, S., et al., "Prediction of probable genes by Fourieranalysis of genomic sequences," Comput. Appl. Biosci. 13 (3):263-270 [1997].
Uberbacher, E.C., et al., "Discovering and Understanding Genes in Human DNA Sequence Using Grail," Methods Enzymol., 266:259-281 [1996].
Viikari, L., et al., "Thermostable enzymes in lignocellulose hydrolysis," Adv. Biochem. Eng. Biotechnol., 108:121-45 [2007].
Wada, K., et al., "Codon usage tabulated from the GenBank genetic sequence data," Nucl. Acids Res., 20:2111-2118 [1992].
Walfridsson, M., et al., "Ethanolic Fermentation of Xylose with *Saccharomyces cerevisiae* Harboring the Thermus thermophilus xylA Gene, Which Expresses an Active Xylose (Glucose) Isomerase," Appl. Environ. Microbiol., 62 (12):4648-4651 [1996].
Wells, J.A., et al., "Cassette mutagenesis: an efficient method for generation of multiple mutations at defined sites," Gene, 34:315-323 [1985].
Wenger, J.W., et al.,"Bulk Segregant Analysis by High-Throughput Sequencing Reveals a Novel Xylose Utilization Gene from *Saccharomyces cerevisiae*," PLoS Genet., 6(5):1-17 [2010].
Wisselink, H.W., et al., "Novel Evolutionary Engineering Approach for Accelerated Utilization of Glucose, Xylose, and Arabinose Mixtures by Engineered *Saccharomyces cerevisiae* Strains," Appl. Environ. Microbiol., 75(4):907-914 [2009].
Wright, A., et al., "Diverse Plasmid DNA Vectors by Directed Molecular Evolution of Cytomegalovirus Promoters," Hum. Gene Ther., 16:881-892 [2005].
Wright, F., "The 'effective Number of codons' used in a gene," Gene 87:23-29 [1990].
Yelton, M.M., et al., "Transformation of Aspergillus nidulans by using a trpC plasmid," Proc. Natl. Acad. Sci. USA, 81:1480-1474 [1984].
Zhang, J.-H., et al., "Directed evolution of a fucosidase from a galactosidase by DNA shuffling and screening" Proc. Nat. Acad. Sci. U.S.A., 94:4504-4509 [1997].
Zhu, T., et al., "Construction of two Gateway vectors for gene expression in fungi," Plasmid 62:128-33 [2009].

(56) References Cited

OTHER PUBLICATIONS

UniProtKB/TrEMBL A9KN98_CLOPH dated Feb. 5, 2008.
UniProtKB/TrEMBL B7SLY1_9FUNG dated Feb. 10, 2009.
UniProtKB/TrEMBL D0NA42_PHYIT dated Dec. 15, 2009.
UniProtKB/TrEMBL D8MBL6_BLAHO dated Oct. 5, 2010.
UniProtKB/TrEMBL D9ZEF8_97777 dated Oct. 5, 2010.
UniProtKB/TrEMBL E5G6H4_PICSP dated Feb. 8, 2011.
UniProtKB/TrEMBL G1BER6_9ZZZ dated Oct. 19, 2011.
UniProtKB/TrEMBL I1VX39_CANBO dated Jul. 11,2012.
UniProtKB/TrEMBL I1VX40_CANBO dated Jul. 11, 2012.
UniProtKB/TrEMBL XKS1_YEAST dated Oct. 1, 1996.

* cited by examiner

SEQUENCE LISTING

```
<160> NUMBER OF SEQ ID NOS: 24

<210> SEQ ID NO 1
<211> LENGTH: 1326
<212> TYPE: DNA
<213> ORGANISM: Artificial Sequence
<220> FEATURE:
<223> OTHER INFORMATION: Synthetic polynucleotide

<400> SEQUENCE: 1
atgaagaact atttccccaa cgtcccagaa attaaatacg aaggtccaaa ctccacaaat       60
cctttcgctt ttaaatatta tgatgctaat aaagtagtcg ccggtaagac catgaaggag      120
catttgagat tcgctctatc ctggtggcac actttgtgtg ccggtggtgc tgatccattc      180
ggagtaacta ctatggacag gacctacggt aacattaccg acccaatgga actagctaag      240
gccaaagttg atgctggttt cgaactgatg actaagctgg gcatcgagtt cttctgcttc      300
catgatgccg acattgctcc agaaggtgac accttcgaag agtccaagaa aaatctgttc      360
gagattgttg attacatcaa ggagaagatg gaccaaaccg gcatcaagtt gttatggggc      420
actgctaaca actttagtca ccccaggttc atgcacggtg caggaacttc tcctagtgcc      480
gatgttttcg cttatgctgc tgcgaaaata aagaacgctt tagatgcgac catcaagttg      540
ggcggtagag gttatgtctt ttggggtggt agagaaggtt acgagaccct gctgaatact      600
aacatgggct tagaactgga caacatggct aggttgatga agatggccgt tgagtatggt      660
aggtctattg gattcaaagg tgacttctac atcgagccta aacccaagga acctatgaag      720
caccagtacg acttcgacac tgctaccgta ttaggttttt taaggcagta cgggttggat      780
aaagacttca aattgaacat cgaagccaat cacgccacac tagcaggaca ctcattccag      840
catgagttac gtattgctag tattaacggt atgttgggtt ctgttgatgc taaccaaggt      900
gacgtattgt taggatggga cacggatcaa ttccccacaa acatttatga tactactatg      960
tgtatgtatg aggtcattaa agccggtggt ttcacaaatg gcggcctgaa ctttgatgct     1020
aaagctagaa gaggttcatt cacgcctgaa gatattttct attcttacat tgctggtatg     1080
gatgctttcg cgttagggtt tagagcagct cttaaattga ttgaagacgg tagaattgac     1140
aagtttgtgg ctgacaggta tgcctcttgg aataccggta ttggtgcaga tattattgcc     1200
ggaaaagccg attttgcatc attggaaaaa tatgctttgg agaaaggaga ggttaccgcg     1260
tcattgtctt ctggtagaca agagatgctg gaatctattg tcaacaacgt attgtttagt     1320
ttgtaa                                                                1326
```

<210> SEQ ID NO 2
<211> LENGTH: 441
<212> TYPE: PRT
<213> ORGANISM: Artificial Sequence
<220> FEATURE:
<223> OTHER INFORMATION: Synthetic polypeptide

<400> SEQUENCE: 2

```
Met Lys Asn Tyr Phe Pro Asn Val Pro Glu Ile Lys Tyr Glu Gly Pro
1               5                   10                  15

Asn Ser Thr Asn Pro Phe Ala Phe Lys Tyr Tyr Asp Ala Asn Lys Val
            20                  25                  30

Val Ala Gly Lys Thr Met Lys Glu His Leu Arg Phe Ala Leu Ser Trp
        35                  40                  45

Trp His Thr Leu Cys Ala Gly Gly Ala Asp Pro Phe Gly Val Thr Thr
50                  55                  60

Met Asp Arg Thr Tyr Gly Asn Ile Thr Asp Pro Met Glu Leu Ala Lys
65                  70                  75                  80

Ala Lys Val Asp Ala Gly Phe Glu Leu Met Thr Lys Leu Gly Ile Glu
                85                  90                  95

Phe Phe Cys Phe His Asp Ala Asp Ile Ala Pro Glu Gly Asp Thr Phe
            100                 105                 110

Glu Glu Ser Lys Lys Asn Leu Phe Glu Ile Val Asp Tyr Ile Lys Glu
        115                 120                 125

Lys Met Asp Gln Thr Gly Ile Lys Leu Leu Trp Gly Thr Ala Asn Asn
130                 135                 140

Phe Ser His Pro Arg Phe Met His Gly Ala Gly Thr Ser Pro Ser Ala
145                 150                 155                 160

Asp Val Phe Ala Tyr Ala Ala Ala Lys Ile Lys Asn Ala Leu Asp Ala
                165                 170                 175

Thr Ile Lys Leu Gly Gly Arg Gly Tyr Val Phe Trp Gly Gly Arg Glu
            180                 185                 190

Gly Tyr Glu Thr Leu Leu Asn Thr Asn Met Gly Leu Glu Leu Asp Asn
        195                 200                 205

Met Ala Arg Leu Met Lys Met Ala Val Glu Tyr Gly Arg Ser Ile Gly
210                 215                 220

Phe Lys Gly Asp Phe Tyr Ile Glu Pro Lys Pro Lys Glu Pro Met Lys
225                 230                 235                 240

His Gln Tyr Asp Phe Asp Thr Ala Thr Val Leu Gly Phe Leu Arg Gln
                245                 250                 255

Tyr Gly Leu Asp Lys Asp Phe Lys Leu Asn Ile Glu Ala Asn His Ala
            260                 265                 270

Thr Leu Ala Gly His Ser Phe Gln His Glu Leu Arg Ile Ala Ser Ile
        275                 280                 285

Asn Gly Met Leu Gly Ser Val Asp Ala Asn Gln Gly Asp Val Leu Leu
290                 295                 300

Gly Trp Asp Thr Asp Gln Phe Pro Thr Asn Ile Tyr Asp Thr Thr Met
305                 310                 315                 320

Cys Met Tyr Glu Val Ile Lys Ala Gly Gly Phe Thr Asn Gly Gly Leu
                325                 330                 335

Asn Phe Asp Ala Lys Ala Arg Arg Gly Ser Phe Thr Pro Glu Asp Ile
            340                 345                 350

Phe Tyr Ser Tyr Ile Ala Gly Met Asp Ala Phe Ala Leu Gly Phe Arg
        355                 360                 365

Ala Ala Leu Lys Leu Ile Glu Asp Gly Arg Ile Asp Lys Phe Val Ala
```

```
                370               375                380
Asp Arg Tyr Ala Ser Trp Asn Thr Gly Ile Gly Ala Asp Ile Ile Ala
385                 390                 395                 400

Gly Lys Ala Asp Phe Ala Ser Leu Glu Lys Tyr Ala Leu Glu Lys Gly
                405                 410                 415

Glu Val Thr Ala Ser Leu Ser Ser Gly Arg Gln Glu Met Leu Glu Ser
            420                 425                 430

Ile Val Asn Asn Val Leu Phe Ser Leu
            435                 440
```

<210> SEQ ID NO 3
<211> LENGTH: 1092
<212> TYPE: DNA
<213> ORGANISM: Artificial Sequence
<220> FEATURE:
<223> OTHER INFORMATION: Synthetic polynucleotide

<400> SEQUENCE: 3

| | | |
|---|---|---|
| atgaccgcta atccctctct tgttttgaat aagattgacg acatttcttt tgaaacttac | 60 |
| gatgctcccg aaattagcga acccacagac gttttagttc aagttaaaaa aactggtatc | 120 |
| tgcggttctg acatccactt ctacgctcat ggaaggatcg caacttcgt cttaacaaag | 180 |
| ccaatggttc tgggtcatga agcgcgggt actgttgttc aagtcggtaa aggtgttact | 240 |
| tcactgaagg ttggtgataa cgtcgcaatc gagcccggta ttccatctag gttcagtgat | 300 |
| gagtacaaat ctggtcacta aacctgtgt ccacacatgg catttgctgc tactcccaat | 360 |
| tctaaagagg gtgaaccaaa cccaccagga actctatgta agtacttcaa atctccagaa | 420 |
| gacttcctgg ttaagttacc cgatcatgtt tctttggagt tgggtgcttt ggtcgagcca | 480 |
| ctatctgttg ggtccatgc tagtaaatta ggctccgttg catttggcga ttacgttgct | 540 |
| gtttttggtg ctggtccagt aggattactg gctgccgctg tcgctaagac atttggtgcc | 600 |
| aagggtgtga ttgtcgttga tatatttgac aacaagctga agatggccaa agacataggt | 660 |
| gccgctacac ataccttcaa ctccaagacg ggaggtagtg aagaattgat caaagccttc | 720 |
| ggtggtaatg taccaaatgt tgtcttggaa tgtactgggg ctgaaccatg tattaagcta | 780 |
| ggtgttgatg ccatcgcacc aggtggtaga ttcgtgcaag ttggtaatgc tgctggtccc | 840 |
| gtgtcctttc ccataacagt gttcgctatg aaagaactta ctttgtttgg ttcatttcgt | 900 |
| tatggtttca cgactataa gacagccgtg ggtatctttg atactaacta ccagaacggt | 960 |
| agagagaatg ctcccattga ctttgaacag cttatcacgc acagatacaa attcaaagac | 1020 |
| gccattgaag cctacgacct agtaagagca ggtaaagggg ctgtcaagtg tttgattgat | 1080 |
| ggtccagaat aa | 1092 |

<210> SEQ ID NO 4
<211> LENGTH: 363
<212> TYPE: PRT
<213> ORGANISM: Artificial Sequence
<220> FEATURE:
<223> OTHER INFORMATION: Syntheitc polypeptide

<400> SEQUENCE: 4

```
Met Thr Ala Asn Pro Ser Leu Val Leu Asn Lys Ile Asp Asp Ile Ser
1               5                   10                  15

Phe Glu Thr Tyr Asp Ala Pro Glu Ile Ser Glu Pro Thr Asp Val Leu
            20                  25                  30

Val Gln Val Lys Lys Thr Gly Ile Cys Gly Ser Asp Ile His Phe Tyr
```

```
                        35                  40                  45
Ala His Gly Arg Ile Gly Asn Phe Val Leu Thr Lys Pro Met Val Leu
 50                  55                  60

Gly His Glu Ser Ala Gly Thr Val Val Gln Val Gly Lys Gly Val Thr
 65                  70                  75                  80

Ser Leu Lys Val Gly Asp Asn Val Ala Ile Glu Pro Gly Ile Pro Ser
                 85                  90                  95

Arg Phe Ser Asp Glu Tyr Lys Ser Gly His Tyr Asn Leu Cys Pro His
            100                 105                 110

Met Ala Phe Ala Ala Thr Pro Asn Ser Lys Glu Gly Glu Pro Asn Pro
        115                 120                 125

Pro Gly Thr Leu Cys Lys Tyr Phe Lys Ser Pro Glu Asp Phe Leu Val
    130                 135                 140

Lys Leu Pro Asp His Val Ser Leu Glu Leu Gly Ala Leu Val Glu Pro
145                 150                 155                 160

Leu Ser Val Gly Val His Ala Ser Lys Leu Gly Ser Val Ala Phe Gly
                165                 170                 175

Asp Tyr Val Ala Val Phe Gly Ala Gly Pro Val Gly Leu Leu Ala Ala
            180                 185                 190

Ala Val Ala Lys Thr Phe Gly Ala Lys Gly Val Ile Val Val Asp Ile
        195                 200                 205

Phe Asp Asn Lys Leu Lys Met Ala Lys Asp Ile Gly Ala Ala Thr His
    210                 215                 220

Thr Phe Asn Ser Lys Thr Gly Gly Ser Glu Glu Leu Ile Lys Ala Phe
225                 230                 235                 240

Gly Gly Asn Val Pro Asn Val Val Leu Glu Cys Thr Gly Ala Glu Pro
                245                 250                 255

Cys Ile Lys Leu Gly Val Asp Ala Ile Ala Pro Gly Gly Arg Phe Val
            260                 265                 270

Gln Val Gly Asn Ala Ala Gly Pro Val Ser Phe Pro Ile Thr Val Phe
        275                 280                 285

Ala Met Lys Glu Leu Thr Leu Phe Gly Ser Phe Arg Tyr Gly Phe Asn
    290                 295                 300

Asp Tyr Lys Thr Ala Val Gly Ile Phe Asp Thr Asn Tyr Gln Asn Gly
305                 310                 315                 320

Arg Glu Asn Ala Pro Ile Asp Phe Glu Gln Leu Ile Thr His Arg Tyr
                325                 330                 335

Lys Phe Lys Asp Ala Ile Glu Ala Tyr Asp Leu Val Arg Ala Gly Lys
            340                 345                 350

Gly Ala Val Lys Cys Leu Ile Asp Gly Pro Glu
        355                 360

<210> SEQ ID NO 5
<211> LENGTH: 1803
<212> TYPE: DNA
<213> ORGANISM: Artificial Sequence
<220> FEATURE:
<223> OTHER INFORMATION: Synthetic polynucleotide

<400> SEQUENCE: 5
atgctgtgct ccgttataca aaggcaaaca agagaagtat ccaacactat gtctttagat      60
agttattatc taggattcga tttaagtaca caacaattga aatgtcttgc tataaaccag     120
gatctaaaga tcgtccattc cgaaactgtc gagttcgaga aggacttacc acattatcac     180
accaagaaag gcgtctacat tcatggtgac accatcgaat gcccagttgc tatgtggtta     240
```

```
gaagccctgg atcttgtcct gtccaaatat agggaggcaa agttcccact gaacaaggtc      300
atggctgttt ccggttcttg tcagcagcat ggctccgtct actggtcatc acaggctgaa      360
tctctgttag aacaactgaa caagaagcca gagaaggacc tgttacacta cgtctcctct      420
gttgcatttg ccagacaaac tgctcctaat tggcaagacc attccactgc taaacaatgt      480
caggagttcg aagagtgtat tggtggacca gagaaaatgg cccagttaac tggttcccgt      540
gctcatttca ggttcacagg cccacaaatc ctgaagattg ctcagttaga accagaggct      600
tatgaaaaga ctaagaccat ctctttggtc tctaatttct taacttccat tctggttggt      660
cacttggtcg aactggaaga agctgatgcg tgtggtatga acctgtacga catccgtgag      720
aggaagttct ctgacgaact gctgcatctt atcgactcct cctctaagga caagaccatc      780
aggcagaaac tgatgagggc accaatgaag aacctgattg ccggtactat ttgcaagtac      840
ttcatcgaaa agtatggctt caacaccaac tgcaaagtct cccctatgac tggcgataac      900
ctagccacca tttgtagctt gcccttaaga aaaaacgatg ttcttgtgtc tttgggtact      960
tccacaaccg tcttgttggt taccgacaaa tatcacccctt caccaaacta ccacctgttc     1020
atccacccga cgttgcctaa ccactacatg ggcatgatct gctactgcaa tggcagtttta    1080 gcaagggaaa ggataaggga cgagttgaac aaggagaggg agaacaacta cgagaagacc     1140
aacgattgga ccctgttcaa ccaagctgtc ctggatgata cgaatcctc cgagaatgaa      1200 ctgggcgttt actttccact aggcgagatc gttccatctg tcaaggccat caacaagaga     1260
gtaatcttca accccaagac tggcatgatc gaaagggaag tcgccaagtt caaggacaag     1320
agacatgacg ccaagaacat cgttgaatct caagccttat cttgccgtgt taggatttct     1380
cccctactaa gcgactccaa tgcttcttcc cagcaacgtt tgaacgagga tacgattgtt     1440
aaattcgact acgacgagag tccattgaga gactacttga acaaacgtcc tgagaggaca     1500
ttctttgttg gtggcgcatc caagaacgat gctattgtta agaagtttgc tcaggtcata     1560
ggagcaacca aaggtaactt tcgtttagaa actccaaact catgcgcttt aggtggttgc     1620
tacaaggcta tgtggtcttt gttgtatgat agcaataaaa tcgctgttcc tttcgacaag     1680
ttcctaaacg ataacttccc ttggcacgtc atggaatcca tcagcgatgt agacaacgag     1740
aattgggata gatacaattc taaaatagtt cccttgtctg agttagagaa gaccttgatt     1800
taa                                                                   1803
```

<210> SEQ ID NO 6
<211> LENGTH: 600
<212> TYPE: PRT
<213> ORGANISM: Artificial Sequence
<220> FEATURE:
<223> OTHER INFORMATION: Synthetic polypeptide

<400> SEQUENCE: 6

```
Met Leu Cys Ser Val Ile Gln Arg Gln Thr Arg Glu Val Ser Asn Thr
1               5                   10                  15

Met Ser Leu Asp Ser Tyr Tyr Leu Gly Phe Asp Leu Ser Thr Gln Gln
                20                  25                  30

Leu Lys Cys Leu Ala Ile Asn Gln Asp Leu Lys Ile Val His Ser Glu
            35                  40                  45

Thr Val Glu Phe Glu Lys Asp Leu Pro His Tyr His Thr Lys Lys Gly
        50                  55                  60

Val Tyr Ile His Gly Asp Thr Ile Glu Cys Pro Val Ala Met Trp Leu
65                  70                  75                  80
```

```
Glu Ala Leu Asp Leu Val Leu Ser Lys Tyr Arg Glu Ala Lys Phe Pro
                85                  90                  95
Leu Asn Lys Val Met Ala Val Ser Gly Ser Cys Gln Gln His Gly Ser
            100                 105                 110
Val Tyr Trp Ser Ser Gln Ala Glu Ser Leu Leu Glu Gln Leu Asn Lys
        115                 120                 125
Lys Pro Glu Lys Asp Leu Leu His Tyr Val Ser Ser Val Ala Phe Ala
    130                 135                 140
Arg Gln Thr Ala Pro Asn Trp Gln Asp His Ser Thr Ala Lys Gln Cys
145                 150                 155                 160
Gln Glu Phe Glu Glu Cys Ile Gly Gly Pro Glu Lys Met Ala Gln Leu
                165                 170                 175
Thr Gly Ser Arg Ala His Phe Arg Phe Thr Gly Pro Gln Ile Leu Lys
            180                 185                 190
Ile Ala Gln Leu Glu Pro Glu Ala Tyr Glu Lys Thr Lys Thr Ile Ser
        195                 200                 205
Leu Val Ser Asn Phe Leu Thr Ser Ile Leu Val Gly His Leu Val Glu
    210                 215                 220
Leu Glu Glu Ala Asp Ala Cys Gly Met Asn Leu Tyr Asp Ile Arg Glu
225                 230                 235                 240
Arg Lys Phe Ser Asp Glu Leu Leu His Leu Ile Asp Ser Ser Ser Lys
                245                 250                 255
Asp Lys Thr Ile Arg Gln Lys Leu Met Arg Ala Pro Met Lys Asn Leu
            260                 265                 270
Ile Ala Gly Thr Ile Cys Lys Tyr Phe Ile Glu Lys Tyr Gly Phe Asn
        275                 280                 285
Thr Asn Cys Lys Val Ser Pro Met Thr Gly Asp Asn Leu Ala Thr Ile
    290                 295                 300
Cys Ser Leu Pro Leu Arg Lys Asn Asp Val Leu Val Ser Leu Gly Thr
305                 310                 315                 320
Ser Thr Thr Val Leu Leu Val Thr Asp Lys Tyr His Pro Ser Pro Asn
                325                 330                 335
Tyr His Leu Phe Ile His Pro Thr Leu Pro Asn His Tyr Met Gly Met
            340                 345                 350
Ile Cys Tyr Cys Asn Gly Ser Leu Ala Arg Glu Arg Ile Arg Asp Glu
        355                 360                 365
Leu Asn Lys Glu Arg Glu Asn Asn Tyr Glu Lys Thr Asn Asp Trp Thr
    370                 375                 380
Leu Phe Asn Gln Ala Val Leu Asp Asp Ser Glu Ser Ser Glu Asn Glu
385                 390                 395                 400
Leu Gly Val Tyr Phe Pro Leu Gly Glu Ile Val Pro Ser Val Lys Ala
                405                 410                 415
Ile Asn Lys Arg Val Ile Phe Asn Pro Lys Thr Gly Met Ile Glu Arg
            420                 425                 430
Glu Val Ala Lys Phe Lys Asp Lys Arg His Asp Ala Lys Asn Ile Val
        435                 440                 445
Glu Ser Gln Ala Leu Ser Cys Arg Val Arg Ile Ser Pro Leu Leu Ser
    450                 455                 460
Asp Ser Asn Ala Ser Ser Gln Gln Arg Leu Asn Glu Asp Thr Ile Val
465                 470                 475                 480
Lys Phe Asp Tyr Asp Glu Ser Pro Leu Arg Asp Tyr Leu Asn Lys Arg
                485                 490                 495
```

```
Pro Glu Arg Thr Phe Phe Val Gly Gly Ala Ser Lys Asn Asp Ala Ile
            500                 505                 510
Val Lys Lys Phe Ala Gln Val Ile Gly Ala Thr Lys Gly Asn Phe Arg
        515                 520                 525
Leu Glu Thr Pro Asn Ser Cys Ala Leu Gly Gly Cys Tyr Lys Ala Met
    530                 535                 540
Trp Ser Leu Leu Tyr Asp Ser Asn Lys Ile Ala Val Pro Phe Asp Lys
545                 550                 555                 560
Phe Leu Asn Asp Asn Phe Pro Trp His Val Met Glu Ser Ile Ser Asp
                565                 570                 575
Val Asp Asn Glu Asn Trp Asp Arg Tyr Asn Ser Lys Ile Val Pro Leu
            580                 585                 590
Ser Glu Leu Glu Lys Thr Leu Ile
            595                 600

<210> SEQ ID NO 7
<211> LENGTH: 1329
<212> TYPE: DNA
<213> ORGANISM: Artificial Sequence
<220> FEATURE:
<223> OTHER INFORMATION: Synthetic polynucleotide

<400> SEQUENCE: 7
atggatggcg acttagatcc taaagaatat tttcctgaaa ttcctaaaat aaagtatgaa      60
ggacccgaat ctaaaaatcc aatggcgttt cattattatg atgcagaaaa ggtggtgatg     120
ggtaaaaaga tgaaagattg gttaaggttc gcaatgtgtt ggtggcacac actatgtgca     180
gatggcgccg accaatttgg tgctggcact aagacattcc catggaatga aggctcagat     240
ccaatcgcga tagctaaaca aaagtagac gctggttttg aaataatgca aaagctgggg     300
attgaatact actgcttcca cgatgtggat ctagtgtctg aagggaatag cgttgaagag     360
tatgaggcta acttaaagca ggtagttgcc tacttgaaag aaaagcaaca acaaacgggt     420
attaaactgt tgtggtctac cgcgaatgtc ttcggtaata agagatacat gaatggtgct     480
tctacaaacc cggatttcga tgttgtcgct gagcaatag tgcaaataaa aaatgctatg     540
gatgcaggga ttgaattggg agcagaaaat tatgtcttct ggggaggaag agaaggatat     600
atgtctttat tgaatactga ccagaagaga gaaaaagaac acatggctag aatgcttact     660
atggccagag attacgctag aagcaagggt tttaaaggta cgttcttaat cgaacccaaa     720
ccctgcgagc cctctaagca tcagtatgat gtagatacgg aaactgtaat aggcttcctg     780
agggctcaca atctagacaa agatttcaag gtaaatatcg aagtcaacca cgcgacccct     840
gctggacata cttttgaaca cgaacttgcg tgtgcagtag atgcgggtat gttaggtagc     900
atagacgcaa atagaggtga ttatcagaat ggatgggata ccgatcagtt ccctattgac     960
caatacgaat tagtacaagc ttggatggaa attatcaggg gtggcggctt tacaacgggc    1020
gggacaaact tgatgctaa aaccagacgt aattctactg acttagagga tattttttatc    1080
gctcatataa gtggtatgga cgctatggca cgtgctttgg agaatgccgc aaagttactg    1140
gaggaatctc caatccccaa gatgaagaag gaaagatacg cttcattcga ttctggaatg    1200
ggtaaagatt tcgaggatgg taagttaacg ctagagcagg tttatgagta cgggaagaag    1260
aatggtgaac cgaaggatac ttctggaaaa caagaacttt acgaggccat agtagcaatg    1320
tacgcttag                                                           1329

<210> SEQ ID NO 8
```

```
<211> LENGTH: 442
<212> TYPE: PRT
<213> ORGANISM: Artificial Sequence
<220> FEATURE:
<223> OTHER INFORMATION: Synthetic polypeptide

<400> SEQUENCE: 8

Met Asp Gly Asp Leu Asp Pro Lys Glu Tyr Phe Pro Glu Ile Pro Lys
1               5                   10                  15

Ile Lys Tyr Glu Gly Pro Glu Ser Lys Asn Pro Met Ala Phe His Tyr
            20                  25                  30

Tyr Asp Ala Glu Lys Val Val Met Gly Lys Lys Met Lys Asp Trp Leu
        35                  40                  45

Arg Phe Ala Met Cys Trp Trp His Thr Leu Cys Ala Asp Gly Ala Asp
    50                  55                  60

Gln Phe Gly Ala Gly Thr Lys Thr Phe Pro Trp Asn Glu Gly Ser Asp
65                  70                  75                  80

Pro Ile Ala Ile Ala Lys Gln Lys Val Asp Ala Gly Phe Glu Ile Met
                85                  90                  95

Gln Lys Leu Gly Ile Glu Tyr Tyr Cys Phe His Asp Val Asp Leu Val
            100                 105                 110

Ser Glu Gly Asn Ser Val Glu Glu Tyr Glu Ala Asn Leu Lys Gln Val
        115                 120                 125

Val Ala Tyr Leu Lys Glu Lys Gln Gln Gln Thr Gly Ile Lys Leu Leu
    130                 135                 140

Trp Ser Thr Ala Asn Val Phe Gly Asn Lys Arg Tyr Met Asn Gly Ala
145                 150                 155                 160

Ser Thr Asn Pro Asp Phe Asp Val Val Ala Arg Ala Ile Val Gln Ile
                165                 170                 175

Lys Asn Ala Met Asp Ala Gly Ile Glu Leu Gly Ala Glu Asn Tyr Val
            180                 185                 190

Phe Trp Gly Gly Arg Glu Gly Tyr Met Ser Leu Leu Asn Thr Asp Gln
        195                 200                 205

Lys Arg Glu Lys Glu His Met Ala Arg Met Leu Thr Met Ala Arg Asp
    210                 215                 220

Tyr Ala Arg Ser Lys Gly Phe Lys Gly Thr Phe Leu Ile Glu Pro Lys
225                 230                 235                 240

Pro Cys Glu Pro Ser Lys His Gln Tyr Asp Val Asp Thr Glu Thr Val
                245                 250                 255

Ile Gly Phe Leu Arg Ala His Asn Leu Asp Lys Asp Phe Lys Val Asn
            260                 265                 270

Ile Glu Val Asn His Ala Thr Leu Ala Gly His Thr Phe Glu His Glu
        275                 280                 285

Leu Ala Cys Ala Val Asp Ala Gly Met Leu Gly Ser Ile Asp Ala Asn
    290                 295                 300

Arg Gly Asp Tyr Gln Asn Gly Trp Asp Thr Asp Gln Phe Pro Ile Asp
305                 310                 315                 320

Gln Tyr Glu Leu Val Gln Ala Trp Met Glu Ile Ile Arg Gly Gly Gly
                325                 330                 335

Phe Thr Thr Gly Gly Thr Asn Phe Asp Ala Lys Thr Arg Arg Asn Ser
            340                 345                 350

Thr Asp Leu Glu Asp Ile Phe Ile Ala His Ile Ser Gly Met Asp Ala
        355                 360                 365

Met Ala Arg Ala Leu Glu Asn Ala Ala Lys Leu Leu Glu Glu Ser Pro
    370                 375                 380
```

Ile Pro Lys Met Lys Lys Glu Arg Tyr Ala Ser Phe Asp Ser Gly Met
385                 390                 395                 400

Gly Lys Asp Phe Glu Asp Gly Lys Leu Thr Leu Glu Gln Val Tyr Glu
            405                 410                 415

Tyr Gly Lys Lys Asn Gly Glu Pro Lys Asp Thr Ser Gly Lys Gln Glu
        420                 425                 430

Leu Tyr Glu Ala Ile Val Ala Met Tyr Ala
        435                 440

<210> SEQ ID NO 9
<211> LENGTH: 1329
<212> TYPE: DNA
<213> ORGANISM: Artificial Sequence
<220> FEATURE:
<223> OTHER INFORMATION: Synthetic polynucleotide

<400> SEQUENCE: 9

```
atggatggtg atttagatcc aaaagaatat tttccagaaa ttcctaagat taaatatgaa      60
ggtcctgaat ccaaaaatcc aatggctttt cattattatg atgcagaaaa agttgtgatg     120
ggtaaaaaaa tgaaagattg gttaagattc gcaatgtgtt ggtggcacac attatgtgca     180
gatggtgcag accaatttgg tgctggtact aagacttttc catggaatga aggttctgat     240
ccaatcgcta tcgctaaaca aaagttgat gctggttttg aaattatgca aagcttggg       300
attgaatact actgtttcca cgatgtcgat ttagtctctg aaggcaattc cgttgaagaa     360
tatgaagcta acttgaagca ggttgttgca tacttgaaag aaaagcaaca acaaaccggt     420
attaaacttt tgtggtctac agccaatgta ttcggtaata gagatacat gaatggtgct     480
tctacaaacc ctgattttga tgttgttgct agagctattg tccaaattaa aaatgctatg     540
gatgctggca ttgaattggg tgctgaaaat tatgtatttt ggggtggaag agaaggttat     600
atgtctttgt tgaatactga tcaaagaga gaaaaagaac acatggctag aatgctaact     660
atggcaagag attacgctag atccaagggt tttaaggta cttttttgat agaacctaaa     720
ccttgcgagc cttctaaaca tcagtatgat gttgataccg aaactgttat tggttttta      780
agggctcaca atttagacaa agattttaag gttaatatcg aagttaatca cgccacatta    840
gctggtcata cttttgaaca cgaattagcc tgtgctgttg atgccggtat gttgggttcc     900
atagatgcta atagaggtga ttatcaaaat ggttgggata cagatcaatt cccaattgac     960
caatatgaat tggttcaagc ttggatggaa attatcagag gtggaggttt tacaacgggt    1020
gggacaaact tgatgctaa aacaaggaga aattctactg acttagaaga tattttatc     1080
gctcatattt caggtatgga tgctatggct agggctttgg agaatgccgc aaaattactg   1140
gaagaatctc aatacctaa gatgaagaag gaaagatacg cttctttga ttctggtatg    1200
ggtaaagatt tcgaagatgg taagttgacc ttagaacaag tttatgaata cggcaaaaaa   1260
aatggtgaac ctaaggatac ttctggtaaa caagaattat acgaagcaat tgttgctatg  1320
tacgcttag                                                                                   1329
```

<210> SEQ ID NO 10
<211> LENGTH: 442
<212> TYPE: PRT
<213> ORGANISM: Artificial Sequence
<220> FEATURE:
<223> OTHER INFORMATION: Synthetic polypeptide

<400> SEQUENCE: 10

-continued

```
Met Asp Gly Asp Leu Asp Pro Lys Glu Tyr Phe Pro Glu Ile Pro Lys
1               5                   10                  15

Ile Lys Tyr Glu Gly Pro Glu Ser Lys Asn Pro Met Ala Phe His Tyr
            20                  25                  30

Tyr Asp Ala Glu Lys Val Val Met Gly Lys Lys Met Lys Asp Trp Leu
            35                  40                  45

Arg Phe Ala Met Cys Trp Trp His Thr Leu Cys Ala Asp Gly Ala Asp
50                  55                  60

Gln Phe Gly Ala Gly Thr Lys Thr Phe Pro Trp Asn Glu Gly Ser Asp
65                  70                  75                  80

Pro Ile Ala Ile Ala Lys Gln Lys Val Asp Ala Gly Phe Glu Ile Met
                85                  90                  95

Gln Lys Leu Gly Ile Glu Tyr Tyr Cys Phe His Asp Val Asp Leu Val
            100                 105                 110

Ser Glu Gly Asn Ser Val Glu Glu Tyr Glu Ala Asn Leu Lys Gln Val
            115                 120                 125

Val Ala Tyr Leu Lys Glu Lys Gln Gln Gln Thr Gly Ile Lys Leu Leu
            130                 135                 140

Trp Ser Thr Ala Asn Val Phe Gly Asn Lys Arg Tyr Met Asn Gly Ala
145                 150                 155                 160

Ser Thr Asn Pro Asp Phe Asp Val Val Ala Arg Ala Ile Val Gln Ile
                165                 170                 175

Lys Asn Ala Met Asp Ala Gly Ile Glu Leu Gly Ala Glu Asn Tyr Val
            180                 185                 190

Phe Trp Gly Gly Arg Glu Gly Tyr Met Ser Leu Leu Asn Thr Asp Gln
            195                 200                 205

Lys Arg Glu Lys Glu His Met Ala Arg Met Leu Thr Met Ala Arg Asp
210                 215                 220

Tyr Ala Arg Ser Lys Gly Phe Lys Gly Thr Phe Leu Ile Glu Pro Lys
225                 230                 235                 240

Pro Cys Glu Pro Ser Lys His Gln Tyr Asp Val Asp Thr Glu Thr Val
                245                 250                 255

Ile Gly Phe Leu Arg Ala His Asn Leu Asp Lys Asp Phe Lys Val Asn
            260                 265                 270

Ile Glu Val Asn His Ala Thr Leu Ala Gly His Thr Phe Glu His Glu
            275                 280                 285

Leu Ala Cys Ala Val Asp Ala Gly Met Leu Gly Ser Ile Asp Ala Asn
            290                 295                 300

Arg Gly Asp Tyr Gln Asn Gly Trp Asp Thr Asp Gln Phe Pro Ile Asp
305                 310                 315                 320

Gln Tyr Glu Leu Val Gln Ala Trp Met Glu Ile Ile Arg Gly Gly Gly
            325                 330                 335

Phe Thr Thr Gly Gly Thr Asn Phe Asp Ala Lys Thr Arg Arg Asn Ser
            340                 345                 350

Thr Asp Leu Glu Asp Ile Phe Ile Ala His Ile Ser Gly Met Asp Ala
            355                 360                 365

Met Ala Arg Ala Leu Glu Asn Ala Ala Lys Leu Leu Glu Glu Ser Pro
370                 375                 380

Ile Pro Lys Met Lys Lys Glu Arg Tyr Ala Ser Phe Asp Ser Gly Met
385                 390                 395                 400

Gly Lys Asp Phe Glu Asp Gly Lys Leu Thr Leu Glu Gln Val Tyr Glu
            405                 410                 415

Tyr Gly Lys Lys Asn Gly Glu Pro Lys Asp Thr Ser Gly Lys Gln Glu
```

```
                 420                 425                 430
Leu Tyr Glu Ala Ile Val Ala Met Tyr Ala
        435                 440
```

<210> SEQ ID NO 11
<211> LENGTH: 1314
<212> TYPE: DNA
<213> ORGANISM: Artificial Sequence
<220> FEATURE:
<223> OTHER INFORMATION: Synthetic polynucleotide

<400> SEQUENCE: 11

```
atgaccaaag aatacttccc aactataggt aaaattagat tgaaggtaa agatagcaag      60
aatccaatgg catttcacta ctacgatgca gaaaagaag ttatgggcaa aagatgaaa     120
gattggctga ggttcgcaat ggcttggtgg cacacacttt gcgcagatgg tgcagatcaa    180
tttggcgtcg gtactaaatc attcccatgg aacgaaggta cagatcctat tgctatcgcg    240
aaacagaagg ttgatgcagg attcgaaatt atgactaaat ggggataga gcattactgc    300
tttcatgatg tggatcttgt ctccgaaggg aactctattg aagaatatga atcaaacttg   360
aagcaagtag ttgcctactt gaaacaaaag caacaagaaa cgggtattaa actgttgtgg   420
tctaccgcga atgtcttcgg taatccaaga tacatgaatg gtgcaagcac taaccctgac    480
ttcgatgtgg ttgcacgtgc catagttcaa attaagaacg caatggatgc aggcattgag    540
ctaggtgctg aaaattatgt cttctgggga ggaagagaag gatatatgtc tttattgaat    600
actgaccaga gagagaaaaa gaacacatg gctactatgc ttactatggc cagagattac     660
gctagaagca agggttttaa aggtacgttc ttaatcgaac ccaaacccat ggagcccacg    720
aaacatcagt atgacgttga tacagaaacg gtcattggat tcctgcgtgc ccacaactta   780
gataaagatt tcaaagtcaa cattgaagtt aatcatgcga cccttgctgg acatactttt   840
gaacacgaac ttgcgtgtgc agtagatgcg ggtatgttag gtagcataga cgcaaataga   900
ggtgattatc agaatggatg ggataccgat cagttcccta ttgaccaata cgaattagta    960
caagcttgga tggaaattat caggggtggc ggctttgtaa cgggcgggac aaactttgat   1020
gctaaaacca gacgtaattc tactgactta gaggatatta ttatcgctca tataagtggt   1080
atggacgcta tggcacgtgc tttggagaat gccgcaaagt tattgcaaga atctccatac   1140
tgtaatatga gaaggagag atacgcttca ttcgattctg gaatcggtaa agatttcgag   1200
gatggtaagt taacgctaga gcaggtttat gagtacggga agaagaatgg tgaaccgaag   1260
gtcacttctg gaaaacaaga actttacgag gccatagtag caatgtacca ataa         1314
```

<210> SEQ ID NO 12
<211> LENGTH: 437
<212> TYPE: PRT
<213> ORGANISM: Artificial Sequence
<220> FEATURE:
<223> OTHER INFORMATION: Synthetic polypeptide

<400> SEQUENCE: 12

```
Met Thr Lys Glu Tyr Phe Pro Thr Ile Gly Lys Ile Arg Phe Glu Gly
1               5                   10                  15

Lys Asp Ser Lys Asn Pro Met Ala Phe His Tyr Tyr Asp Ala Glu Lys
            20                  25                  30

Glu Val Met Gly Lys Lys Met Lys Asp Trp Leu Arg Phe Ala Met Ala
        35                  40                  45

Trp Trp His Thr Leu Cys Ala Asp Gly Ala Asp Gln Phe Gly Val Gly
```

```
            50                  55                  60
Thr Lys Ser Phe Pro Trp Asn Glu Gly Thr Asp Pro Ile Ala Ile Ala
 65                  70                  75                  80

Lys Gln Lys Val Asp Ala Gly Phe Glu Ile Met Thr Lys Leu Gly Ile
                 85                  90                  95

Glu His Tyr Cys Phe His Asp Val Asp Leu Val Ser Glu Gly Asn Ser
            100                 105                 110

Ile Glu Glu Tyr Glu Ser Asn Leu Lys Gln Val Ala Tyr Leu Lys
        115                 120                 125

Gln Lys Gln Gln Glu Thr Gly Ile Lys Leu Leu Trp Ser Thr Ala Asn
130                 135                 140

Val Phe Gly Asn Pro Arg Tyr Met Asn Gly Ala Ser Thr Asn Pro Asp
145                 150                 155                 160

Phe Asp Val Val Ala Arg Ala Ile Val Gln Ile Lys Asn Ala Met Asp
                165                 170                 175

Ala Gly Ile Glu Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ser Lys
210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala His Asn Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp Ala Gly Met Leu Gly Ser Ile Asp Ala Asn Arg Gly Asp Tyr Gln
290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Phe Val Thr Gly Gly
                325                 330                 335

Thr Asn Phe Asp Ala Lys Thr Arg Arg Asn Ser Thr Asp Leu Glu Asp
            340                 345                 350

Ile Ile Ile Ala His Ile Ser Gly Met Asp Ala Met Ala Arg Ala Leu
        355                 360                 365

Glu Asn Ala Ala Lys Leu Leu Gln Glu Ser Pro Tyr Cys Asn Met Lys
370                 375                 380

Lys Glu Arg Tyr Ala Ser Phe Asp Ser Gly Ile Gly Lys Asp Phe Glu
385                 390                 395                 400

Asp Gly Lys Leu Thr Leu Glu Gln Val Tyr Glu Tyr Gly Lys Lys Asn
                405                 410                 415

Gly Glu Pro Lys Val Thr Ser Gly Lys Gln Glu Leu Tyr Glu Ala Ile
            420                 425                 430

Val Ala Met Tyr Gln
        435

<210> SEQ ID NO 13
<211> LENGTH: 1320
<212> TYPE: DNA
<213> ORGANISM: Artificial Sequence
```

<220> FEATURE:
<223> OTHER INFORMATION: Synthetic polynucleotide

<400> SEQUENCE: 13

```
atggcaaaag aatatttccc gtttacaggt aaaatcccat tcgaaggtaa ggattcaaaa      60
aatgtcatgg cttttcacta ctacgagccg gaaaaagtgg tcatgggcaa aaaaatgaaa     120
gattggttga aattcgcaat ggcatggtgg cacactctgg gaggagcaag tgcagatcaa     180
tttggcggtc aaaccagatc atacgaatgg gataaggctg aatgtcctgt tcaaagagcg     240
aaagacaaga tggacgctgg attcgaaatt atggacaagt tgggtattga atattttgc     300
tttcatgacg tggatcttgt cgaggaagcg ccaactatag ctgaatacga agaaagaatg     360
aaggctatta ctgattatgc tcaagaaaag atgaaacaat ttccgaatat taaattgctg     420
tggggtactg ctaatgtgtt tggcaacaaa agatacgcta acggcgcttc tactaaccct     480
gactttgatg tcgttgccag agcgattgta caaataaaaa atagcattga tgcaacaata     540
aagcttggcg gtacaaatta tgtcttttgg ggcggaaggg aaggttatat gtctttattg     600
aatactgacc agaagagaga aaaagaacac atggctacta tgcttggtat ggccagagat     660
tacgctagag ccaaaggttt taaaggtacg ttcttaatcg aacccaaacc catggagccc     720
tctaagcatc agtatgatgt agatacggaa actgtaatag gcttcctgaa agctcatggt     780
ctggataagg actttaaagt taatatcgag gtgaatcacg caactcttgc tggtcataca     840
ttcgagcatg aacttgcgtg tgcagtagat gcgggtatgt taggtagcat agacgcaaat     900
agaggtgatg cgcagaatgg atgggatacc gatcagttcc ctattgacaa tttcgaatta     960
acacaagcta tgttagagat cataaggaat ggcggcttgg gaaatggggg cacgaacttt    1020
gacgctaaaa ttagacgtaa ttctactgac ttagaggatt tatttatcgc tcatataagt    1080
ggtatggacg ctatggcacg tgctttgatg aacgccgcag acatcttgga aaacagtgaa    1140
ttgccagcca tgaagaaggc tagatacgct agtttttgatt ccggtatcgg caaggatttc    1200
gaggatggta aactaacttt tgagcaggtg tacgaatatg gtaaaaaagt cgaagaacca    1260
aaacaaacct ctggaaagca ggagaagtat gaaacaattg ttgctctaca ctgtaagtag    1320
```

<210> SEQ ID NO 14
<211> LENGTH: 439
<212> TYPE: PRT
<213> ORGANISM: Artificial Sequence
<220> FEATURE:
<223> OTHER INFORMATION: Synthetic polypeptide

<400> SEQUENCE: 14

```
Met Ala Lys Glu Tyr Phe Pro Phe Thr Gly Lys Ile Pro Phe Glu Gly
1               5                   10                  15

Lys Asp Ser Lys Asn Val Met Ala Phe His Tyr Tyr Glu Pro Glu Lys
            20                  25                  30

Val Val Met Gly Lys Lys Met Lys Asp Trp Leu Lys Phe Ala Met Ala
        35                  40                  45

Trp Trp His Thr Leu Gly Gly Ala Ser Ala Asp Gln Phe Gly Gly Gln
    50                  55                  60

Thr Arg Ser Tyr Glu Trp Asp Lys Ala Glu Cys Pro Val Gln Arg Ala
65                  70                  75                  80

Lys Asp Lys Met Asp Ala Gly Phe Glu Ile Met Asp Lys Leu Gly Ile
                85                  90                  95

Glu Tyr Phe Cys Phe His Asp Val Asp Leu Val Glu Glu Ala Pro Thr
            100                 105                 110
```

Ile Ala Glu Tyr Glu Arg Met Lys Ala Ile Thr Asp Tyr Ala Gln
            115                 120                 125

Glu Lys Met Lys Gln Phe Pro Asn Ile Lys Leu Leu Trp Gly Thr Ala
130                 135                 140

Asn Val Phe Gly Asn Lys Arg Tyr Ala Asn Gly Ala Ser Thr Asn Pro
145                 150                 155                 160

Asp Phe Asp Val Val Ala Arg Ala Ile Val Gln Ile Lys Asn Ser Ile
                165                 170                 175

Asp Ala Thr Ile Lys Leu Gly Gly Thr Asn Tyr Val Phe Trp Gly Gly
            180                 185                 190

Arg Glu Gly Tyr Met Ser Leu Leu Asn Thr Asp Gln Lys Arg Glu Lys
            195                 200                 205

Glu His Met Ala Thr Met Leu Gly Met Ala Arg Asp Tyr Ala Arg Ala
            210                 215                 220

Lys Gly Phe Lys Gly Thr Phe Leu Ile Glu Pro Lys Pro Met Glu Pro
225                 230                 235                 240

Ser Lys His Gln Tyr Asp Val Asp Thr Glu Thr Val Ile Gly Phe Leu
                245                 250                 255

Lys Ala His Gly Leu Asp Lys Asp Phe Lys Val Asn Ile Glu Val Asn
            260                 265                 270

His Ala Thr Leu Ala Gly His Thr Phe Glu His Glu Leu Ala Cys Ala
            275                 280                 285

Val Asp Ala Gly Met Leu Gly Ser Ile Asp Ala Asn Arg Gly Asp Ala
            290                 295                 300

Gln Asn Gly Trp Asp Thr Asp Gln Phe Pro Ile Asp Asn Phe Glu Leu
305                 310                 315                 320

Thr Gln Ala Met Leu Glu Ile Ile Arg Asn Gly Gly Leu Gly Asn Gly
                325                 330                 335

Gly Thr Asn Phe Asp Ala Lys Ile Arg Arg Asn Ser Thr Asp Leu Glu
            340                 345                 350

Asp Leu Phe Ile Ala His Ile Ser Gly Met Asp Ala Met Ala Arg Ala
            355                 360                 365

Leu Met Asn Ala Ala Asp Ile Leu Glu Asn Ser Glu Leu Pro Ala Met
            370                 375                 380

Lys Lys Ala Arg Tyr Ala Ser Phe Asp Ser Gly Ile Gly Lys Asp Phe
385                 390                 395                 400

Glu Asp Gly Lys Leu Thr Phe Glu Gln Val Tyr Glu Tyr Gly Lys Lys
                405                 410                 415

Val Glu Glu Pro Lys Gln Thr Ser Gly Lys Gln Glu Lys Tyr Glu Thr
            420                 425                 430

Ile Val Ala Leu His Cys Lys
            435

<210> SEQ ID NO 15
<211> LENGTH: 1317
<212> TYPE: DNA
<213> ORGANISM: Artificial Sequence
<220> FEATURE:
<223> OTHER INFORMATION: Synthetic polynucleotide

<400> SEQUENCE: 15
atggcgacta aagagtactt tccaggaata ggaaaaatta aattcgaagg taaagagtcc      60
aagaatccaa tggctttcag atattacgat gcggaaaagg taataatggg taaaaaaatg     120
aaggattggc tgaaattctc catggcatgg tggcacactc tgtgtgcaga aggtggagat     180

```
caatttggcg gcggtactaa acatttccca tggaacggtg atgctgacaa gttacaagct    240
gcgaaaaaca agatggacgc tggattcgaa tttatgcaga agatgggtat tgaatattat    300
tgtttccatg atgtggattt atgtgacgaa gcggacacta ttgaagaata tgaagctaac    360
ttgaaggcta ttgttgccta cgctaaacaa aagcaagaag aaacgggtat taaactgttg    420
tggggcactg ccaacgtgtt tggccacgct agatacatga atggcgccgc aactaaccct    480
gactttgatg tcgttgccag agcggctgta caaataaaaa atgcaattga tgcaacaata    540
gagcttggcg gttccaatta tgtcttttgg ggcggaaggg aaggttatat gtctttattg    600
aatactgacc agaagagaga aaaagaacat ttggctcaaa tgttgaccat tgctagagac    660
tatgcccgtg ctagaggatt aaggggacc ttcttaatcg aacccaaacc catggagccc    720
acgaaacatc agtatgacgt tgatacagaa acggtcgttg gattcctgaa agcacatggt    780
ctggataaag actttaaggt caacattgaa gttaatcatg cgacccttgc tggacatact    840
tttgaacacg aacttgcggt cgcagtagat aacgggatgt tgggctcaat tgatgcgaac    900
agaggtgact accagaatgg ttgggatacc gatcagtttc ctattgacaa ttatgagctt    960
acacaggcca tgatgcaaat tatcagaaac ggaggttttg gtgacggggg tacaaatttt   1020
gatgctaaaa cgaggagaaa ttcaaccgac ttggaagata ttttcattgc ccatatagca   1080
ggtatggatg ttatggccag ggctttggaa tccgcagcta aattgttaga ggaatctcca   1140
tataagaaaa tgttggctga cagatacgct tcattcgatt ctggaaaggg taagaatttt   1200
gaggaaggta agttaacgct agaggacgtt gttgcgtacg ctaaggctaa tggggagccc   1260
aaacaaacta gcggcaaaca agaattgtat gaagctattg taaacatgta ttgctag     1317
```

<210> SEQ ID NO 16
<211> LENGTH: 438
<212> TYPE: PRT
<213> ORGANISM: Artificial Sequence
<220> FEATURE:
<223> OTHER INFORMATION: Synthetic polypeptide

<400> SEQUENCE: 16

```
Met Ala Thr Lys Glu Tyr Phe Pro Gly Ile Gly Lys Ile Lys Phe Glu
1               5                   10                  15

Gly Lys Glu Ser Lys Asn Pro Met Ala Phe Arg Tyr Tyr Asp Ala Glu
            20                  25                  30

Lys Val Ile Met Gly Lys Lys Met Lys Asp Trp Leu Lys Phe Ser Met
        35                  40                  45

Ala Trp Trp His Thr Leu Cys Ala Glu Gly Gly Asp Gln Phe Gly Gly
    50                  55                  60

Gly Thr Lys His Phe Pro Trp Asn Gly Asp Ala Asp Lys Leu Gln Ala
65                  70                  75                  80

Ala Lys Asn Lys Met Asp Ala Gly Phe Glu Phe Met Gln Lys Met Gly
                85                  90                  95

Ile Glu Tyr Tyr Cys Phe His Asp Val Asp Leu Cys Asp Glu Ala Asp
            100                 105                 110

Thr Ile Glu Glu Tyr Glu Ala Asn Leu Lys Ala Ile Val Ala Tyr Ala
        115                 120                 125

Lys Gln Lys Gln Glu Glu Thr Gly Ile Lys Leu Leu Trp Gly Thr Ala
    130                 135                 140

Asn Val Phe Gly His Ala Arg Tyr Met Asn Gly Ala Ala Thr Asn Pro
145                 150                 155                 160
```

```
Asp Phe Asp Val Val Ala Arg Ala Ala Val Gln Ile Lys Asn Ala Ile
            165                 170                 175

Asp Ala Thr Ile Glu Leu Gly Gly Ser Asn Tyr Val Phe Trp Gly Gly
        180                 185                 190

Arg Glu Gly Tyr Met Ser Leu Leu Asn Thr Asp Gln Lys Arg Glu Lys
            195                 200                 205

Glu His Leu Ala Gln Met Leu Thr Ile Ala Arg Asp Tyr Ala Arg Ala
        210                 215                 220

Arg Gly Phe Lys Gly Thr Phe Leu Ile Glu Pro Lys Pro Met Glu Pro
225                 230                 235                 240

Thr Lys His Gln Tyr Asp Val Asp Thr Glu Thr Val Val Gly Phe Leu
            245                 250                 255

Lys Ala His Gly Leu Asp Lys Asp Phe Lys Val Asn Ile Glu Val Asn
        260                 265                 270

His Ala Thr Leu Ala Gly His Thr Phe Glu His Glu Leu Ala Val Ala
    275                 280                 285

Val Asp Asn Gly Met Leu Gly Ser Ile Asp Ala Asn Arg Gly Asp Tyr
290                 295                 300

Gln Asn Gly Trp Asp Thr Asp Gln Phe Pro Ile Asp Asn Tyr Glu Leu
305                 310                 315                 320

Thr Gln Ala Met Met Gln Ile Ile Arg Asn Gly Gly Phe Gly Asp Gly
                325                 330                 335

Gly Thr Asn Phe Asp Ala Lys Thr Arg Arg Asn Ser Thr Asp Leu Glu
            340                 345                 350

Asp Ile Phe Ile Ala His Ile Ala Gly Met Asp Val Met Ala Arg Ala
        355                 360                 365

Leu Glu Ser Ala Ala Lys Leu Leu Glu Glu Ser Pro Tyr Lys Lys Met
    370                 375                 380

Leu Ala Asp Arg Tyr Ala Ser Phe Asp Ser Gly Lys Gly Lys Glu Phe
385                 390                 395                 400

Glu Glu Gly Lys Leu Thr Leu Glu Asp Val Val Ala Tyr Ala Lys Ala
                405                 410                 415

Asn Gly Glu Pro Lys Gln Thr Ser Gly Lys Gln Glu Leu Tyr Glu Ala
            420                 425                 430

Ile Val Asn Met Tyr Cys
        435

<210> SEQ ID NO 17
<211> LENGTH: 1320
<212> TYPE: DNA
<213> ORGANISM: Artificial Sequence
<220> FEATURE:
<223> OTHER INFORMATION: Synthetic polynucleotide

<400> SEQUENCE: 17
atgccagcct actttgacca attagataga gttagattcg aaggtacaca aagcacaaat     60
ccattggcct ttagacatta aaccccgat gaaatagttc taggaaaaag aatggaagac    120
cacttgagat ttgcagcctg ttattggcat accttttgtt ggaatggtgc tgacatgttg    180
gtatgggtgc tttcgacaga ccatggcaac aacccggtga agcactggct ttagcaaaac    240
gtaaggcgga tgtcgcgttt gaattttcc ataagttgaa tgtgccatat tactgtttcc    300
acgatgttga cgtttcccca gaaggagcta gcctaaaaga atataaaaat aatttcgcac    360
aaatggtcga tgtcttagcc gctaaacagg aacagtctgg tgttaagctt ctgtggggac    420
tgctaattgt tttaccaatc ctcgttatgg tgcaggtgcg gcaaccaacc cagaccctga    480
```

```
agtttttagc tgggcagcta ctcaagtggt tactgccatg gacgctactc ataagttggg    540
tggagaaaat tacgttttat ggggaggtag agaaggttac gaaaccctgt tgaatacgat    600
ttaaggcagg aaagagagca aattggaagg ttcatgcagc tggttgtaga gcataaacac    660
aagataggct tccagggtac actactgatc gaacctaaac cacaagaacc gaccaagcat    720
caatatgatt acgacgctgc gacagtctat ggattcttaa agcaatttgg tttggagaag    780
gaaataaagt taaacattga agcgaactat gcaaccttag caggccattc ttttcaccat    840
ggcatagcaa cagccatagc attaggatta tttggtagtg ttgatgccaa tagggggggac    900 gcccagcttg gttgggatac tgatcagttt ccaaattctg ttgaggaaaa cgccttagtc    960
atgtacgaga ttctaaaggc tggcggattt actacaggag gtttgaactt tgacgctaag   1020
gttaggagac aatctactga caaatatgac ttgttctacg gtcatatcgg tgctatggat   1080
acaatggcat tgtctttaaa aatagcagct agaatgatag aggctggagg tttagatcaa   1140
agagtcgcca aaagatatgc cggttggaat ggtgagttgg acaacaaat attaaaaggg   1200 cagatgacgt taactgaaat agcgcagtac gcagaacaac ataaccttgc cccagttcat   1260
caaagcggtc accaggaatt actagagaat cttgttaatc attacttatt tgataagtga   1320
```

<210> SEQ ID NO 18
<211> LENGTH: 440
<212> TYPE: PRT
<213> ORGANISM: Artificial Sequence
<220> FEATURE:
<223> OTHER INFORMATION: Synthetic polypeptide

<400> SEQUENCE: 18

```
Met Pro Ala Tyr Phe Asp Gln Leu Asp Arg Val Arg Phe Glu Gly Thr
1               5                   10                  15

Gln Ser Thr Asn Pro Leu Ala Phe Arg His Tyr Asn Pro Asp Glu Ile
            20                  25                  30

Val Leu Gly Lys Arg Met Glu Asp His Leu Arg Phe Ala Ala Cys Tyr
        35                  40                  45

Trp His Thr Phe Cys Trp Asn Gly Ala Asp Met Phe Gly Met Gly Ala
    50                  55                  60

Phe Asp Arg Pro Trp Gln Gln Pro Gly Glu Ala Leu Ala Leu Ala Lys
65                  70                  75                  80

Arg Lys Ala Asp Val Ala Phe Glu Phe Phe His Lys Leu Asn Val Pro
                85                  90                  95

Tyr Tyr Cys Phe His Asp Val Asp Val Ser Pro Glu Gly Ala Ser Leu
            100                 105                 110

Lys Glu Tyr Lys Asn Asn Phe Ala Gln Met Val Asp Val Leu Ala Ala
        115                 120                 125

Lys Gln Glu Gln Ser Gly Val Lys Leu Leu Trp Gly Thr Ala Asn Cys
    130                 135                 140

Phe Thr Asn Pro Arg Tyr Gly Ala Gly Ala Thr Asn Pro Asp Pro
145                 150                 155                 160

Glu Val Phe Ser Trp Ala Ala Thr Gln Val Val Thr Ala Met Asp Ala
                165                 170                 175

Thr His Lys Leu Gly Gly Glu Asn Tyr Val Leu Trp Gly Gly Arg Glu
            180                 185                 190

Gly Tyr Glu Thr Leu Leu Asn Thr Asp Leu Arg Gln Glu Arg Glu Gln
        195                 200                 205

Ile Gly Arg Phe Met Gln Leu Val Val Glu His Lys His Lys Ile Gly
```

```
            210                 215                 220
Phe Gln Gly Thr Leu Leu Ile Glu Pro Lys Pro Gln Glu Pro Thr Lys
225                 230                 235                 240

His Gln Tyr Asp Tyr Asp Ala Ala Thr Val Tyr Gly Phe Leu Lys Gln
                245                 250                 255

Phe Gly Leu Glu Lys Glu Ile Lys Leu Asn Ile Glu Ala Asn Tyr Ala
                260                 265                 270

Thr Leu Ala Gly His Ser Phe His His Gly Ile Ala Thr Ala Ile Ala
                275                 280                 285

Leu Gly Leu Phe Gly Ser Val Asp Ala Asn Arg Gly Asp Ala Gln Leu
            290                 295                 300

Gly Trp Asp Thr Asp Gln Phe Pro Asn Ser Val Glu Glu Asn Ala Leu
305                 310                 315                 320

Val Met Tyr Glu Ile Leu Lys Ala Gly Gly Phe Thr Thr Gly Gly Leu
                325                 330                 335

Asn Phe Asp Ala Lys Val Arg Arg Gln Ser Thr Asp Lys Tyr Asp Leu
                340                 345                 350

Phe Tyr Gly His Ile Gly Ala Met Asp Thr Met Ala Leu Ser Leu Lys
                355                 360                 365

Ile Ala Ala Arg Met Ile Glu Ala Gly Leu Asp Gln Arg Val Ala
            370                 375                 380

Lys Arg Tyr Ala Gly Trp Asn Gly Glu Leu Gly Gln Gln Ile Leu Lys
385                 390                 395                 400

Gly Gln Met Thr Leu Thr Glu Ile Ala Gln Tyr Ala Glu Gln His Asn
                405                 410                 415

Leu Ala Pro Val His Gln Ser Gly His Gln Glu Leu Leu Glu Asn Leu
                420                 425                 430

Val Asn His Tyr Leu Phe Asp Lys
            435                 440

<210> SEQ ID NO 19
<211> LENGTH: 1311
<212> TYPE: DNA
<213> ORGANISM: Artificial Sequence
<220> FEATURE:
<223> OTHER INFORMATION: Synthetic polynucleotide

<400> SEQUENCE: 19
atgccctatt tcccaggtgt tgaaaaagtt agattcgaag ccctgcaag tacatctgca      60 ctagcattta gacattacga tgcgaataaa ctgatacttg aaagccaat gcgtgaacac     120 ttgagaatgg cagcatgtta ttggcatacc tttgtttggc ccggtgctga catgtttggt     180
atgggtactt tcaagagacc atggcaaaga agtggagagc aatggaagt agctataggg     240 aaggcagaag cggcttttga gttcttctcc aaactaggga ttgattatta tagctttcat     300
gataccgacg ttgctcctga aggatctagc ctaaaagaat ataggaatca tttcgcacaa     360
atggtcgatc atttagaaag acatcaggaa cagaccggta ttaagttgct ttggggggaca     420 gctaactgct tttctaatcc aaggtttgcc gcaggcgcag cttcaaatcc tgatcctgaa     480
gttttcgcat tgcagctgc gcaagtcttc agcgcaatga atgctacatt gagattgaaa     540
ggtgctaatt atgttttgtg gggtggaaga gaaggttatg agactttgct gaacactgat     600
ttaaagagag aaagggagca attgggtcgt ttatgcgta tggttgtaga gcataaacac     660
aagataggct tcactggtga tttgctgatc gaacctaaac cacaagaacc gaccaagcat     720
caatatgatt acgactcagc gacagtcttt ggattcttac acgaatatgg tttggagcac     780
```

```
gaaataaagg ttaacgttga agcgaaccat gcaaccttag caggccattc ttttcaccat    840
gaaatagcaa cagccgtatc actaggtata tttgggagta ttgatgccaa tagggggggac    900 ccccagaatg ggtgggacac agaccaattt ccaaattctg tagaagagat gactttagcc    960
acatacgaaa ttctaaaggc tggcggattt aagaatggag atacaacttt tgattctaag   1020
gttaggagac aatctttaga cgaagtggac ttgttccacg gtcatgttgc agctatggat   1080
gtactagcct tggctctaga gagagctgcg gctatggttc aagatgacag attgcaacaa   1140
tttaaagatc agagatatgc aggttggagt cagcctttag ggcaggcggt attagcgggc   1200
gagttctcct tagaaagtct tgccgaacat gcttttgcca acgcattaga ccctcaagct   1260
gtatctgggc gtcaagaaat gcttgagggt gttgttaacc gttttattta a            1311
```

<210> SEQ ID NO 20
<211> LENGTH: 436
<212> TYPE: PRT
<213> ORGANISM: Artificial Sequence
<220> FEATURE:
<223> OTHER INFORMATION: Synthetic polypeptide

<400> SEQUENCE: 20

```
Met Pro Tyr Phe Pro Gly Val Glu Lys Val Arg Phe Glu Gly Pro Ala
1               5                   10                  15

Ser Thr Ser Ala Leu Ala Phe Arg His Tyr Asp Ala Asn Lys Leu Ile
            20                  25                  30

Leu Gly Lys Pro Met Arg Glu His Leu Arg Met Ala Ala Cys Tyr Trp
        35                  40                  45

His Thr Phe Val Trp Pro Gly Ala Asp Met Phe Gly Met Gly Thr Phe
    50                  55                  60

Lys Arg Pro Trp Gln Arg Ser Gly Glu Pro Met Glu Val Ala Ile Gly
65                  70                  75                  80

Lys Ala Glu Ala Ala Phe Glu Phe Phe Ser Lys Leu Gly Ile Asp Tyr
                85                  90                  95

Tyr Ser Phe His Asp Thr Asp Val Ala Pro Glu Gly Ser Ser Leu Lys
            100                 105                 110

Glu Tyr Arg Asn His Phe Ala Gln Met Val Asp His Leu Glu Arg His
        115                 120                 125

Gln Glu Gln Thr Gly Ile Lys Leu Leu Trp Gly Thr Ala Asn Cys Phe
    130                 135                 140

Ser Asn Pro Arg Phe Ala Ala Gly Ala Ala Ser Asn Pro Asp Pro Glu
145                 150                 155                 160

Val Phe Ala Phe Ala Ala Ala Gln Val Phe Ser Ala Met Asn Ala Thr
                165                 170                 175

Leu Arg Leu Lys Gly Ala Asn Tyr Val Leu Trp Gly Gly Arg Glu Gly
            180                 185                 190

Tyr Glu Thr Leu Leu Asn Thr Asp Leu Lys Arg Glu Arg Glu Gln Leu
        195                 200                 205

Gly Arg Phe Met Arg Met Val Val Glu His Lys His Lys Ile Gly Phe
    210                 215                 220

Thr Gly Asp Leu Leu Ile Glu Pro Lys Pro Gln Glu Pro Thr Lys His
225                 230                 235                 240

Gln Tyr Asp Tyr Asp Ser Ala Thr Val Phe Gly Phe Leu His Glu Tyr
                245                 250                 255

Gly Leu Glu His Glu Ile Lys Val Asn Val Glu Ala Asn His Ala Thr
            260                 265                 270
```

Leu Ala Gly His Ser Phe His His Glu Ile Ala Thr Ala Val Ser Leu
            275                 280                 285

Gly Ile Phe Gly Ser Ile Asp Ala Asn Arg Gly Asp Pro Gln Asn Gly
        290                 295                 300

Trp Asp Thr Asp Gln Phe Pro Asn Ser Val Glu Glu Met Thr Leu Ala
305                 310                 315                 320

Thr Tyr Glu Ile Leu Lys Ala Gly Gly Phe Lys Asn Gly Gly Tyr Asn
                325                 330                 335

Phe Asp Ser Lys Val Arg Arg Gln Ser Leu Asp Glu Val Asp Leu Phe
            340                 345                 350

His Gly His Val Ala Ala Met Asp Val Leu Ala Leu Ala Leu Glu Arg
        355                 360                 365

Ala Ala Ala Met Val Gln Asp Asp Arg Leu Gln Gln Phe Lys Asp Gln
    370                 375                 380

Arg Tyr Ala Gly Trp Ser Gln Pro Leu Gly Gln Ala Val Leu Ala Gly
385                 390                 395                 400

Glu Phe Ser Leu Glu Ser Leu Ala Glu His Ala Phe Ala Asn Ala Leu
                405                 410                 415

Asp Pro Gln Ala Val Ser Gly Arg Gln Glu Met Leu Glu Gly Val Val
            420                 425                 430

Asn Arg Phe Ile
        435

<210> SEQ ID NO 21
<211> LENGTH: 1410
<212> TYPE: DNA
<213> ORGANISM: Artificial Sequence
<220> FEATURE:
<223> OTHER INFORMATION: Synthetic polynucleotide

<400> SEQUENCE: 21

```
atgcagcatc aagttaaaga atattttcca acgttccaa aaattacatt cgagggtcaa      60
aacgctaaat ccgtacttgc atacagagaa tacaatgctt cagaagttat catgggaaag    120
actatggagg aatggtgcag gttcgcagtt tgttactggc ataccttcgg caattctggc    180
tcagacccat tcggtggaga aacctatact aatagattat ggaatgagtc tttagaaaga    240
gcgaatatat cttccaggga agattgttg gaagccgcaa agtgcaaagc tgacgcagct     300
tttgaaactt ttacgaaact aggtgttaag tattatacct ttcatgacgt ggatttaatt    360
tctgagggcg ctaacttgga ggagtctcag tccctgttgg acgagatatc tgattatctt    420
cttgataaac aaaatcaaac aggggtaaga tgcctatggg gtactaccaa tctgttcgga    480
catagacgtt ttatgaatgg tgcttctact aatccagata tgaaagtttt tgctcacgcc    540
gcagctagag ttaagaaggc tatggagatt accctgaagt tgggtggaca aaactttgtg    600
ttctgggggg gtagggaggg cttccagtct atcttaaata cagatatgaa gacggaattg    660
gatcacatgg cagccttctt caagctggtg gttgcatata aaaaggaact gggagctacc    720
ttccagtttc ttgttgaacc aaagccaagg gagcccatga acaccaata tgattacgat    780
gcagctacgg ttgtcgcgtt cttacacact tatgggttac aaaacgactt caaattaaat    840
atagaaccaa atcatacaac ccttgcaggc catgattacg agcatgacat ttactatgcc    900
gcaagttaca agatgctagg ttctgtagat tgtaacacgg gcgacccgct tgttggatgg    960
gacactgatc agtttttgat ggatgaaaag aaagctgtct tagtcatgaa gaagattgta   1020
gaaattggcg gattggctcc tggaggtttg aactttgacg ctaaggttag acgtgagtct   1080
```

```
actgacttgg aggatatctt tatcgctcat attggttcca tggattgttt tgccagaggt   1140
ctaagacaag cggctaagtt attggaaaag aatgaattgg gagaattggt aaagcagaga   1200
tatgcatctt ggaaaagtac cttaggggag aggattgaac agggccaggc gacattagaa   1260
gaagtagccg cttatgcaaa agaaagcggt gaacctgacc acgttagtgg taagcaagaa   1320
cttgctgaat tgatgtggtc aactgttgca ttagctacag gtatatggca ggatcatgtt   1380
acgtgttctc ttacaaagaa ttggtgctag                                    1410
```

<210> SEQ ID NO 22
<211> LENGTH: 469
<212> TYPE: PRT
<213> ORGANISM: Artificial Sequence
<220> FEATURE:
<223> OTHER INFORMATION: Synthetic polypeptide

<400> SEQUENCE: 22

```
Met Gln His Gln Val Lys Glu Tyr Phe Pro Asn Val Pro Lys Ile Thr
1               5                   10                  15

Phe Glu Gly Gln Asn Ala Lys Ser Val Leu Ala Tyr Arg Glu Tyr Asn
            20                  25                  30

Ala Ser Glu Val Ile Met Gly Lys Thr Met Glu Glu Trp Cys Arg Phe
        35                  40                  45

Ala Val Cys Tyr Trp His Thr Phe Gly Asn Ser Gly Ser Asp Pro Phe
    50                  55                  60

Gly Gly Glu Thr Tyr Thr Asn Arg Leu Trp Asn Glu Ser Leu Glu Arg
65                  70                  75                  80

Ala Asn Ile Ser Ser Arg Glu Arg Leu Leu Glu Ala Ala Lys Cys Lys
                85                  90                  95

Ala Asp Ala Ala Phe Glu Thr Phe Thr Lys Leu Gly Val Lys Tyr Tyr
            100                 105                 110

Thr Phe His Asp Val Asp Leu Ile Ser Glu Gly Ala Asn Leu Glu Glu
        115                 120                 125

Ser Gln Ser Leu Leu Asp Glu Ile Ser Asp Tyr Leu Leu Asp Lys Gln
    130                 135                 140

Asn Gln Thr Gly Val Arg Cys Leu Trp Gly Thr Thr Asn Leu Phe Gly
145                 150                 155                 160

His Arg Arg Phe Met Asn Gly Ala Ser Thr Asn Pro Asp Met Lys Val
                165                 170                 175

Phe Ala His Ala Ala Arg Val Lys Lys Ala Met Glu Ile Thr Leu
            180                 185                 190

Lys Leu Gly Gly Gln Asn Phe Val Phe Trp Gly Gly Arg Glu Gly Phe
        195                 200                 205

Gln Ser Ile Leu Asn Thr Asp Met Lys Thr Glu Leu Asp His Met Ala
    210                 215                 220

Ala Phe Phe Lys Leu Val Val Ala Tyr Lys Lys Glu Leu Gly Ala Thr
225                 230                 235                 240

Phe Gln Phe Leu Val Glu Pro Lys Pro Arg Glu Pro Met Lys His Gln
                245                 250                 255

Tyr Asp Tyr Asp Ala Ala Thr Val Val Ala Phe Leu His Thr Tyr Gly
            260                 265                 270

Leu Gln Asn Asp Phe Lys Leu Asn Ile Glu Pro Asn His Thr Thr Leu
        275                 280                 285

Ala Gly His Asp Tyr Glu His Asp Ile Tyr Tyr Ala Ala Ser Tyr Lys
    290                 295                 300
```

```
Met Leu Gly Ser Val Asp Cys Asn Thr Gly Asp Pro Leu Val Gly Trp
305                 310                 315                 320

Asp Thr Asp Gln Phe Leu Met Asp Glu Lys Lys Ala Val Leu Val Met
                325                 330                 335

Lys Lys Ile Val Glu Ile Gly Gly Leu Ala Pro Gly Gly Leu Asn Phe
            340                 345                 350

Asp Ala Lys Val Arg Arg Glu Ser Thr Asp Leu Glu Asp Ile Phe Ile
        355                 360                 365

Ala His Ile Gly Ser Met Asp Cys Phe Ala Arg Gly Leu Arg Gln Ala
    370                 375                 380

Ala Lys Leu Leu Glu Lys Asn Glu Leu Gly Glu Leu Val Lys Gln Arg
385                 390                 395                 400

Tyr Ala Ser Trp Lys Ser Thr Leu Gly Glu Arg Ile Glu Gln Gly Gln
                405                 410                 415

Ala Thr Leu Glu Glu Val Ala Ala Tyr Ala Lys Glu Ser Gly Glu Pro
                420                 425                 430

Asp His Val Ser Gly Lys Gln Glu Leu Ala Glu Leu Met Trp Ser Thr
            435                 440                 445

Val Ala Leu Ala Thr Gly Ile Trp Gln Asp His Val Thr Cys Ser Leu
        450                 455                 460

Thr Lys Asn Trp Cys
465

<210> SEQ ID NO 23
<211> LENGTH: 1308
<212> TYPE: DNA
<213> ORGANISM: Artificial Sequence
<220> FEATURE:
<223> OTHER INFORMATION: Synthetic polynucleotide

<400> SEQUENCE: 23
atggaatatt tcccaggaat aagtaatatc aaatatgaag ggtctgcgtc aatgaatgat      60
ctaagtttta atggtataa tgctgaacaa gttgttttag aaagaaaat gaaggaccat      120 ttaagatttg cggtttgtta ttggcatacc ttttgctacc aaggtaatga tcaattcggt      180
ggacctactt taaacagacc gtggtgcggt gatgcagatc caatggttga agctaaaaaa      240
aagtgtgatg cggcttttga gttcttcacg aaacttggcg tagaatacta ttgcttccat      300
gatagagata tcgttgccga gggtgagact cttgaagaaa ccaacaggag attggatgaa      360
atcagtgatt atatgctgga aaagcaaaaa caaacgggtg taaagttatt atggggtact      420
gctaacatgt ttggtgaccg tgtgtttatg aacggagctt ctacgaatcc tgatgcccat      480
gtgtttgctt tagcagcagc gcaggtaaaa aaggctatgg acattacaaa aaaactggga      540
ggtgaaaatt atgtgttttg gggtggcaga gaaggttacc agtctatttt aaattcttta      600
cctggtaaag aattagacca catgggtcaa tttatgcgta tggctgttga atataagaaa      660
aagatagggg ctacgttcca actttttgatc gagccaaaac ctaggagcc gacaaaacat      720 cagtatgatt acgatgcaca aactgtcatc ggtttcctga ggaaatacgg tcttgaaaaa      780
gatttcaagt taaatattga gcccaatcac acgacattag caggtcacga ttatgagcac      840
gatatagttt tcgcttgtaa tgagggtatg ctaggctcag tagatgcgaa cactggagat      900
acccttctgg gctgggatac agaccagttt ccaatggacg taagaaagc cgttatcgtg      960 atgtaccata ttataagagc aggggccctt cactcaggag gtttgaattt tgacgctcac     1020
gttaggagag aatctaccga tatggaagat agatttattg cacacattgg tgctatgac     1080
```

```
actttcgcta gagcattgtt aatcgtggag aagatcatga atgacaaaat ttatcaagaa    1140
atggttgata aaagatacga gtcctacaca accggtattg gggccaggat cgaaaatggg    1200
gaggctactt ttgaagagtg tgaaaaatac attctggaaa atggtaaacc cgaacctcaa    1260
tctgctaagc aagagaaatt cgaaatgtta ttaaatcatt acgtctga                 1308
```

<210> SEQ ID NO 24
<211> LENGTH: 435
<212> TYPE: PRT
<213> ORGANISM: Artificial Sequence
<220> FEATURE:
<223> OTHER INFORMATION: Synthetic polypeptide

<400> SEQUENCE: 24

```
Met Glu Tyr Phe Pro Gly Ile Ser Asn Ile Lys Tyr Glu Gly Ser Ala
1               5                   10                  15

Ser Met Asn Asp Leu Ser Phe Lys Trp Tyr Asn Ala Glu Gln Val Val
                20                  25                  30

Leu Gly Lys Lys Met Lys Asp His Leu Arg Phe Ala Val Cys Tyr Trp
            35                  40                  45

His Thr Phe Cys Tyr Gln Gly Asn Asp Gln Phe Gly Gly Pro Thr Leu
        50                  55                  60

Asn Arg Pro Trp Cys Gly Asp Ala Asp Pro Met Val Glu Ala Lys Lys
65                  70                  75                  80

Lys Cys Asp Ala Ala Phe Glu Phe Phe Thr Lys Leu Gly Val Glu Tyr
                85                  90                  95

Tyr Cys Phe His Asp Arg Asp Ile Val Ala Glu Gly Glu Thr Leu Glu
            100                 105                 110

Glu Thr Asn Arg Arg Leu Asp Glu Ile Ser Asp Tyr Met Leu Glu Lys
        115                 120                 125

Gln Lys Gln Thr Gly Val Lys Leu Leu Trp Gly Thr Ala Asn Met Phe
    130                 135                 140

Gly Asp Arg Val Phe Met Asn Gly Ala Ser Thr Asn Pro Asp Ala His
145                 150                 155                 160

Val Phe Ala Leu Ala Ala Ala Gln Val Lys Lys Ala Met Asp Ile Thr
                165                 170                 175

Lys Lys Leu Gly Gly Glu Asn Tyr Val Phe Trp Gly Gly Arg Glu Gly
            180                 185                 190

Tyr Gln Ser Ile Leu Asn Ser Leu Pro Gly Lys Glu Leu Asp His Met
        195                 200                 205

Gly Gln Phe Met Arg Met Ala Val Glu Tyr Lys Lys Lys Ile Gly Ala
    210                 215                 220

Thr Phe Gln Leu Leu Ile Glu Pro Lys Pro Arg Glu Pro Thr Lys His
225                 230                 235                 240

Gln Tyr Asp Tyr Asp Ala Gln Thr Val Ile Gly Phe Leu Arg Lys Tyr
                245                 250                 255

Gly Leu Glu Lys Asp Phe Lys Leu Asn Ile Glu Pro Asn His Thr Thr
            260                 265                 270

Leu Ala Gly His Asp Tyr Glu His Asp Ile Val Phe Ala Cys Asn Glu
        275                 280                 285

Gly Met Leu Gly Ser Val Asp Ala Asn Thr Gly Asp Thr Leu Leu Gly
    290                 295                 300

Trp Asp Thr Asp Gln Phe Pro Met Asp Val Lys Lys Ala Val Ile Val
305                 310                 315                 320
```

```
Met Tyr His Ile Ile Arg Ala Gly Gly Leu His Ser Gly Gly Leu Asn
                325                 330                 335

Phe Asp Ala His Val Arg Arg Glu Ser Thr Asp Met Glu Asp Arg Phe
            340                 345                 350

Ile Ala His Ile Gly Ala Met Asp Thr Phe Ala Arg Ala Leu Leu Ile
            355                 360                 365

Val Glu Lys Ile Met Asn Asp Lys Ile Tyr Gln Glu Met Val Asp Lys
        370                 375                 380

Arg Tyr Glu Ser Tyr Thr Thr Gly Ile Gly Ala Arg Ile Glu Asn Gly
385                 390                 395                 400

Glu Ala Thr Phe Glu Glu Cys Glu Lys Tyr Ile Leu Glu Asn Gly Lys
            405                 410                 415

Pro Glu Pro Gln Ser Ala Lys Gln Glu Lys Phe Glu Met Leu Leu Asn
            420                 425                 430

His Tyr Val
        435
```

PENTOSE FERMENTATION BY A RECOMBINANT MICROORGANISM

CROSS-REFERENCES TO RELATED APPLICATIONS

The present application is a national stage application filed under 35 USC §371, and claims priority to PCT/US2013/070009, filed Nov. 14, 2013, which claims priority to U.S. Prov. Appln. Ser. No. 61/728,398, filed Nov. 20, 2012, each of which is hereby incorporated by reference in its entirety for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file CX3-125WO1_ST25.TXT, created on Nov. 5, 2013, 70,459 bytes, machine format IBM-PC, MS Windows operating system, is hereby incorporated by reference.

FIELD OF THE INVENTION

The present invention provides methods and compositions suitable for use in the isomerization of xylose to xylulose, as well as methods and compositions suitable for use in the conversion of xylose to xylitol and xylulose, including nucleic acid constructs, recombinant fungal host cells, and related materials.

BACKGROUND

Ethanol and ethanol fuel blends are widely used in Brazil and in the United States as a transportation fuel. Combustion of these fuels is believed to produce fewer of the harmful exhaust emissions (e.g., hydrocarbons, nitrogen oxide, and volatile organic compounds (VOCs)) that are generated by the combustion of petroleum. Bioethanol is a particularly favored form of ethanol because the plant biomass from which it is produced utilizes sunlight, an energy source that is renewable. In the United States, ethanol is used in gasoline blends that are from 5% to 85% ethanol. Blends of up to 10% ethanol (E10) are approved for use in all gasoline vehicles in the U.S. and blends of up to 85% ethanol (E85) can be utilized in specially engineered flexible-fuel vehicles (FFV). The Brazilian government has mandated the use of ethanol-gasoline blends as a vehicle fuel, and the mandatory blend has been 25% ethanol (E25) since 2007.

Bioethanol is currently produced by the fermentation of hexose sugars that are obtained from carbon feedstocks. Currently, only the sugar from sugar cane and starch from feedstock such as corn can be economically converted. There is, however, much interest in using lignocellulosic feedstocks where the cellulose part of a plant is broken down to sugars and subsequently converted to ethanol. Lignocellulosic biomass is made up of cellulose, hemicelluloses, and lignin. Cellulose and hemicellulose can be hydrolyzed in a saccharification process to sugars that can be subsequently converted to ethanol via fermentation. The major fermentable sugars from lignocelluloses are glucose and xylose. For economical ethanol yields, a strain that can effectively convert all the major sugars present in cellulosic feedstock would be highly desirable.

SUMMARY OF THE INVENTION

The present invention provides methods and compositions suitable for use in the isomerization of xylose to xylulose, as well as methods and compositions suitable for use in the conversion of xylose to xylitol and xylulose, including nucleic acid constructs, recombinant fungal host cells, and related materials.

In some embodiments, the present invention provides recombinant fungal host cells comprising at least one nucleic acid construct, wherein the nucleic acid construct comprises at least one polynucleotide encoding a xylose isomerase, and/or at least one polynucleotide encoding a xylitol dehydrogenase, and/or at least one polynucleotide encoding a xylulokinase. In some additional embodiments, the recombinant fungal host cell comprises at least one nucleic acid construct, wherein the nucleic acid construct comprises at least one polynucleotide encoding a xylose isomerase, at least one polynucleotide encoding a xylitol dehydrogenase, and/or at least one polynucleotide encoding a xylulokinase. In some additional embodiments, the recombinant fungal host cell comprises at least one nucleic acid construct, wherein the nucleic acid construct comprises at least one polynucleotide encoding a xylose isomerase, at least one polynucleotide encoding a xylitol dehydrogenase, and at least one polynucleotide encoding a xylulokinase. In some embodiments, the xylose isomerase, xylitol dehydrogenase, and xylulokinase are eukaryotic or prokaryotic enzymes. In some additional embodiments, the xylose isomerase, xylitol dehydrogenase, and xylulokinase are eukaryotic enzymes. In some further embodiments, the xylose isomerase, xylitol dehydrogenase, and xylulokinase are fungal enzymes. In some additional embodiments, the nucleic acid construct(s) further comprise(s) at least one genetic element that facilitates stable integration into a fungal host genome. In some embodiments, the genetic element facilitates integration into a fungal host genome by homologous recombination. In some additional embodiments, the genetic element comprises a prokaryotic or eukaryotic origin of replication and/or a centromeric maintenance sequence. In some embodiments, the origin of replication and/or centromeric maintenance sequence is a fungal sequence. In some additional embodiments, the fungal origin of replication is a yeast origin of replication. In yet some additional embodiments, at least one of the polynucleotide sequences is operatively linked to a promoter sequence that is functional in a fungal cell. In some further embodiments, the promoter sequence is a fungal promoter sequence. In some embodiments, the fungal promoter sequence is a yeast promoter sequence. In some additional embodiments, the polynucleotide sequence is operatively linked to a transcription termination sequence that is functional in a fungal cell. In some more embodiments, the polynucleotide sequence contains codons optimized for expression in a yeast cell. In some further embodiments, at least one polynucleotide is integrated into the host cell genome. In yet some additional embodiments, the host cell has had one or more native genes deleted from its genome. In some embodiments, the deletion of the one or more native gene results in one or more phenotypes selected from increased transport of xylose into the host cell, increased xylulokinase activity, increased xylitol dehydrogenase activity, increased xylose isomerase activity, increased xylose reductase activity, increased flux through the pentose phosphate pathway, decreased sensitivity to catabolite repression, increased tolerance to ethanol, increased tolerance to acetate, increased tolerance to increased osmolarity, increased tolerance to low pH, and reduced production of by products, wherein comparison is made with respect to the corresponding host cell without the deletion(s). In some further embodiments, the host cell is altered to overexpress one or more polynucleotides. In some embodiments, the overexpression results in one or more phenotypes selected from increased transport of xylose into the host cell, increased xylulokinase activity, increased xylitol dehydrogenase activity, increased xylose isomerase activity, increased xylose reductase activity, increased flux through the pentose phosphate pathway, decreased sensitivity to catabolite repression, increased tolerance to ethanol, increased tolerance to acetate, increased tolerance to increased osmolarity, increased tolerance to low pH, and reduced product of by products, wherein comparison is made to the corresponding unaltered host cell. In some additional embodiments, the nucleic acid construct(s) comprise(s) at least one polynucleotide sequence encoding at least one xylose isomerase, and/or at least one xylitol dehydrogenase, and/or at least one xylulokinase, wherein the polynucleotide is selected from: (a) a polynucleotide that encodes a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 8494, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:2, 8, 10, 12, 14, 16, 18, 20, 22, and/or 24; a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:4; and a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:6; and (b) a polynucleotide that hybridizes under stringent hybridization conditions to the complement of a polynucleotide that encodes a polypeptide having the amino acid sequence of SEQ ID NO:2, 4, 6, 8, 10, 12, 14, 16, 18, 20, 22, and/or 24. In some additional embodiments, the nucleic acid construct(s) comprise(s) at least one polynucleotide sequence encoding at least one xylose isomerase, and/or at least one xylitol dehydrogenase, and/or at least one xylulokinase, wherein the polynucleotide is selected from: (a) a polynucleotide that encodes a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:2, 8, 10, 12, 14, 16, 18, 20, 22, and/or 24; a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:4; and a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:6; and (b) a polynucleotide that hybridizes under stringent hybridization conditions to the complement of a polynucleotide that encodes a polypeptide having the amino acid sequence of SEQ ID NO:2, 4, 6, 8, 10, 12, 14, 16, 18, 20, 22, and/or 24. In some additional embodiments, the recombinant fungal host cell comprises at least one nucleic acid construct, wherein the nucleic acid construct comprises at least one polynucleotide encoding a xylose isomerase, at least one polynucleotide encoding a xylitol dehydrogenase, and/or at least one polynucleotide encoding a xylulokinase. In some additional embodiments, the recombinant fungal host cell comprises at least one nucleic acid construct, wherein the nucleic acid construct comprises at least one polynucleotide encoding a xylose isomerase, at least one polynucleotide encoding a xylitol dehydrogenase, and at least one polynucleotide encoding a xylulokinase. In some embodiments, the nucleic acid construct(s) comprise(s) at least one polynucleotide sequence encoding at least one xylose isomerase, and/or at least one xylitol dehydrogenase, and/or at least one xylulokinase, wherein the polynucleotide is selected from: (a) a polynucleotide that encodes a polypeptide comprising an amino acid sequence having at least 70%, least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:2, 8, 10, 12, 14, 16, 18, 20, 22, and/or 24; a polypeptide comprising an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:4; a polypeptide comprising an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 949%, at least 95%, at least 96%, at least 97%, at least 98%, at least 99%, or at least 100% identity to SEQ ID NO:6; and (b) a polynucleotide that hybridizes under stringent hybridization conditions to the complement of a polynucleotide that encodes a polypeptide having the amino acid sequence of SEQ ID NO:2, 4, 6, 8, 10, 12, 14, 16, 18, 20, 22, and/or 24. In some embodiments, the nucleic acid construct(s) comprise(s) at least one polynucleotide sequence encoding at least one xylose isomerase, at least one xylitol dehydrogenase, and/or at least one xylulokinase, wherein the polynucleotide is selected from: (a) a polynucleotide that encodes a polypeptide comprising an amino acid sequence having at least 70%, least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:2, 8, 10, 12, 14, 16, 18, 20, 22, and/or 24; a polypeptide comprising an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 959%, at least 96%, at least 97%, at least 98%, at least 99%, or at least 100% identity to SEQ ID NO:4; a polypeptide comprising an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:6; and (b) a polynucleotide that hybridizes under stringent hybridization conditions to the complement of a polynucleotide that encodes a polypeptide having the amino acid sequence of SEQ ID NO:2, 4, 6, 8, 10, 12, 14, 16, 18, 20, 22, and/or 24. In some embodiments, the nucleic acid construct(s) comprise(s) at least one polynucleotide sequence comprising at least one sequence selected from SEQ ID NOS:1, 7, 9, 11, 13, 15, 17, 19, 21, and 23; SEQ ID NO:3; and SEQ ID NO:5. In some additional embodiments, the host cell is a yeast cell. In some further embodiments, the host cell is *Saccharomyces cerevisiae*.

The present invention also provides recombinant fungal host cells comprising at least one nucleic acid construct, wherein the nucleic acid construct comprises at least one polynucleotide encoding a xylose isomerase. In some embodiments, the xylose isomerase is a eukaryotic or prokaryotic enzyme, while in some alternative embodiments, the xylose isomerase is a eukaryotic enzyme. In some embodiments, the xylose isomerase is a *G. trabeum* xylose isomerase, an *Orpinomyces* xylose isomerase, a xylose isomerase obtained from a bovine rumen, a xylose isomerase obtained from a human gut, a *C. boidinii* xylose isomerase, *P. infestans* xylose isomerase, or *B. hominis* xylose isomerase. In some additional embodiments, at least one nucleic acid construct further comprises at least one genetic element that facilitates stable integration into a fungal host genome. In some embodiments, the genetic element facilitates integration into a fungal host genome by homologous recombination. In some additional embodiments, the genetic element comprises a prokaryotic or eukaryotic origin of replication and/or a centromeric plasmid maintenance sequence. In some embodiments, the origin of replication and/or centromeric plasmid maintenance sequence is a fungal sequence. In some additional embodiments, the fungal origin of replication is a yeast origin of replication. In yet some additional embodiments, at least one of the polynucleotide sequences is operatively linked to a promoter sequence that is functional in a fungal cell. In some further embodiments, the promoter sequence is a fungal promoter sequence. In some embodiments, the fungal promoter sequence is a yeast promoter sequence. In some additional embodiments, the polynucleotide sequence is operatively linked to a transcription termination sequence that is functional in a fungal cell. In some more embodiments, the polynucleotide sequence contains codons optimized for expression in a yeast cell. In some further embodiments, at least one polynucleotide is integrated into the host cell genome. In yet some additional embodiments, the host cell has had one or more native genes deleted from its genome. In some embodiments, the deletion of one or more native gene results in one or more phenotypes selected from increased transport of xylose into the host cell, increased xylulokinase activity, increased xylitol dehydrogenase activity, increased xylose isomerase activity, increased xylose reductase activity, increased flux through the pentose phosphate pathway, decreased sensitivity to catabolite repression, increased tolerance to ethanol, increased tolerance to acetate, increased tolerance to increased osmolarity, increased tolerance to low pH, and reduced production of by products, wherein comparison is made with respect to the corresponding host cell without the deletion(s). In some further embodiments, the host cell is altered to overexpress one or more polynucleotides. In some embodiments, the overexpression results in one or more phenotypes selected from increased transport of xylose into the host cell, increased xylulokinase activity, increased xylitol dehydrogenase activity, increased xylose isomerase activity, increased xylose reductase activity, increased flux through the pentose phosphate pathway, decreased sensitivity to catabolite repression, increased tolerance to ethanol, increased tolerance to acetate, increased tolerance to increased osmolarity, increased tolerance to low pH, and reduced product of by products, wherein comparison is made to the corresponding unaltered host cell. In some embodiments, the nucleic acid construct(s) comprise(s) at least one polynucleotide sequence comprising at least one sequence selected from SEQ ID NOS:1, 7, 9, 11, 13, 15, 17, 19, 21, and 23; SEQ ID NO:3 and SEQ ID NO:5. In some additional embodiments, the host cell is a yeast cell. In some further embodiments, the host cell is *Saccharomyces cerevisiae*. In some embodiments, the nucleic acid construct comprises at least one polynucleotide sequence encoding at least one xylose isomerase, wherein the polynucleotide is selected from: (a) a polynucleotide that encodes a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:8, 10, 12, 14, 16, 18, 20, 22, and/or 24; and (b) a polynucleotide that hybridizes under stringent hybridization conditions to the complement of a polynucleotide that encodes a polypeptide having the amino acid sequence of SEQ ID NO:8, 10, 12, 14, 16, 18, 20, 22, and/or 24. In some additional embodiments, the nucleic acid construct comprises at least one polynucleotide sequence encoding at least one xylose isomerase, wherein the polynucleotide is selected from: (a) a polynucleotide that encodes a polypeptide comprising an amino acid sequence having at least 70%, least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:8, 10, 12, 14, 16, 18, 20, 22, and/or 24; and (b) a polynucleotide that hybridizes under stringent hybridization conditions to the complement of a polynucleotide that encodes a polypeptide having the amino acid sequence of SEQ ID NO:8, 10, 12, 14, 16, 18, 20, 22, and/or 24. In some embodiments, the nucleic acid construct(s) comprise at least one polynucleotide sequence comprising at least one sequence selected from SEQ ID NOS:7, 9, 11, 13, 15, 17, 19, 21, and/or 23. In some additional embodiments, the nucleic acid construct(s) comprise(s) at least one polynucleotide sequence encoding at least one xylose isomerase, and/or at least one xylitol dehydrogenase, and/or at least one xylulokinase, wherein the polynucleotide is selected from: (a) a polynucleotide that encodes a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:2, 8, 10, 12, 14, 16, 18, 20, 22, and/or 24; a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:4; and a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:6; and (b) a polynucleotide that hybridizes under stringent hybridization conditions to the complement of a polynucleotide that encodes a polypeptide having the amino acid sequence of SEQ ID NO:2, 4, 6, 8, 10, 12, 14, 16, 18, 20, 22, and/or 24. In some additional embodiments, the nucleic acid construct(s) comprise(s) at least one polynucleotide sequence encoding at least one xylose isomerase, at least one xylitol dehydrogenase, and/or at least one xylulokinase, wherein the polynucleotide is selected from: (a) a polynucleotide that encodes a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:2, 8, 10, 12, 14, 16, 18, 20, 22, and/or 24; a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:6; and (b) a polynucleotide that hybridizes under stringent hybridization conditions to the complement of a polynucleotide that encodes a polypeptide having the amino acid sequence of SEQ ID NO:2, 4, 6, 8, 10, 12, 14, 16, 18, 20, 22, and/or 24. In some additional embodiments, the nucleic acid construct(s) comprise(s) at least one polynucleotide sequence encoding at least one xylose isomerase, and at least one xylitol dehydrogenase, and at least one xylulokinase, wherein the polynucleotide is selected from: (a) a polynucleotide that encodes a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:2, 8, 10, 12, 14, 16, 18, 20, 22, and/or 24; a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:4; and a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:6; and (b) a polynucleotide that hybridizes under stringent hybridization conditions to the complement of a polynucleotide that encodes a polypeptide having the amino acid sequence of SEQ ID NO:2, 4, 6, 8, 10, 12, 14, 16, 18, 20, 22, and/or 24. In some additional embodiments, the recombinant fungal host cell comprises at least one nucleic acid construct, wherein the nucleic acid construct comprises at least one polynucleotide encoding a xylose isomerase, at least one polynucleotide encoding a xylitol dehydrogenase, and/or at least one polynucleotide encoding a xylulokinase. In some additional embodiments, the recombinant fungal host cell comprises at least one nucleic acid construct, wherein the nucleic acid construct comprises at least one polynucleotide encoding a xylose isomerase, at least one polynucleotide encoding a xylitol dehydrogenase, and at least one polynucleotide encoding a xylulokinase. In some embodiments, the nucleic acid construct(s) comprise(s) at least one polynucleotide sequence encoding at least one xylose isomerase, and/or at least one xylitol dehydrogenase, and/or at least one xylulokinase, wherein the polynucleotide is selected from: (a) a polynucleotide that encodes a polypeptide comprising an amino acid sequence having at least 70%, least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:2, 8, 10, 12, 14, 16, 18, 20, 22, and/or 24; a polypeptide comprising an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:4; a polypeptide comprising an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:6; and (b) a polynucleotide that hybridizes under stringent hybridization conditions to the complement of a polynucleotide that encodes a polypeptide having the amino acid sequence of SEQ ID NO:2, 4, 6, 8, 10, 12, 14, 16, 18, 20, 22, and/or 24. In some embodiments, the nucleic acid construct(s) comprise(s) at least one polynucleotide sequence encoding at least one xylose isomerase, at least one xylitol dehydrogenase, and/or at least one xylulokinase, wherein the polynucleotide is selected from: (a) a polynucleotide that encodes a polypeptide comprising an amino acid sequence having at least 70%, least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:2, 8, 10, 12, 14, 16, 18, 20, 22, and/or 24; a polypeptide comprising an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:6; and (b) a polynucleotide that hybridizes under stringent hybridization conditions to the complement of a polynucleotide that encodes a polypeptide having the amino acid sequence of SEQ ID NO:2, 4, 6, 8, 10, 12, 14, 16, 18, 20, 22, and/or 24. In some embodiments, the nucleic acid construct(s) comprise(s) at least one polynucleotide sequence encoding at least one xylose isomerase, at least one xylitol dehydrogenase, and at least one xylulokinase, wherein the polynucleotide is selected from: (a) a polynucleotide that encodes a polypeptide comprising an amino acid sequence having at least 70%, least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:2, 8, 10, 12, 14, 16, 18, 20, 22, and/or 24; a polypeptide comprising an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:4; a polypeptide comprising an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:6; and (b) a polynucleotide that hybridizes under stringent hybridization conditions to the complement of a polynucleotide that encodes a polypeptide having the amino acid sequence of SEQ ID NO:2, 4, 6, 8, 10, 12, 14, 16, 18, 20, 22, and/or 24. In some embodiments, the host cell is a yeast cell. In some further embodiments, the host cell is *Saccharomyces cerevisiae*.

The present invention also provides recombinant nucleic acid constructs comprising at least one polynucleotide sequence encoding at least one xylose isomerase, and/or at least one xylitol dehydrogenase, and/or at least one xylulokinase. In some embodiments, the nucleic acid constructs comprise at least one polynucleotide sequence encoding at least one xylose isomerase, at least one xylitol dehydrogenase, and/or at least one xylulokinase. In some embodiments, the nucleic acid constructs comprise at least one polynucleotide sequence encoding at least one xylose isomerase, at least one xylitol dehydrogenase, and at least one xylulokinase. In some further embodiments, the present invention provides recombinant nucleic acid constructs comprising at least one polynucleotide sequence encoding at least one xylose isomerase, and/or at least one polynucleotide sequence encoding at least one xylitol dehydrogenase, and/or at least one polynucleotide sequence encoding at least one xylulokinase. In some further embodiments, the present invention provides recombinant nucleic acid constructs comprising at least one polynucleotide sequence encoding at least one xylose isomerase, at least one polynucleotide sequence encoding at least one xylitol dehydrogenase, and/or at least one polynucleotide sequence encoding at least one xylulokinase. In some further embodiments, the present invention provides recombinant nucleic acid constructs comprising at least one polynucleotide sequence encoding at least one xylose isomerase, at least one polynucleotide sequence encoding at least one xylitol dehydrogenase, and at least one polynucleotide sequence encoding at least one xylulokinase. In some embodiments, the xylose isomerase, and/or xylitol dehydrogenase, and/or xylulokinase are eukaryotic or prokaryotic enzymes. In some embodiments, the xylose isomerase, xylitol dehydrogenase, and/or xylulokinase are eukaryotic or prokaryotic enzymes. In some embodiments, the xylose isomerase, xylitol dehydrogenase, and xylulokinase are eukaryotic or prokaryotic enzymes. In some embodiments, the xylose isomerase, and/or xylitol dehydrogenase, and/or xylulokinase are eukaryotic enzymes. In some embodiments, the xylose isomerase, xylitol dehydrogenase, and/or xylulokinase are eukaryotic enzymes. In some embodiments, the xylose isomerase, xylitol dehydrogenase, and xylulokinase are eukaryotic enzymes. In some additional embodiments, the xylose isomerase, and/or xylitol dehydrogenase, and/or xylulokinase are fungal enzymes. In some additional embodiments, the xylose isomerase, xylitol dehydrogenase, and/or xylulokinase are fungal enzymes. In some additional embodiments, the xylose isomerase, xylitol dehydrogenase, and xylulokinase are fungal enzymes. In some further embodiments, the xylose isomerase, and/or xylitol dehydrogenase, and/or xylulokinase are yeast enzymes. In some further embodiments, the xylose isomerase, xylitol dehydrogenase, and/or xylulokinase are yeast enzymes. In some further embodiments, the xylose isomerase, xylitol dehydrogenase, and xylulokinase are yeast enzymes. In some additional embodiments, at least one nucleic acid construct further comprises at least one genetic element that facilitates stable integration into a fungal host genome. In some embodiments, the genetic element facilitates integration into a fungal host genome by homologous recombination. In some additional embodiments, the genetic element comprises a prokaryotic or eukaryotic origin of replication and/or a centromeric plasmid maintenance sequence. In some embodiments, the origin of replication and/or centromeric plasmid maintenance sequence is a fungal sequence. In some additional embodiments, the fungal origin of replication is a yeast origin of replication. In yet some additional embodiments, at least one of the polynucleotide sequences is operatively linked to a promoter sequence that is functional in a fungal cell. In some further embodiments, the promoter sequence is a fungal promoter sequence. In some embodiments, the fungal promoter sequence is a yeast promoter sequence. In some additional embodiments, the polynucleotide sequence is operatively linked to a transcription termination sequence that is functional in a fungal cell. In some more embodiments, the polynucleotide sequence contains codons optimized for expression in a yeast cell. In some additional embodiments, at least one polynucleotide sequence encoding at least one xylose isomerase is operatively linked to a promoter sequence, and/or at least one polynucleotide sequence encoding at least one xylitol dehydrogenase is operatively linked to a promoter sequence, and/or at least one polynucleotide sequence encoding at least one xylulokinase is operatively linked to a promoter sequence, wherein the promoter sequences are functional in a fungal host cell. In some additional embodiments, at least one polynucleotide sequence encoding at least one xylose isomerase is operatively linked to a promoter sequence, at least one polynucleotide sequence encoding at least one xylitol dehydrogenase is operatively linked to a promoter sequence, and/or at least one polynucleotide sequence encoding at least one xylulokinase is operatively linked to a promoter sequence, wherein the promoter sequences are functional in a fungal host cell. In some additional embodiments, at least one polynucleotide sequence encoding at least one xylose isomerase is operatively linked to a promoter sequence, at least one polynucleotide sequence encoding at least one xylitol dehydrogenase is operatively linked to a promoter sequence, and at least one polynucleotide sequence encoding at least one xylulokinase is operatively linked to a promoter sequence, wherein the promoter sequences are functional in a fungal host cell. In some embodiments, the promoter sequence(s) is/are fungal promoter sequence(s). In some embodiments, the fungal promoter sequence is a yeast promoter sequence. In some additional embodiments, the polynucleotide sequence is operatively linked to at least one transcription termination sequence that is functional in a fungal cell. In some further embodiments, the polynucleotide sequence contains codons optimized for expression in a yeast cell. In still some additional embodiments, the construct comprises at least one polynucleotide sequence encoding at least one xylose isomerase, at least one xylitol dehydrogenase, and at least one xylulokinase, wherein the polynucleotide is selected from: (a) a polynucleotide that encodes a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:2, 8, 10, 12, 14, 16, 18, 20, 22, and/or 24; a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:4; and a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:6; and (b) a polynucleotide that hybridizes under stringent hybridization conditions to the complement of a polynucleotide that encodes a polypeptide having the amino acid sequence of SEQ ID NO:2, 4, 6, 8, 10, 12, 14, 16, 18, 20, 22, and/or 24. In still some additional embodiments, the construct comprises at least one polynucleotide sequence encoding at least one xylose isomerase, and/or at least one xylitol dehydrogenase, and/or at least one xylulokinase, wherein the polynucleotide is selected from: (a) a polynucleotide that encodes a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:2, 8, 10, 12, 14, 16, 18, 20, 22, and/or 24; a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:4; and a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:6; and (b) a polynucleotide that hybridizes under stringent hybridization conditions to the complement of a polynucleotide that encodes a polypeptide having the amino acid sequence of SEQ ID NO:2, 4, 6, 8, 10, 12, 14, 16, 18, 20, 22, and/or 24. In some additional embodiments, the construct comprises at least one polynucleotide sequence encoding at least one xylose isomerase, at least one xylitol dehydrogenase, and/or at least one xylulokinase, wherein the polynucleotide is selected from: (a) a polynucleotide that encodes a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:2, 8, 10, 12, 14, 16, 18, 20, 22, and/or 24; a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:4; and a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:6; and (b) a polynucleotide that hybridizes under stringent hybridization conditions to the complement of a polynucleotide that encodes a polypeptide having the amino acid sequence of SEQ ID NO:2, 4, 6, 8, 10, 12, 14, 16, 18, 20, 22, and/or 24. In some further embodiments, the nucleic acid construct comprises at least one polynucleotide sequence encoding at least one xylose isomerase, and/or at least one xylitol dehydrogenase, and/or at least one xylulokinase, wherein the polynucleotide is selected from: (a) a polynucleotide that encodes a polypeptide comprising an amino acid sequence having at least 70%, least 71%, at least 72%, at least 73%, at least 74%, at least 75%, at least 76%, at least 77%, at least 78%, at least 79%, at least 80%, at least 81%9, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:2, 8, 10, 12, 14, 16, 18, 20, 22, and/or 24; a polypeptide comprising an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:4; a polypeptide comprising an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:6; and (b) a polynucleotide that hybridizes under stringent hybridization conditions to the complement of a polynucleotide that encodes a polypeptide having the amino acid sequence of SEQ ID NO:2, 4, 6, 8, 10, 12, 14, 16, 18, 20, 22, and/or 24. In some other embodiments, the nucleic acid construct comprises at least one polynucleotide sequence encoding at least one xylose isomerase, at least one xylitol dehydrogenase, and/or at least one xylulokinase, wherein the polynucleotide is selected from: (a) a polynucleotide that encodes a polypeptide comprising an amino acid sequence having at least 70%, % least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:2, 8, 10, 12, 14, 16, 18, 20, 22, and/or 24; a polypeptide comprising an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:4; a polypeptide comprising an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:6; and (b) a polynucleotide that hybridizes under stringent hybridization conditions to the complement of a polynucleotide that encodes a polypeptide having the amino acid sequence of SEQ ID NO:2, 4, 6, 8, 10, 12, 14, 16, 18, 20, 22, and/or 24. In some embodiments, the nucleic acid construct comprises at least one polynucleotide sequence encoding at least one xylose isomerase, at least one xylitol dehydrogenase, and at least one xylulokinase, wherein the polynucleotide is selected from: (a) a polynucleotide that encodes a polypeptide comprising an amino acid sequence having at least 70%, % least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:2, 8, 10, 12, 14, 16, 18, 20, 22, and/or 24; a polypeptide comprising an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:4; a polypeptide comprising an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:6; and (b) a polynucleotide that hybridizes under stringent hybridization conditions to the complement of a polynucleotide that encodes a polypeptide having the amino acid sequence of SEQ ID NO:2, 4, 6, 8, 10, 12, 14, 16, 18, 20, 22, and/or 24. In some additional embodiments, at least one polynucleotide sequence encodes at least one xylose isomerase, at least one xylitol dehydrogenase, and at least one xylulokinase, wherein the polynucleotide comprises at least one sequence selected from SEQ ID NOS:1, 7, 9, 11, 13, 15, 17, 19, 21, and 23; SEQ ID NO:3, and SEQ ID NO:5. In some additional embodiments, any of the constructs described above further comprises a polynucleotide sequence encoding at least one xylose reductase.

The present invention also provides recombinant nucleic acid constructs comprising at least one polynucleotide sequence encoding at least one xylose isomerase. In some embodiments, the xylose isomerase is a eukaryotic or prokaryotic enzyme, while in some alternative embodiments, the xylose isomerase is a eukaryotic enzyme. In some embodiments, the xylose isomerase is a *G. trabeum* xylose isomerase, an *Orpinomyces* xylose isomerase, a xylose isomerase obtained from a bovine rumen, a xylose isomerase obtained from a human gut, a *C. boidinii* xylose isomerase, *P. infestans* xylose isomerase, or *B. hominis* xylose isomerase. In some additional embodiments, at least one nucleic acid construct further comprises at least one genetic element that facilitates stable integration into a fungal host genome. In some embodiments, the genetic element facilitates integration into a fungal host genome by homologous recombination. In some additional embodiments, the genetic element comprises a prokaryotic or eukaryotic origin of replication and/or a centromeric plasmid maintenance sequence. In some embodiments, the origin of replication and/or centromeric plasmid maintenance sequence is a fungal sequence. In some additional embodiments, the fungal origin of replication is a yeast origin of replication. In yet some additional embodiments, at least one of the polynucleotide sequences is operatively linked to a promoter sequence that is functional in a fungal cell. In some further embodiments, the promoter sequence is a fungal promoter sequence. In some embodiments, the fungal promoter sequence is a yeast promoter sequence. In some additional embodiments, the polynucleotide sequence is operatively linked to a transcription termination sequence that is functional in a fungal cell. In some more embodiments, the polynucleotide sequence contains codons optimized for expression in a yeast cell. In some further embodiments, at least one polynucleotide is integrated into the host cell genome. In yet some additional embodiments, the host cell has had one or more native genes deleted from its genome. In some embodiments, the deletion of one or more native gene results in one or more phenotypes selected from increased transport of xylose into the host cell, increased xylulokinase activity, increased xylitol dehydrogenase activity, increased xylose isomerase activity, increased xylose reductase activity, increased flux through the pentose phosphate pathway, decreased sensitivity to catabolite repression, increased tolerance to ethanol, increased tolerance to acetate, increased tolerance to increased osmolarity, increased tolerance to low pH, and reduced production of by products, wherein comparison is made with respect to the corresponding host cell without the deletion(s). In some further embodiments, the host cell is altered to overexpress one or more polynucleotides. In some embodiments, the overexpression results in one or more phenotypes selected from increased transport of xylose into the host cell, increased xylulokinase activity, increased xylitol dehydrogenase activity, increased xylose isomerase activity, increased xylose reductase activity, increased flux through the pentose phosphate pathway, decreased sensitivity to catabolite repression, increased tolerance to ethanol, increased tolerance to acetate, increased tolerance to increased osmolarity, increased tolerance to low pH, and reduced product of by products, wherein comparison is made to the corresponding unaltered host cell. In some embodiments, the nucleic acid construct(s) comprise(s) at least one polynucleotide sequence comprising at least one sequence selected from SEQ ID NOS:1, 7, 9, 11, 13, 15, 17, 19, 21, and 23; SEQ ID NO:3; and SEQ ID NO:5. In some additional embodiments, the host cell is a yeast cell. In some further embodiments, the host cell is *Saccharomyces cerevisiae*. In some embodiments, the nucleic acid construct comprises at least one polynucleotide sequence encoding at least one xylose isomerase, wherein the polynucleotide is selected from: (a) a polynucleotide that encodes a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:8, 10, 12, 14, 16, 18, 20, 22, and/or 24; and (b) a polynucleotide that hybridizes under stringent hybridization conditions to the complement of a polynucleotide that encodes a polypeptide having the amino acid sequence of SEQ ID NO:8, 10, 12, 14, 16, 18, 20, 22, and/or 24. In some additional embodiments, the nucleic acid construct comprises at least one polynucleotide sequence encoding at least one xylose isomerase, wherein the polynucleotide is selected from: (a) a polynucleotide that encodes a polypeptide comprising an amino acid sequence having at least 70%, % least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:8, 10, 12, 14, 16, 18, 20, 22, and/or 24; and (b) a polynucleotide that hybridizes under stringent hybridization conditions to the complement of a polynucleotide that encodes a polypeptide having the amino acid sequence of SEQ ID NO:8, 10, 12, 14, 16, 18, 20, 22, and/or 24. In some embodiments, the nucleic acid construct(s) comprise at least one polynucleotide sequence comprising at least one sequence selected from SEQ ID NOS:7, 9, 11, 13, 15, 17, 19, 21, and/or 23. In some additional embodiments, the nucleic acid construct(s) comprise(s) at least one polynucleotide sequence encoding at least one xylose isomerase, and/or at least one xylitol dehydrogenase, and/or at least one xylulokinase, wherein the polynucleotide is selected from: (a) a polynucleotide that encodes a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:2, 8, 10, 12, 14, 16, 18, 20, 22, and/or 24; a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:4; and a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 1000% identity to SEQ ID NO:6; and (b) a polynucleotide that hybridizes under stringent hybridization conditions to the complement of a polynucleotide that encodes a polypeptide having the amino acid sequence of SEQ ID NO:2, 4, 6, 8, 10, 12, 14, 16, 18, 20, 22, and/or 24. In some additional embodiments, the nucleic acid construct(s) comprise(s) at least one polynucleotide sequence encoding at least one xylose isomerase, at least one xylitol dehydrogenase, and/or at least one xylulokinase, wherein the polynucleotide is selected from: (a) a polynucleotide that encodes a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:2, 8, 10, 12, 14, 16, 18, 20, 22, and/or 24; a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:4; and a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:6; and (b) a polynucleotide that hybridizes under stringent hybridization conditions to the complement of a polynucleotide that encodes a polypeptide having the amino acid sequence of SEQ ID NO:2, 4, 6, 8, 10, 12, 14, 16, 18, 20, 22, and/or 24. In some additional embodiments, the nucleic acid construct(s) comprise(s) at least one polynucleotide sequence encoding at least one xylose isomerase, and at least one xylitol dehydrogenase, and at least one xylulokinase, wherein the polynucleotide is selected from: (a) a polynucleotide that encodes a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:2, 8, 10, 12, 14, 16, 18, 20, 22, and/or 24; a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:4; and a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:6; and (b) a polynucleotide that hybridizes under stringent hybridization conditions to the complement of a polynucleotide that encodes a polypeptide having the amino acid sequence of SEQ ID NO:2, 4, 6, 8, 10, 12, 14, 16, 18, 20, 22, and/or 24. In some additional embodiments, the recombinant fungal host cell comprises at least one nucleic acid construct, wherein the nucleic acid construct comprises at least one polynucleotide encoding a xylose isomerase, at least one polynucleotide encoding a xylitol dehydrogenase, and/or at least one polynucleotide encoding a xylulokinase. In some embodiments, the construct comprises at least one polynucleotide sequence encoding at least one xylose isomerase, wherein the polynucleotide is selected from: (a) a polynucleotide that encodes a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:8, 10, 12, 14, 16, 18, 20, 22, and/or 24; and (b) a polynucleotide that hybridizes under stringent hybridization conditions to the complement of a polynucleotide that encodes a polypeptide having the amino acid sequence of SEQ ID NO:8, 10, 12, 14, 16, 18, 20, 22, and/or 24. In some further embodiments, the nucleic acid construct comprises at least one polynucleotide sequence encoding at least one xylose isomerase, wherein the polynucleotide that encodes a polypeptide comprising an amino acid sequence having at least 70%, % least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:8, 10, 12, 14, 16, 18, 20, 22, and/or 24; and (b) a polynucleotide that hybridizes under stringent hybridization conditions to the complement of a polynucleotide that encodes a polypeptide having the amino acid sequence of SEQ ID NO:8, 10, 12, 14, 16, 18, 20, 22, and/or 24. In some additional embodiments, at least one polynucleotide sequence encodes at least one xylose isomerase, wherein the polynucleotide comprises at least one sequence selected from SEQ ID NOS:7, 9, 11, 13, 15, 17, 19, 21, and 23. In some further embodiments, the nucleic acid construct comprises at least one polynucleotide encoding a xylose isomerase, at least one polynucleotide encoding a xylitol dehydrogenase, and at least one polynucleotide encoding a xylulokinase. In some embodiments, the nucleic acid construct(s) comprise(s) at least one polynucleotide sequence encoding at least one xylose isomerase, and/or at least one xylitol dehydrogenase, and/or at least one xylulokinase, wherein the polynucleotide is selected from: (a) a polynucleotide that encodes a polypeptide comprising an amino acid sequence having at least 70%, % least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:2, 8, 10, 12, 14, 16, 18, 20, 22, and/or 24; a polypeptide comprising an amino acid sequence having at least 70%, at least 71%, at least 72%, at least 73%, at least 74%, at least 75%, at least 76%, at least 77, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:4; a polypeptide comprising an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:6; and (b) a polynucleotide that hybridizes under stringent hybridization conditions to the complement of a polynucleotide that encodes a polypeptide having the amino acid sequence of SEQ ID NO:2, 4, 6, 8, 10, 12, 14, 16, 18, 20, 22, and/or 24. In some embodiments, the nucleic acid construct(s) comprise(s) at least one polynucleotide sequence encoding at least one xylose isomerase, at least one xylitol dehydrogenase, and/or at least one xylulokinase, wherein the polynucleotide is selected from: (a) a polynucleotide that encodes a polypeptide comprising an amino acid sequence having at least 70%. % least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:2, 8, 10, 12, 14, 16, 18, 20, 22, and/or 24; a polypeptide comprising an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:4; a polypeptide comprising an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:6; and (b) a polynucleotide that hybridizes under stringent hybridization conditions to the complement of a polynucleotide that encodes a polypeptide having the amino acid sequence of SEQ ID NO:2, 4, 6, 8, 10, 12, 14, 16, 18, 20, 22, and/or 24. In some embodiments, the nucleic acid construct(s) comprise(s) at least one polynucleotide sequence encoding at least one xylose isomerase, at least one xylitol dehydrogenase, and at least one xylulokinase, wherein the polynucleotide is selected from: (a) a polynucleotide that encodes a polypeptide comprising an amino acid sequence having at least 70%, % least 71%, at least 72%, at least 73%, at least 74%, at least 75%, at least 76%, at least 77%, at least 78%, at least 79%, at least 80%, at least 81%, at least 82%, at least 83%, at least 849%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:2, 8, 10, 12, 14, 16, 18, 20, 22, and/or 24; a polypeptide comprising an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:4; a polypeptide comprising an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 929%, at least 93%, at least 94%, at least 95%, at least 96%, at least 97%, at least 98%, at least 99%, or at least 100% identity to SEQ ID NO:6; and (b) a polynucleotide that hybridizes under stringent hybridization conditions to the complement of a polynucleotide that encodes a polypeptide having the amino acid sequence of SEQ ID NO:2, 4, 6, 8, 10, 12, 14, 16, 18, 20, 22, and/or 24. In some embodiments, the host cell is a yeast cell. In some further embodiments, the host cell is *Saccharomyces cerevisiae*.

The present invention also provides isolated polypeptide sequences comprising a xylose isomerase polypeptide, and/or xylitol dehydrogenase polypeptide, and/or xylulokinase polypeptide. The present invention also provides isolated polypeptide sequences comprising at least one xylose isomerase polypeptide, and/or at least one xylitol dehydrogenase polypeptide, and/or at least one xylulokinase polypeptide. The present invention also provides isolated polypeptide sequences comprising at least one xylose isomerase polypeptide, at least one xylitol dehydrogenase polypeptide, and/or at least one xylulokinase polypeptide. In some embodiments, the xylose isomerase polypeptide comprises an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:2, 8, 10, 12, 14, 16, 18, 20, 22, and/or 24; the xylitol dehydrogenase polypeptide comprises an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:4; and the xylulokinase polypeptide comprises an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:6. In some further embodiments, the xylose isomerase polypeptide comprises an amino acid sequence having at least 70%, % least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:2, 8, 10, 12, 14, 16, 18, 20, 22, and/or 24; the xylitol dehydrogenase polypeptide comprises an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:4; and the xylulokinase polypeptide comprises an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:6. In some additional embodiments, the xylose isomerase polypeptide comprises an amino acid sequence encoded by a polynucleotide sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:1, 7, 9, 12, 3, 15, 17, 19, 21, and/or 23; the xylitol dehydrogenase polypeptide comprises an amino acid sequence encoded by a polynucleotide sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:3; and the xylulokinase polypeptide comprises an amino acid sequence encoded by a polynucleotide sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:5. In some further embodiments, the xylose isomerase polypeptide comprises an amino acid sequence encoded by a polynucleotide sequence having at least 70%, % least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:1, 7, 9, 11, 13, 15, 17, 19, 21, and/or 23; the xylitol dehydrogenase polypeptide comprises an amino acid sequence encoded by a polynucleotide sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:3; and the xylulokinase polypeptide comprises an amino acid sequence encoded by a polynucleotide sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:5. In still some additional embodiments, the xylose isomerase polypeptide is encoded by a polynucleotide sequence selected from SEQ ID NOS:1, 7, 9, 11, 13, 15, 17, 19, 21, and/or 23; the xylitol dehydrogenase polypeptide is encoded by SEQ ID NO:3; and the xylulokinase is encoded by SEQ ID NO:5.

The present invention further provides isolated polynucleotide sequences comprising a xylose isomerase polynucleotide, xylitol dehydrogenase polypeptide, and xylulokinase polypeptide. In some embodiments, the isolated polynucleotide sequences comprise at least one xylose isomerase polynucleotide, and/or at least one xylitol dehydrogenase polypeptide, and/or at least one xylulokinase polypeptide. In some further embodiments, the isolated polynucleotide sequences comprise at least one xylose isomerase polynucleotide, at least one xylitol dehydrogenase polypeptide, and/or at least one xylulokinase polypeptide. In some other embodiments, the isolated polynucleotide sequences comprise at least one xylose isomerase polynucleotide, at least one xylitol dehydrogenase polypeptide, and at least one xylulokinase polypeptide. In some additional embodiments, the xylose isomerase polynucleotide sequence has at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:1, 7, 9, 12, 3, 15, 17, 19, 21, and/or 23; and/or the xylitol dehydrogenase polynucleotide sequence has at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:3; and/or the xylulokinase polynucleotide sequence has at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:5. In some further embodiments, the xylose isomerase polynucleotide sequence has at least about 70%, at least about 71%, at least about 72%, at least about 73%, at least about 74%, at least about 75%, at least about 76%, at least about 77%, at least about 789%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:1, 7, 9, 12, 3, 15, 17, 19, 21, and/or 23; the xylitol dehydrogenase polynucleotide sequence has at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:3; and/or the xylulokinase polynucleotide sequence has at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:5. In still some additional embodiments, the xylose isomerase polynucleotide sequence has at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:1, 7, 9, 12, 3, 15, 17, 19, 21, and/or 23; the xylitol dehydrogenase polynucleotide sequence has at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:3; and the xylulokinase polynucleotide sequence has at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:5. In some embodiments, the xylose isomerase polypeptide comprises an amino acid sequence encoded by a polynucleotide sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:1, 7, 9, 11, 13, 15, 17, 19, 21, and/or 23; and/or the xylitol dehydrogenase polypeptide comprises an amino acid sequence encoded by a polynucleotide sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:3; and/or the xylulokinase polypeptide comprises an amino acid sequence encoded by a polynucleotide sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:5. In some embodiments, the xylose isomerase polypeptide comprises an amino acid sequence encoded by a polynucleotide sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:1, 7, 9, 11, 13, 15, 17, 19, 21, and/or 23; the xylitol dehydrogenase polypeptide comprises an amino acid sequence encoded by a polynucleotide sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:3; and/or the xylulokinase polypeptide comprises an amino acid sequence encoded by a polynucleotide sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:5. In some embodiments, the xylose isomerase polypeptide comprises an amino acid sequence encoded by a polynucleotide sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:1, 7, 9, 11, 13, 15, 17, 19, 21, and/or 23; the xylitol dehydrogenase polypeptide comprises an amino acid sequence encoded by a polynucleotide sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:3; and the xylulokinase polypeptide comprises an amino acid sequence encoded by a polynucleotide sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:5. In some further embodiments, the xylose isomerase polynucleotide sequence is selected from SEQ ID NOS:1, 7, 9, 11, 13, 15, 17, 19, 21, and/or 23; and/or the xylitol dehydrogenase polynucleotide sequence is SEQ ID NO:3; and/or the xylulokinase polynucleotide sequence is SEQ ID NO:5. In some further embodiments, the xylose isomerase polynucleotide sequence is selected from SEQ ID NOS:1, 7, 9, 11, 13, 15, 17, 19, 21, and/or 23; the xylitol dehydrogenase polynucleotide sequence is SEQ ID NO:3; and/or the xylulokinase polynucleotide sequence is SEQ ID NO:5. In some further embodiments, the xylose isomerase polynucleotide sequence is selected from SEQ ID NOS:1, 7, 9, 11, 13, 15, 17, 19, 21, and/or 23; the xylitol dehydrogenase polynucleotide sequence is SEQ ID NO:3; and the xylulokinase polynucleotide sequence is SEQ ID NO:5. In some additional embodiments, the xylose isomerase polynucleotide sequence encodes an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:2, 8, 10, 12, 14, 16, 18, 20, 22, and/or 24; and/or the xylitol dehydrogenase polynucleotide encodes an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:4; and/or the xylulokinase polynucleotide encodes an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:6. In some additional embodiments, the xylose isomerase polynucleotide sequence encodes an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:2, 8, 10, 12, 14, 16, 18, 20, 22, and/or 24; the xylitol dehydrogenase polynucleotide encodes an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:4; and the xylulokinase polynucleotide encodes an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:6. In some further embodiments, the xylose isomerase polynucleotide sequence encodes an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:2, 8, 10, 12, 14, 16, 18, 20, 22, and/or 24; and/or the xylitol dehydrogenase polynucleotide encodes an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:4; and/or the xylulokinase polynucleotide encodes an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:6. In some further embodiments, the xylose isomerase polynucleotide sequence encodes an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:2, 8, 10, 12, 14, 16, 18, 20, 22, and/or 24; the xylitol dehydrogenase polynucleotide encodes an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:4; and the xylulokinase polynucleotide encodes an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:6. In some additional embodiments, the xylose isomerase polynucleotide sequence encodes an amino acid sequence selected from SEQ ID NOS:2, 8, 10, 12, 14, 16, 18, 20, 22, and/or 24; and/or the xylitol dehydrogenase polynucleotide sequence encodes the amino acid sequence set forth in SEQ ID NO:4; and/or the xylulokinase polynucleotide sequence encodes the amino acid sequence set forth in SEQ ID NO:6. In some additional embodiments, the xylose isomerase polynucleotide sequence encodes an amino acid sequence selected from SEQ ID NOS:2, 8, 10, 12, 14, 16, 18, 20, 22, and/or 24; the xylitol dehydrogenase polynucleotide sequence encodes the amino acid sequence set forth in SEQ ID NO:4; and/or the xylulokinase polynucleotide sequence encodes the amino acid sequence set forth in SEQ ID NO:6. In some additional embodiments, the xylose isomerase polynucleotide sequence encodes an amino acid sequence selected from SEQ ID NOS:2, 8, 10, 12, 14, 16, 18, 20, 22, and/or 24; the xylitol dehydrogenase polynucleotide sequence encodes the amino acid sequence set forth in SEQ ID NO:4; and the xylulokinase polynucleotide sequence encodes the amino acid sequence set forth in SEQ ID NO:6.

The present invention also provides methods for producing a fermentation product, comprising: providing a recombinant fungal host cell as provided herein; providing a fermentation medium; and contacting the fermentation medium with the recombinant fungal host cell under conditions suitable for generating the fermentation product. In some embodiments, the methods further comprise the step of recovering the fermentation product. In some additional embodiments, the fermenting step is carried out under conditions selected from anaerobic, microaerobic or aerobic conditions. In some further embodiments, the fermentation product is selected from an alcohol, a fatty alcohol, a fatty acid, lactic acid, acetic acid, 3-hydroxypropionic acid, acrylic acid, succinic acid, citric acid, malic acid, fumaric acid, succinic acid, an amino acid, 1,3-propanediol, ethylene, glycerol, and a β-lactam. In some still additional embodiments, the fermentation product is an alcohol selected from ethanol and butanol. In some embodiments, the fermentation product is ethanol. In some embodiments, the fermentation medium comprises product from a saccharification process. In some further embodiments, the fermentation medium comprises hemicellulosic feedstock.

The present invention also provides methods of producing at least one end product from at least one cellulosic substrate, comprising: providing at least one cellulosic substrate and at least one enzyme composition comprising at least one cellulase; contacting the cellulosic substrate with the enzyme composition under conditions whereby fermentable sugars are produced from the cellulosic substrate in a saccharification reaction; and contacting the fermentable sugars with a microorganism under fermentation conditions such that at least one end product is produced. In some embodiments, the methods comprise simultaneous saccharification and fermentation reactions (SSF), while in some alternative embodiments, the methods comprise saccharification of the cellulosic substrate and the fermentation in separate reactions (SHF). In some further embodiments, the enzyme composition is produced simultaneously with the saccharification reaction and the fermentation. In some embodiments, the methods further comprise at least one adjunct composition in the saccharification reaction. In some additional embodiments, the adjunct composition is selected from at least one divalent metal cation, copper, gallic acid, and/or at least one surfactant. In some further embodiments, the methods are conducted at about pH 5.0, while in some alternative embodiments, the methods are conducted at about pH 6.0. In some further embodiments, the methods further comprise recovering at least one end product. In some embodiments, the end product comprises at least one fermentation end product. In some additional embodiments, the fermentation end product is selected from alcohols, fatty acids, lactic acid, acetic acid, 3-hydroxypropionic acid, acrylic acid, succinic acid, citric acid, malic acid, fumaric acid, an amino acid, 1,3-propanediol, ethylene, glycerol, fatty alcohols, butadiene, and beta-lactams. In still some other embodiments, the fermentation end product is at least one alcohol selected from ethanol and butanol. In some embodiments, the alcohol is ethanol. In some additional embodiments, the microorganism is a yeast. In some embodiments, the yeast is *Saccharomyces*. In some additional embodiments, the methods further comprise recovering at least one fermentation end product.

DESCRIPTION OF THE FIGURES

FIG. 2A illustrates the pentose phosphate pathway (PPP). The substrates and products are shown. The enzymes are represented by numbers as follows: 6. Ribulose-5-phosphate 3-epimerase; 7. Transketolase (TKL1); 8. Transaldolase (TAL1); 9. Ribose-5-phosphate ketoisomerase (RKI1); 10. 6-phosphogluconate dehydrogenase (GND1); 11. 6-phosphogluconalactonase (SOL3); and 12. Glucose-6-phosphate-1-dehydrogenase (ZWF).

FIG. 2B illustrates the pathway of glycolysis. The substrates and products are shown. The enzymes are represented by numbers as follows: 13. Hexokinase; 14. Phosphoglucose isomerase; 15. Phosphofructokinase; 16. Aldolase; 17. Triose phosphate isomerase; 18. Glyceraldehyde 3-phosphate dehydrogenase; 19. 3-Phosphoglycerate kinase; 20. Phosphoglyceromutase; 21. Enolase; and 22. Pyruvate kinase.

FIG. 2C illustrates the metabolic pathway for converting pyruvate to ethanol. The substrates and products are shown. The enzymes are represented by numbers as follows: 23. Pyruvate decarboxylase; 24. Aldehyde dehydrogenase; and 25. Alcohol dehydrogenase.

DESCRIPTION OF THE INVENTION

Figure 1:
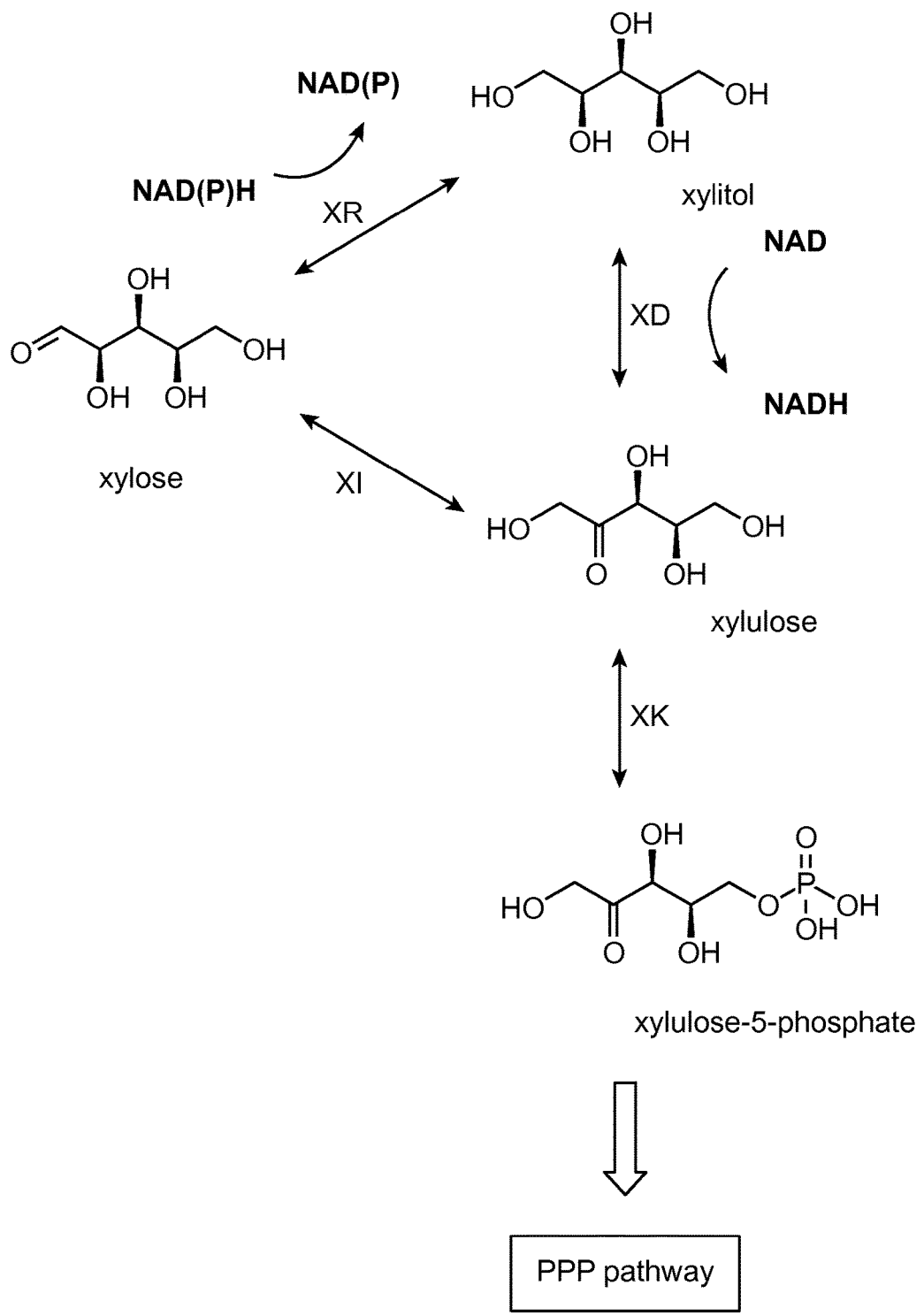
FIG. 1 illustrates xylose conversion pathways. In yeast and filamentous fungi, D-xylose is initially reduced to xylitol by NAD(P)H-dependent xylose reductase ("XR"). Xylitol is subsequently oxidized to D-xylulose by NAD+-dependent xylitol dehydrogenase ("XDH" or "XD"). Xylulokinase ("XK") subsequently phosphorylates D-xylulose to produce D-xylulose 5-phosphate, which is then further metabolized through the pentose phosphate pathway ("PPP"). In bacteria, D-xylose is directly converted to D-xylulose by a xylose isomerase ("XI").

The present invention provides methods and compositions suitable for use in the isomerization of xylose to xylulose, as well as methods and compositions suitable for use in the conversion of xylose to xylitol and xylulose, including nucleic acid constructs, recombinant fungal host cells, and related materials.

All patents and publications, including all sequences disclosed within such patents and publications, referred to herein are expressly incorporated by reference. Unless otherwise indicated, the practice of the present invention involves conventional techniques commonly used in molecular biology, fermentation, microbiology, and related fields, which are known to those of skill in the art. Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, some preferred methods and materials are described. Indeed, it is intended that the present invention not be limited to the particular methodology, protocols, and reagents described herein, as these may vary, depending upon the context in which they are used. The headings provided herein are not limitations of the various aspects or embodiments of the present invention.

In order to facilitate understanding of the present invention, a number of terms are defined below. Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

As used herein, the term "comprising" and its cognates are used in their inclusive sense (i.e., equivalent to the term "including" and its corresponding cognates).

As used herein and in the appended claims, the singular "a", "an" and "the" include the plural reference unless the context clearly dictates otherwise. Thus, for example, reference to a "host cell" includes a plurality of such host cells.

Unless otherwise indicated, nucleic acids are written left to right in 5' to 3' orientation; amino acid sequences are written left to right in amino to carboxy orientation, respectively. The headings provided herein are not limitations of the various aspects or embodiments of the invention that can be had by reference to the specification as a whole. Accordingly, the terms defined below are more fully defined by reference to the specification as a whole.

As used herein, the terms "isolated" and "purified" are used to refer to a molecule (e.g., an isolated nucleic acid, polypeptide, etc.) or other component that is removed from at least one other component with which it is naturally associated.

As used herein, the term "reference enzyme" refers to an enzyme to which another enzyme (i.e., the "test enzyme") is compared in order to determine the presence of an improved property in the test enzyme being evaluated, including but not limited to improved activity, thermoactivity, thermostability, and/or stability. In some embodiments, a reference enzyme is a wild-type enzyme (e.g., wild-type xylose isomerase, xylitol dehydrogenase, or xylulokinase). In some embodiments, a reference enzyme is another variant enzyme (e.g., another variant xylose isomerase, xylitol dehydrogenase enzyme, or xylulokinase of the present invention).

As used herein, the term "recombinant" refers to a polynucleotide or polypeptide that does not naturally occur in a host cell. A recombinant molecule may contain two or more naturally-occurring sequences that are linked together in a way that does not naturally occur. A "recombinant cell" comprises a recombinant polynucleotide or polypeptide.

As used herein, the term "overexpress" is intended to encompass increasing the production (i.e., expression) of a protein to a level greater than the cell normally produces. It is intended that the term encompass overexpression of endogenous, as well as heterologous proteins.

As used herein "parent" refers to a starting cell, gene or protein. In some embodiments, "parental strains" are used as the starting point to develop additional strains (e.g., derivatives). In some additional embodiments, "parental molecules" (e.g., "parental enzymes") are used as starting points for evolution/modification to produce variant molecules (e.g., "variant enzymes"). For clarity, reference to a cell of a particular strain refers to a parental cell of the strain as well as progeny and genetically modified derivatives of the same. Genetically modified derivatives of a parental cell include progeny cells that contain a modified genome or episomal plasmids that confer for example, antibiotic resistance, improved fermentation capability, the ability to utilize xylose as a carbon source, etc.

As used herein, in reference to a specific sequence, the term "modification" encompasses any alteration in a parent amino acid sequence, including but not limited to at least one substitution, deletion, and/or insertion, as well as any change to any component of the sequence. The term also encompasses any alteration in a parent nucleotide sequence, including but not limited to at least one substitution, deletion, insertion, and/or point mutation, etc., (e.g., any change to any component of the sequence). Thus, the term "modification" encompasses the term "mutation," in which a parent nucleotide and/or peptide sequence is altered through any means of mutagenesis.

A nucleic acid construct, nucleic acid (e.g., a polynucleotide), polypeptide, or host cell is referred to herein as "recombinant" when it is non-naturally occurring, artificial and/or engineered.

The terms "xylose isomerase" and "xylose isomerase polypeptide" are used interchangeably herein to refer to an enzyme that is capable of catalyzing the isomerization of D-xylose directly to D-xylulose. The ability to catalyze the isomerization of D-xylose directly to D-xylulose is referred to herein as "xylose isomerase activity".

The terms "xylitol dehydrogenase" and "xylitol dehydrogenase polypeptide" are used interchangeably herein to refer to an enzyme that is capable of catalyzing xylitol to xylulose. The ability to catalyze xylitol to xylulose is referred to herein as "xylitol dehydrogenase activity". Also, as used herein, the term "xylitol dehydrogenase polynucleotide" refers to a polynucleotide that encodes a xylitol dehydrogenase polypeptide.

The term "xylulokinase" refers to an enzyme that phosphorylates D-xylulose to produce D-xylulose 5-phosphate, which is then further metabolized through the pentose phosphate pathway.

For example, the term "xylose isomerase polynucleotide" refers to a polynucleotide that encodes a xylose isomerase polypeptide. The term "xylitol dehydrogenase polynucleotide" refers to a polynucleotide that encodes a xylitol dehydrogenase polypeptide. The term "xylulokinase polynucleotide" refers to a polynucleotide that encodes a xylulokinase polypeptide.

The terms "xylose reductase" and "xylose reductase polypeptide" are used interchangeably herein to refer to an enzyme that is capable of catalyzing xylose to xylitol. The ability to catalyze xylose to xylitol is referred to herein as "xylose reductase activity". The term "xylose reductase polynucleotide" refers to a polynucleotide that encodes a xylose reductase polypeptide.

The terms "protein" and "polypeptide" are used interchangeably herein to refer to a polymer of amino acid residues. As used herein, the terms "enzyme variant" and "variant enzyme" are used in reference to enzymes that are similar to a reference enzyme, particularly in their function, but have mutations in their amino acid sequence that make them different in sequence from the wild-type or another reference enzyme. Enzyme variants (e.g., "xylose reductase variants," "xylitol dehydrogenase variants," and/or "xylulokinase variants") can be made using any of a wide variety of different mutagenesis techniques well known to those skilled in the art. In addition, mutagenesis kits are also available from many commercial molecular biology suppliers. Methods are available to make specific substitutions at defined amino acids (site-directed), specific or random mutations in a localized region of the gene (regio-specific) or random mutagenesis over the entire gene (e.g., saturation mutagenesis). Numerous suitable methods are known to those in the art to generate enzyme variants, including but not limited to site-directed mutagenesis of single-stranded DNA or double-stranded DNA using PCR, cassette mutagenesis, gene synthesis, error-prone PCR shuffling, and chemical saturation mutagenesis, or any other suitable method known in the art. After the variants are produced, they can be screened for the desired property (e.g., high or increased; or low or reduced activity, increased thermal and/or alkaline stability, etc.).

As used herein, "combinatorial variant" refers to any variant that has a combination of two or more mutations (e.g., substitutions). In some embodiments, the combination of mutations results in changes in enzyme activity (e.g., improved thermostability, thermoactivity, and/or specific activity, etc.).

As used herein, the term "xylose isomerase variant" refers to a xylose isomerase that has been modified from an original starting xylose isomerase. In some embodiments, the term is used in reference to a xylose isomerase polypeptide or polynucleotide encoding a xylose isomerase polypeptide comprising one or more modifications relative to wild-type xylose isomerase or the wild-type polynucleotide encoding xylose isomerase (such as substitutions, insertions, deletions, and/or truncations of one or more amino acid residues or of one or more specific nucleotides or codons in the polypeptide or polynucleotide, respectively), and biologically active fragments thereof. In some embodiments, the xylose isomerase variants are xylose isomerase chimeras.

The terms "enzyme chimera," "chimeric variant," and "chimeric enzyme" refer to enzymes s that comprise sequences from at least two different parent molecules. In some embodiments, the chimeras are hybrid proteins encoded by nucleotide sequences that have been spliced together from at least two genes. It is not intended that the present invention be limited to any specific number of starting (i.e., "parental" sequences). In some embodiments, the term "chimeric" refers to a nucleic acid, nucleotide sequence and/or encoded product thereof, that contains sequences from two or more different sources. It is contemplated that any suitable source will find use in the present invention, including but not limited to nucleic acid, nucleotide sequence, ribosomal nucleic acid, RNA, DNA, regulatory nucleotide sequences (e.g., promoter, URL, enhancer, repressor, etc.), coding nucleic acid, gene, nucleic acid linker, nucleic acid tag, amino acid sequence, peptide, polypeptide, protein, chromosome, and/or organism. In some embodiments, "chimeric" molecules include sequences of contiguous nucleotides or amino acids from any suitable source, including but not limited to viruses, prokaryotes, and/or eukaryotes, etc. In some embodiments, chimeras are generated by placing fragments of related and/or unrelated nucleic acids, nucleotide sequences, and/or DNA segments in juxtaposition. In some embodiments, the nucleic acids, nucleotide sequences and/or DNA segments are native (e.g., wild-type) sequences, while in other embodiments, they are mutant and/or engineered (e.g., recombinant) sequences. It is not intended that the present invention be limited to any particular starting component. In some embodiments, the chimera comprises sequences (e.g., 1, 2, 3, 4, 5, 6, 7, 8, 9, or 10 sequences) from one organism and sequences (e.g., 1, 2, 3, 4, 5, 6, 7, 8, 9, or 10 sequences) from at least one other organism (e.g., as contiguous nucleotides or contiguous amino acids). In some embodiments, the organisms are microorganisms, including but not limited to bacteria, yeast, filamentous fungi, etc. In some embodiments, the sequences are obtained from at least two organisms of the same genus and/or species, but of different strains. In some other embodiments, the sequences are obtained from at least two organisms of the same species, while in some other embodiments, the sequence are obtained from at least two organisms of the same genus (i.e., different species). In some embodiments, the chimeras comprise a portion of an enzyme from one bacterial species and at least one additional portion of an enzyme from at least one additional bacterial species. In some embodiments, the chimeras comprise a portion of an enzyme from one fungal species and at least one additional portion of an enzyme from at least one additional fungal species. In some embodiments, the chimeras are comprised of sequences obtained from various types of organisms, for example combinations of bacterial and fungal species, as well as combinations of bacterial, fungal, viral, and/or plant species. Some embodiments of the present invention comprise one portion of an enzyme from a plant, another portion of an enzyme from a bacterium, and another portion of an enzyme from a fungus. Indeed, it is intended that any combination of parental organisms will find use in the present invention. In some embodiments, the chimeras are produced by recombination of two or more nucleotide sequences. Any suitable method for recombination finds use in producing the chimeras. In some embodiments, fragments used to generate chimeras are juxtaposed as units (e.g., nucleotide sequences from the various sources are combined end-to-end and are not interspersed). In some embodiments in which the chimeras include one stretch of contiguous nucleotides per each source organism, nucleotide sequence combinations can be noted as DNA source 1 (1DNA), DNA source 2 (2DNA), etc. (e.g., 1DNA/2DNA etc.), including combinations thereof. In some other embodiments, fragments used to generate the chimeras are interspersed (e.g., 1DNA/2DNA/4DNA/3DNA, etc.). In some embodiments, the chimeric nucleotide sequence encodes activity higher than any of the source nucleotide sequences. In some alternative embodiments, the chimeric nucleotide sequences have similar or same activity as the source nucleotide sequences, but the amount of the activity or kinetics of the activity (e.g., increased or decreased activity), specific activity, and/or other aspects of the activity are altered. In some additional embodiments, the chimeric nucleotide sequences encode different activities and in some further embodiments, the chimeric nucleotide sequences encode chimeric activities (e.g., a combination of two or more activities).

In some embodiments, xylose isomerase polynucleotides employed in the practice of the present invention comprise a polynucleotide sequence that is at least about 30%, at least about 35%, at least about 40%, at least about 45%, at least about 50%, at least about 55%, at least about 60%, at least about 65%, at least about 70%, at least about 71% identical, at least about 72% identical, at least about 73% identical, at least about 74% identical, at least about 75% identical, at least about 76% identical, at least about 77% identical, at least about 78% identical, at least about 79% identical, at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO:1, 7, 9, 11, 13, 15, 17, 19, 21, and/or 23, and/or a fragment of any of these sequences.

In some embodiments, xylitol dehydrogenase polynucleotides employed in the practice of the present invention comprise a polynucleotide sequence that is at least about 30%, at least about 35%, at least about 40%, at least about 45%, at least about 50%, at least about 55%, at least about 60%, at least about 65%, at least about 70% identical, at least about 71% identical, at least about 72% identical, at least about 73% identical, at least about 74% identical, at least about 75% identical, at least about 76% identical, at least about 77% identical, at least about 78% identical, at least about 79% identical, at least about 80% identical, at least about 81% identical, at least about 82% identical, at least about 83% identical, at least about 84% identical, at least about 85% identical, at least about 86% identical, at last about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO:3, and/or a fragment of any of these sequences.

In some embodiments, xylulokinase polynucleotides employed in the practice of the present invention comprise a polynucleotide sequence that is at least about 30%, at least about 35%, at least about 40%, at least about 45%, at least about 50%, at least about 55%, at least about 60%, at least about 65%, at least about 70% identical, at least about 71% identical, at least about 72% identical, at least about 73% identical, at least about 74% identical, at least about 75% identical, at least about 76% identical, at least about 77% identical, at least about 78% identical, at least about 79% identical, at least about 80% identical, at least about 81% identical, at least about 82% identical, at least about 83% identical, at least about 84% identical, at least about 85% identical, at least about 86% identical, at last about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO:5, and/or a fragment of any of these sequences.

In some embodiments, xylose isomerase polypeptides employed in the practice of the present invention comprise a polypeptide sequence that is at least about 30%, at least about 35%, at least about 40%, at least about 45%, at least about 50%, at least about 55%, at least about 60%, at least about 65%, at least about 70%, at least about 71% identical, at least about 72% identical, at least about 73% identical, at least about 74% identical, at least about 75% identical, at least about 76% identical, at least about 77% identical, at least about 78% identical, at least about 79% identical, at least about 80% identical, at least about 81% identical, at least about 82% identical, at least about 83% identical, at least about 84% identical, at least about 85% identical, at least about 86% identical, at least about 87% identical, at least about 88%, identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO:2, 8, 10, 12, 14, 16, 18, 20, 22, and/or 24, and/or a fragment of any of these sequences.

In some embodiments, xylitol dehydrogenase polypeptides employed in the practice of the present invention comprise a polypeptide sequence that is at least about 30%, at least about 35%, at least about 40%, at least about 45%, at least about 50%, at least about 55%, at least about 60%, at least about 65%, at least about 70% identical, at least about 71% identical, at least about 72% identical, at least about 73% identical, at least about 74% identical, at least about 75% identical, at least about 76% identical, at least about 77% identical, at least about 78% identical, at least about 79% identical, at least about 80% identical, at least about 81% identical, at least about 82% identical, at least about 83% identical, at least about 84% identical, at least about 85% identical, at least about 86% identical, at last about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO:4, and/or a fragment of any of these sequences.

In some embodiments, xylulokinase polypeptides employed in the practice of the present invention comprise a polypeptide sequence that is at least about 30%, at least about 35%, at least about 40%, at least about 45%, at least about 50%, at least about 55%, at least about 60%, at least about 65%, at least about 70% identical, at least about 71% identical, at least about 72% identical, at least about 73% identical, at least about 74% identical, at least about 75% identical, at least about 76% identical, at least about 77% identical, at least about 78% identical, at least about 79% identical, at least about 80% identical, at least about 81% identical, at least about 82% identical, at least about 83% identical, at least about 84% identical, at least about 85% identical, at least about 86% identical, at last about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO:6, and/or a fragment of any of these sequences.

The terms "percent identity," "% identity", "percent identical," and "% identical," are used interchangeably herein to refer to the percent amino acid or polynucleotide sequence identity that is obtained by ClustalW analysis (version W 1.8 available from European Bioinformatics Institute, Cambridge, UK), counting the number of identical matches in the alignment and dividing such number of identical matches by the length of the reference sequence, and using the following ClustalW parameters to achieve slow/accurate pairwise optimal alignments-DNA/Protein Gap Open Penalty: 15/10; DNA/Protein Gap Extension Penalty: 6.66/0.1 Protein weight matrix: Gonnet series; DNA weight matrix: Identity; Toggle Slow/Fast pairwise alignments=SLOW or FULL Alignment; DNA/Protein Number of K-tuple matches: 2/1; DNA/Protein number of best diagonals: 4/5; DNA/Protein Window size: 4/5.

Two sequences are "aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well known in the art (See, e.g., Dayhoff et al., in Dayhoff [ed.], *Atlas of Protein Sequence and Structure*," Vol. 5, Suppl. 3, Natl. Biomed. Res. Round., Washington D.C. [1978]; pp. 345-352; and Henikoff et al., Proc. Natl. Acad. Sci. USA, 89:10915-10919 [1992], both of which are incorporated herein by reference). The BLOSUM62 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acid position of each sequence at which the alignment begins and ends, and optionally by the insertion of a gap or multiple gaps in one or both sequences so as to arrive at the highest possible score. While optimal alignment and scoring can be accomplished manually, the process is facilitated by the use of a computer-implemented alignment algorithm (e.g., gapped BLAST 2.0; See, Altschul et al., Nucleic Acids Res., 25:3389-3402 [1997], which is incorporated herein by reference), and made available to the public at the National Center for Biotechnology Information Website). Optimal alignments, including multiple alignments can be prepared using readily available programs such as PSI-BLAST (See e.g., Altschul et al., supra).

The present invention also provides a recombinant nucleic acid construct comprising a xylose isomerase, xylitol dehydrogenase, and xylulokinase polynucleotide sequences that hybridize under stringent hybridization conditions to the complement of a polynucleotide which encodes a polypeptide having the amino acid sequence of SEQ ID NOS:2, 4, 6, 8, 10, 12, 14, 16, 18, 20, 22, and/or 24. An exemplary polynucleotide sequence that encodes a polypeptide having the amino acid sequence of SEQ ID NOS: 2, 4, 6, 8, 10, 12, 14, 16, 18, 20, 22, and/or, is selected from SEQ ID NOS:1, 3, 5, 7, 9, 11, 13, 15, 17, 19, 21, and/or 23.

In some embodiments, the polynucleotide that hybridizes to the complement of a polynucleotide which encodes a polypeptide having the amino acid sequence of SEQ ID NOS:2, 4, 6, 8, 10, 12, 14, 16, 18, 20, 22, and/or 24, does so under high or very high stringency conditions to the complement of a reference sequence encoding a polypeptide having the sequence of SEQ ID NOS: 2, 4, 6, 8, 10, 12, 14, 16, 18, 20, 22, and/or 24 (e.g., over substantially the entire length of the reference sequence).

Nucleic acids "hybridize" when they associate, typically in solution. There are numerous texts and other reference materials that provide details regarding hybridization methods for nucleic acids (See e.g., Tijssen, *Laboratory Techniques in Biochemistry and Molecular Biology-Hybridization with Nucleic Acid Probes*." Part 1, Chapter 2, Elsevier, New York. [1993], incorporated herein by reference). For polynucleotides of at least 100 nucleotides in length, low to very high stringency conditions are defined as follows: prehybridization and hybridization at 42° C. in 5×SSPE 0.3% SDS, 200 µg/ml sheared and denatured salmon sperm DNA, and either 25% formamide for low stringencies, 35% formamide for medium and medium-high stringencies, or 50% formamide for high and very high stringencies, following standard Southern blotting procedures. For polynucleotides of at least 200 nucleotides in length, the carrier material is finally washed three times each for 15 minutes using 2×SSC, 0.2% SDS at least at 50° C. (low stringency), at least at 55° C. (medium stringency), at least at 60° C. (medium-high stringency), at least at 65° C. (high stringency), and at least at 70° C. (very high stringency).

The terms "corresponding to", "with reference to," and "relative to" when used in the context of the numbering of a given amino acid or polynucleotide sequence refers to the numbering of the residues of a specified reference sequence when the given amino acid or polynucleotide sequence is compared to the reference sequence.

The terms "numbered with reference to" or "corresponding to," when used in the context of the numbering of a given polypeptide or polynucleotide sequence, refers to the numbering of the residues of a specified reference sequence when the given amino acid or polynucleotide sequence is compared to the reference sequence.

An amino acid or nucleotide "position" is denoted by a number that sequentially identifies each amino acid or nucleotide in the reference sequence based on its position relative to the N-terminus or 5'-terminus. Owing to deletions, insertions, truncations, fusions, and the like that must be taken into account when determining an optimal alignment, in general the amino acid residue number in a test sequence determined by simply counting from the N-terminus or 5' terminus will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence. As used herein, in referring to variants (e.g., variants with substitutions, insertions, and/or deletions), a hyphen indicates a deletion in a sequence and an asterisk indicates a mutation in a stop codon.

As used herein, the term "conservative substitution" refers to the substitution of a residue for another residue that does not generally alter the specific activity of the encoded polypeptide. In some embodiments, a "conservative substitution," as used with respect to amino acids, refers to the substitution of an amino acid with a chemically similar amino acid. An exemplary conservative substitution is a substitution that is within the same group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine, proline, cysteine and methionine). Amino acid substitutions which often preserve the structural and/or functional properties of the polypeptide in which the substitution is made are well known in the art Amino acid substitutions that do not generally alter the specific activity are known in the art (See e.g., Neurath and Hill, *The Proteins*, Academic Press, New York [1979], which is incorporated herein by reference). Some of the most commonly occurring exchanges are Ala/Ser, Val/Ile, Asp/Glu, Thr/Ser, Ala/Gly, Ala/Thr, Ser/Asn, Ala/NaI, Ser/Gly, His/Asn, His/

Gln, Lys/Asn, Lys/Gln, Lys/Gln, Tyr/Phe, Tyr/His, Tyr/Tarp, Ala/Pro, Lys/Arg, Gln/Arg, Asp/Asn, Leu/Ile, Leu/NaI, Leu/Met, Ile/Met, Ala/Glu, Glu/Gln, Phe/Leu, Phe/Met, Val/Met, and Asp/Gly, as well as these in reverse.

The following nomenclature finds use in describing substitutions in a reference sequence relative to a reference sequence or a variant polypeptide or nucleic acid sequence: "R-#-V." where "#" refers to the position in the reference sequence, "R" refers to the amino acid (or base) at that position in the reference sequence, and "V" refers to the amino acid (or base) at that position in the variant sequence. In some embodiments, an amino acid (or base) may be called "X," by which is meant any amino acid (or base). As a non-limiting example, for a variant polypeptide described with reference to SEQ ID NO:2, "E10G" indicates that in the variant polypeptide, the glutamic acid at position 10 of the reference sequence is replaced by glycine, with amino acid position being determined by optimal alignment of the variant sequence with SEQ ID NO:2. Similarly, "E10G/D" describes two variants: a variant in which the glutamic acid at position 10 of the reference sequence is replaced by glycine; and a variant in which the glutamic acid at position 10 of the reference sequence is replaced by aspartic acid.

As used herein, the terms "amino acid substitution set" and "substitution set" when used in the context of amino acid sequences (e.g., polypeptides) refer to a group of (i.e., multiple) amino acid substitutions.

As used herein, the terms "amino acid mutation set" and "mutation set" when used in the context of amino acid sequences (e.g., polypeptides) refer to a group of (i.e., multiple) amino acid substitutions, insertions, and/or deletions.

As used herein, the terms "nucleic acid substitution set" and "substitution set" when used in the context of nucleotide sequences (e.g., polynucleotides) refer to a group of (i.e., multiple) nucleic acid substitutions.

As used herein, the terms "nucleic acid mutation set" and "mutation set" when used in the context of nucleotide sequences (e.g., polynucleotides) refer to a group of (i.e., multiple) nucleic acid substitutions, insertions, and/or deletions.

As used herein, the terms "host cell" and "host strain" refer to suitable hosts for expression vectors comprising DNA provided herein. In some embodiments, the host cells are prokaryotic or eukaryotic cells that have been transformed or transfected with vectors constructed using recombinant DNA techniques as known in the art. Transformed hosts are capable of either replicating vectors encoding at least one protein of interest and/or expressing the desired protein of interest. In addition, reference to a cell of a particular strain refers to a parental cell of the strain as well as progeny and genetically modified derivatives. Genetically modified derivatives of a parental cell include progeny cells that contain a modified genome or episomal plasmids that confer for example, antibiotic resistance, improved fermentation, etc. In some embodiments, host cells are genetically modified to have characteristics that improve protein secretion, protein stability or other properties desirable for expression and/or secretion of a protein. Genetic modification can be achieved by any suitable genetic engineering techniques and/or classical microbiological techniques (e.g., chemical or UV mutagenesis and subsequent selection). Using recombinant technology, nucleic acid molecules can be introduced, deleted, inhibited or modified, in a manner that results in increased yields of enzyme(s) of interest within the organism or in the culture. In some genetic engineering approaches, homologous recombination is used to induce targeted gene modifications by specifically targeting a gene in vivo to suppress expression of the encoded protein. In an alternative approach, siRNA, antisense, and/or ribozyme technology finds use in inhibiting gene expression.

As used herein, the term "transformed" or "transformation" used in reference to a cell means that the cell has a non-native nucleic acid sequence integrated into its genome or has an episomal plasmid that is maintained through multiple generations.

As used herein, the term "by-product" refers to an organic molecule that is an undesired product of a particular fermentation process.

As used herein, the term "xylose pathway" refers to the steps of conversion of xylose to xylulose phosphate which is then metabolized through the pentose phosphate pathway. In some embodiments, this involves the reduction of xylose to xylitol, oxidation of xylitol to xylulose and subsequent conversion of xylulose to xylulose phosphate. In some other embodiments the xylose is directly converted to xylulose which is then phosphorylated to xylulose phosphate.

As used herein the term "xylose pathway enzymes" refers to the enzymes that catalyze the conversion of xylose to xylulose phosphate which is then metabolized through the pentose phosphate pathway. In some embodiments, these enzymes comprise xylose reductase, xylitol dehydrogenase and/or xylulose kinase. In some other embodiments, the enzymes comprise xylose isomerase and xylulose kinase. In some additional embodiments, the enzymes comprise xylose isomerase, xylitol dehydrogenase, and xylulokinase.

DETAILED DESCRIPTION OF THE INVENTION

The present invention provides methods and compositions suitable for use in the isomerization of xylose to xylulose, as well as methods and compositions suitable for use in the conversion of xylose to xylitol and xylulose, including nucleic acid constructs, recombinant fungal host cells, and related materials.

The initial metabolic pathways for xylose utilization in fungi and bacteria differ. In most fungi, including xylose-fermenting yeasts (e.g., *Pichia stipitis*, *Pachysolen tannophilus*, and *Candida shehatae*), D-xylose is converted to D-xylulose by two oxidoreductases involving cofactors NAD(P)H and NAD(P)+(See, Matsushika et al., Appl. Microbiol. Biotechnol., 84:37-53 [2009]). In these organisms, D-xylose is initially reduced to xylitol by NAD(P)H-dependent xylose reductase (XR) (EC 1.1.1.21). Xylitol is subsequently oxidized to D-xylulose by NAD+-dependent xylitol dehydrogenase (XDH) (EC 1.1.1.9). Xylulokinase (XK) (EC 2.7.1.17) subsequently phosphorylates D-xylulose to produce D-xylulose 5-phosphate (X5P), which is then further metabolized through the pentose phosphate pathway (PPP).

However, most strains of *S. cerevisiae* cannot utilize xylose even though the genes encoding XR, XDH, and XK are present in its genome, as the expression levels of these enzymes are too low to allow xylose utilization (See, Matsushika et al., supra). Some strains have been shown to natively utilize xylose but at very low rates and fermentation to ethanol has not been detected (See. Wenger et al., PLoS Genet., 6(5):e1000942 [2010]). Even when the endogenous genes are overexpressed in *S. cerevisiae*, only slow growth on xylose has been observed (See, Matsushika et al., supra).

In contrast, most bacteria (e.g., *Escherichia coli* and *Streptomyces* species) can isomerize D-xylose directly to D-xylulose by using a xylose isomerase (XI) (EC 5.3.1.5)

(See, Matsushika et al., supra). In bacteria, as in fungi, the D-xylulose is phosphorylated to D-xylulose 5-phosphate by XK, which is then further metabolized through the pentose phosphate pathway.

Efforts to express a functional heterologous xylose isomerase gene (xylA) in *S. cerevisiae* and grow the yeast on xylose has met with very limited success (See e.g., Matsushika et al. supra). It has been reported that xylose isomerase genes from the fungi *Piromyces* (Kuyper et al. FEMS Yeast Res., 4:69-78 [2003]) and *Orpinomyces* (Madhaven et al., Appl. Microbiol. Biotechnol., 82:1067-1078 [2009a]) have been functionally expressed in *S. cerevisiae*, but that growth on xylose was very slow. In addition, the functional expression of the *Thermus thermophilus* xylose isomerase (Accession No. 1BXB) in *S. cerevisiae* has been reported (See, Walfridsson et al., Appl. Environ. Microbiol., 62:4648-4651 [1996]). The success in producing an active xylose isomerase by expressing the *T. thermophilus* xylA gene in *S. cerevisiae* may have been due to the relatedness between the two organisms, as *T. thermophilus* diverged from the domain of eubacteria and may, in many respects, be more closely related to *S. cerevisiae* than are the eubacteria (Id., at 4651).

Heterologous expression of xylose isomerase genes from *Actinoplanes missouriensis* and *Clostridium thermosulfurogenes* in *S. cerevisiae* generated inactive proteins, even though their messenger RNA could be detected (See, Amore et al., Appl. Microbiol. Biotechnol., 30:351-357 [1989]); and Moes et al., Biotech. Lett., 18:269-274 [1996]; and Matsushika et al., supra). Other studies report the heterologous expression of the xylA from *E. coli* (See e.g., Sarthy et al., Appl. Environ. Microbiol. 53:1996-2000 [1987]), *Bacillus subtilis* (Amore et al., Appl. Microbiol. Biotechnol., 30:351-357 [1989]), and *Streptomyces rubiginosus* (Gárdonyi et al., Enzyme Microb. Technol., 32:252-259 [2003]) in *S. cerevisiae* resulted in mainly insoluble proteins which were catalytically inactive (See. Matsushika et al., supra). In addition, some reports indicate that attempts to produce xylose isomerase from recombinant *S. cerevisiae* transformed with the xylA genes from *Bacillus subtilis* and *Lactobacillus pentosus* resulted in inactive protein (See. Walfridsson et al., supra).

In further studies, the results of screening for xylose isomerase activity in *S. cerevisiae* transformed with the xylose isomerase genes from various organisms have been reported (See e.g., Brat et al., Appl. Environ. Microbiol. Doi: 10.1128/AEM.02522-9 [13 Feb. 2009]). The xylose isomerases have been reported to share from 17% to 60% sequence identity to the xylose isomerase from *Piromyces*. While transformants expressing the xylose isomerase from *Clostridium phytofermentans* (DSM 18823) could grow on xylose medium, *S. cerevisiae* transformed with the xylose isomerase gene from the following organisms could not: *Bacillus licheniformis* (DSM 13), *Burkholderia xenovaorans*(DSM 17367), *Lactobacillus pentosus* (DSM 20314), *Leifsonia xyli* subsp. *cynodontis* (DSM 46306), *Pseudomonas savastanoi* pvar. *Phaseolicola* (DSM 50282), *Robiginitalea biformata* (DSM 15991). *Saccharophagus degradans* (DSM 17024), *Staphylococcus xylosus* (DSM 20266), *Streptomyces diastaticus* subsp. *diastaticus* (DSM 40496), *Xanthomonas campestris* var. *campestris* (DSM 3586), *Salmonella typhimurium* (71-098L), *Agrobacterium tumefaciens*, and *Arabidopsis thaliana* (See. Brat et al., supra).

The present invention provides sequences that are capable of conferring the property of xylose-utilization in a non-mammalian, eukaryotic host cell, such as, for example, a fungal host cell. These sequences and variants thereof, encode xylose isomerases, which catalyze the isomerization of D-xylose directly to D-xylulose, as depicted in FIG. 1. Xylose isomerase is distinguished from xylose reductase (XR), which catalyzes the conversion of xylose to xylitol. Xylose isomerase is also distinguished from xylitol dehydrogenase (XD), which catalyzes the conversion of xylitol to D-xylulose (See, FIG. 1).

Figure 2A:
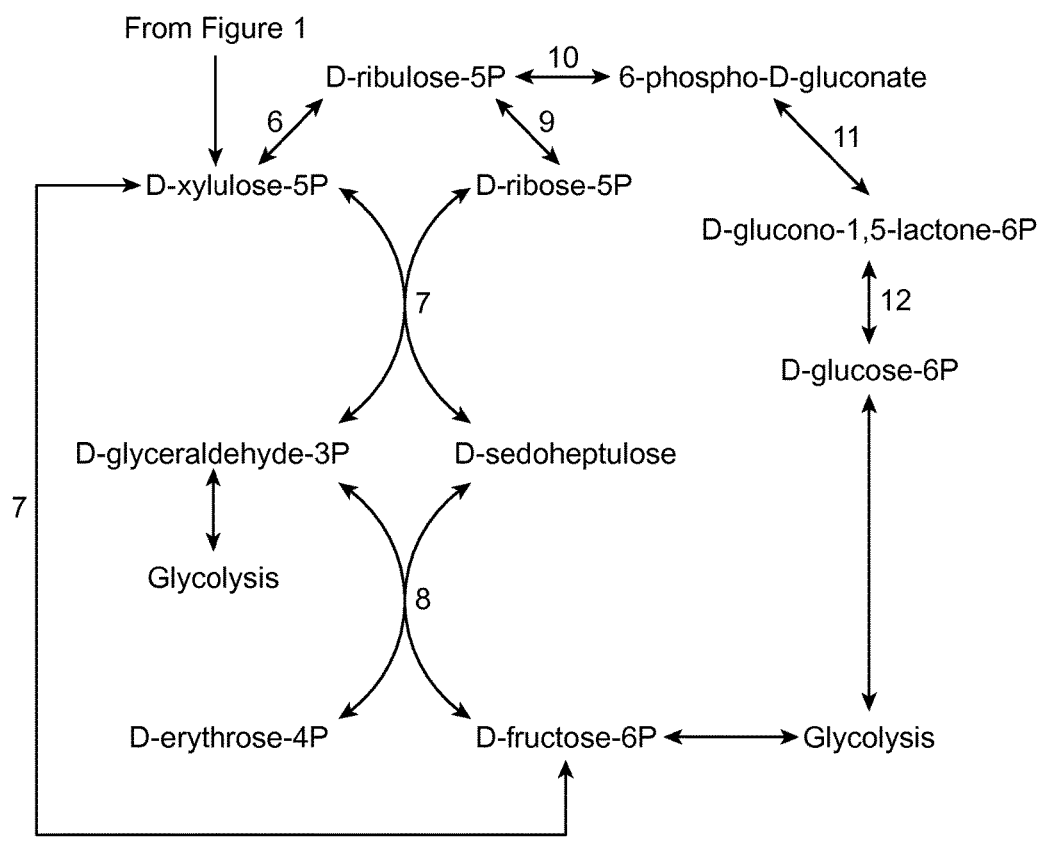
FIGS. 2A-C illustrate the metabolic pathways for converting D-xylulose-5-P to ethanol.

Xylose utilization by these host cells results in useful products that are produced metabolically by the host cell. In these host cells, D-xylose may be phosphorylated by a native or recombinant xylulokinase to xylulose-5-P, as depicted in FIG. 1. The xylulose-5-P may be further metabolized by enzymes in the pentose phosphate pathway to products such as glucose-6-P, fructose-6-P, glyceraldehydes-3-P, and the like. The pentose phosphate pathway and relevant enzymes and products are depicted in FIG. 2A. As used herein, the terms "enzyme from the pentose phosphate pathway" and "pentose phosphate pathway enzyme" are used interchangeably to refer to an enzyme from the group of enzymes involved in the pentose phosphate pathway, (i.e., 6. ribulose-5-phosphate ketoisomerase (RK11); 7. transketolase (TKL1); 8. transaldolase (TAL1); 9. ribose-5-phosphate ketolisomerase (RK11); 10. 6-phosphogluconate dehydrogenase (GND1); 11. 6-phosphogluconalactonase (SOL3); and/or 12. glucose-6-phosphate-1-dehydrogenase (ZWF); the reference numbers correspond to those in FIG. 2A).

Figure 2B:
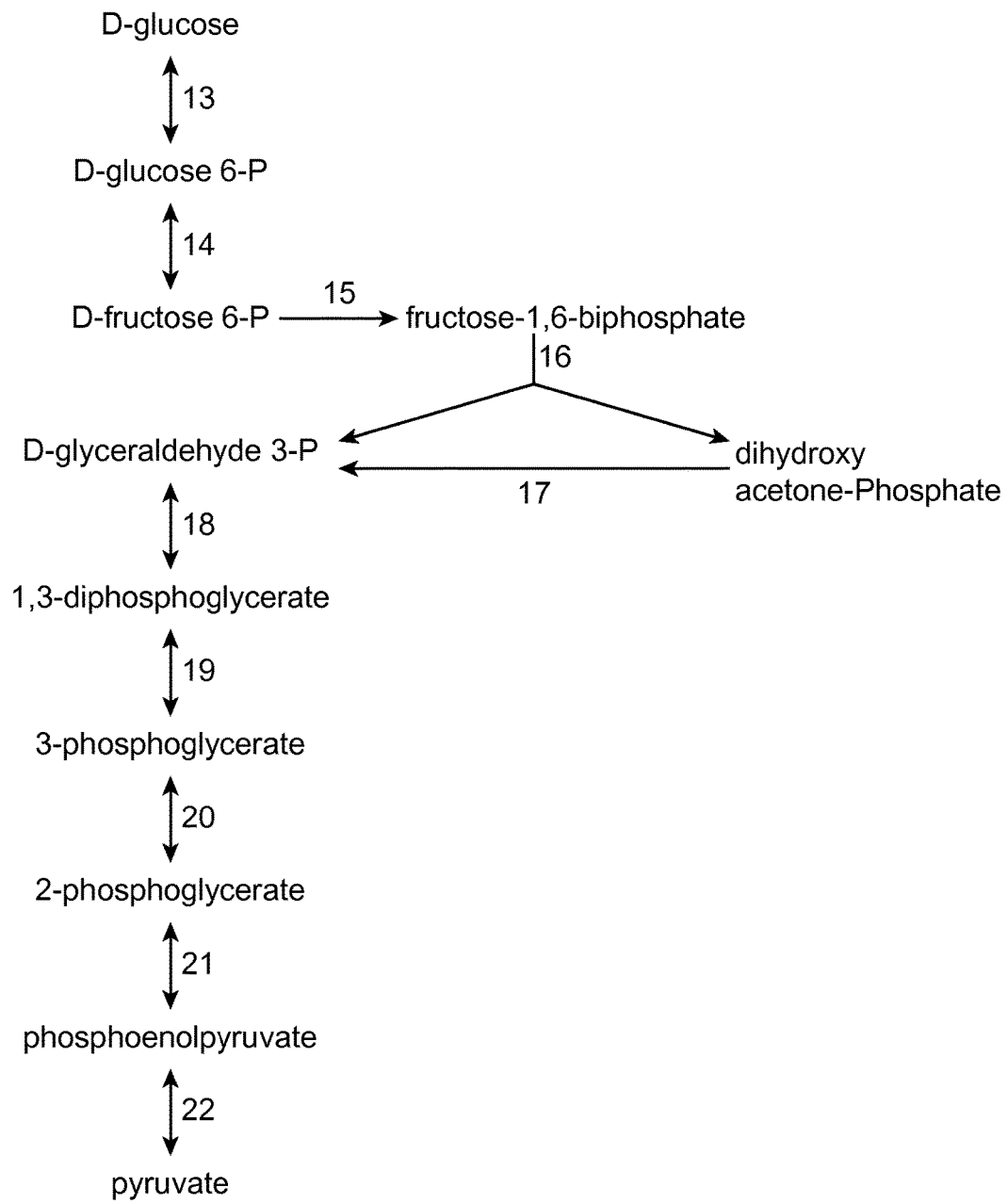

Products of the pentose phosphate pathway may be further metabolized through the process of glycolysis. The metabolic process of glycolysis is depicted in FIG. 2B. As used herein, the term "glycolytic enzyme" refers to an enzyme from the group of enzymes involved in glycolysis (i.e.: 13. hexokinase; 14. phosphoglucose isomerase; 15. phosphofructokinase; 16. aldolase; 17. triose phosphate isomerase; 18. glyceraldehyde phosphate dehydrogenase; 19. phosphoglycerate kinase; 20. phosphoglyceromutase; 21. enoase; and/or 22. pyruvate kinase; the reference numbers correspond to those in FIG. 2B).

Figure 2C:
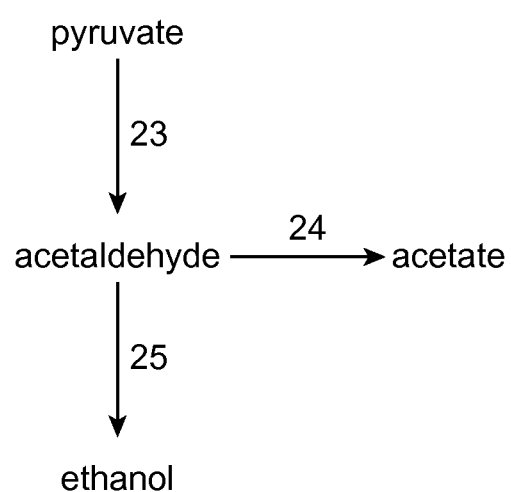

Pyruvate from the glycolytic pathway (i.e., glycolysis) may be further metabolized to ethanol as shown in FIG. 2C by ethanologenic enzymes. As used herein, the term "ethanologenic enzyme" refers to an enzyme involved in the conversion of pyruvate to ethanol, (e.g., a pyruvate decarboxylase, an aldehyde dehydrogenase, and/or an alcohol dehydrogenase). The term "ethanologenic pathway" refers to the pathway depicted in FIG. 2C.

The polynucleotide sequences described herein are useful for creating recombinant fungal host cells, particularly yeast host cells, that are capable of isomerizing D-xylose directly to D-xylulose, which can lead to the production of desirable fermentation products. Recombinant host cells transformed with xylose reductase and xylitol dehydrogenase genes are hence capable of converting xylose to xylitol and then converting xylitol to xylulose, which can lead to the production of desirable fermentation products (e.g., an alcohol, such as ethanol, butanol, and the like, including, but not limited to a fatty alcohol [e.g., a C8-C20 fatty alcohol], a fatty acid [e.g., a C8-C20 fatty acid], lactic acid, 3-hydroxpropionic acid, acrylic acid, acetic acid, succinic acid, citric acid, malic acid, fumaric acid, an amino acid, 1,3-propanediol, ethylene, glycerol, a β-lactam, and the like). However, previous reports have indicated that cells transformed with wild-type xylose reductase and xylitol dehydrogenase genes from *Pichia stipitis* convert xylose inefficiently and with accumulation of xylitol (Matsushika et al., Appl. Environ Microbiol., 81:243-55 [2008]).

In contrast, recombinant host cells transformed with xylose isomerase, xylitol dehydrogenase, and xylulokinase genes as described herein, are capable of converting xylose to desirable fermentation products (e.g., an alcohol, such as ethanol, butanol, and the like, including, but not limited to a fatty alcohol [e.g., a C8-C20 fatty alcohol], a fatty acid [e.g., a C8-C20 fatty acid], lactic acid, 3-hydroxpropionic acid, acrylic acid, acetic acid, succinic acid, citric acid, malic acid, fumaric acid, an amino acid, 1,3-propanediol, ethylene, glycerol, a β-lactam, and the like). In some embodiments, the recombinant host cells are further transformed with genes encoding xylose reductase.

Recombinant Nucleic Acid Constructs

In some embodiments, the present invention provides recombinant nucleic acid constructs comprising a polynucleotide sequence that encodes a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:2, 8, 10, 12, 14, 16, 18, 20, 22, and/or 24; a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:4; and/or a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:6. In some embodiments, the polypeptide(s) comprises at least one substitution and/or other mutation.

The present invention provides recombinant nucleic acid constructs comprising polynucleotide sequences that encode at least one polypeptide comprising amino acid sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:2, 4, 6, 8, 10, 12, 14, 16, 18, 20, 22, and/or 24; a polypeptide comprising an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:4; and a polypeptide comprising an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:6. In some embodiments, the polypeptide(s) comprises at least one substitution and/or other mutation.

In some embodiments, the present invention provides recombinant nucleic acid constructs comprising a polynucleotide sequence that encodes a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:2, 8, 10, 12, 14, 16, 18, 20, 22, and/or 24; a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:4; and a polypeptide comprising an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:6. In some embodiments, the polypeptide(s) comprises at least one substitution and/or other mutation.

The present invention provides recombinant nucleic acid constructs comprising polynucleotide sequences that encode a polypeptide comprising amino acid sequences having at least 70%. % least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:2, 4, 6, 8, 10, 12, 14, 16, 18, 20, 22, and/or 24; a polypeptide comprising an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:4; a polypeptide comprising an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NO:6. In some embodiments, the polypeptide(s) comprises at least one substitution and/or other mutation.

The present invention also provides nucleic acid constructs comprising polynucleotides encoding at least one xylose reductase, xylitol dehydrogenase and/or xylulokinase. The present invention further provides nucleic acid constructs comprising polynucleotides encoding at least one xylose reductase, xylitol dehydrogenase and xylulokinase. In some of these embodiments, the nucleic acid constructs comprise SEQ ID NOS:1, 7, 9, 11, 13, 15, 17, 19, 21, and/or 23; SEQ ID NO:3; and/or SEQ ID NO:5. In some additional embodiments, the nucleic acid constructs comprise SEQ ID NOS:1, 7, 9, 11, 13, 15, 17, 19, 21, and/or 23; SEQ ID NO:3; and SEQ ID NO:5.

In some embodiments, recombinant nucleic acid constructs of the present invention further comprise at least one polynucleotide sequence (i.e., genetic) element that facilitates integration into a fungal host cell genome, by homologous or non-homologous recombination. In some embodiments, the nucleic acid construct of the present invention further comprises an origin of replication that is functional in a fungal cell (e.g., a yeast origin of replication). Typically, the fungal host cell is a yeast or filamentous fungal cell, more typically, a yeast cell. In some embodiments, nucleic acid constructs of the present invention comprise at least one transcriptional regulatory element that is functional in a fungal cell. For example, in some embodiments the recombinant nucleic acid construct comprises at least one promoter sequence and/or transcription terminator sequence that is functional in a fungal cell such that the xylose isomerase, xylitol dehydrogenase, and/or xylulokinase polynucleotide is operatively linked to the promoter sequence and/or transcription terminator sequences. In some additional embodiments the recombinant nucleic acid construct comprises at least one promoter sequence and/or transcription terminator sequence that is functional in a fungal cell such that the xylose isomerase, xylitol dehydrogenase, and xylulokinase polynucleotide are operatively linked to the promoter sequence and/or transcription terminator sequences.

Additional xylose isomerase, xylose reductase, xylitol dehydrogenase, and xylulokinase polynucleotides suitable for use in the practice of the present invention include those encoding variants generated by mutagenesis, recombination, and/or any other protein engineering method. In some embodiments, the variants are screened for xylose utilization using any suitable method as known in the art. In some embodiments, the resulting variants comprise one or more substitutions (conservative or non-conservative), deletions, and/or insertions.

Methods for generating variant libraries of polynucleotides encoding modified polypeptides are well known in the art. For example, mutagenesis and directed evolution methods can be readily applied to polynucleotides encoding xylose isomerase, xylitol dehydrogenase, and/or xylulokinase polypeptides to generate variant libraries that can be expressed, screened, and assayed using any suitable methods known in the art. Mutagenesis and directed evolution methods are well known in the art (See e.g., U.S. Pat. Nos. 5,605,793, 5,830,721, 6,132,970, 6,420,175, 6,277,638, 6,365,408, 6,602,986, 7,288,375, 6,287,861, 6,297,053, 6,576,467, 6,444,468, 5,811238, 6,117,679, 6,165,793, 6,180,406, 6,291,242, 6,995,017, 6,395,547, 6,506,602, 6,519,065, 6,506,603, 6,413,774, 6,573,098, 6,323,030, 6,344,356, 6,372,497, 7,868,138, 5,834,252, 5,928,905, 6,489,146, 6,096,548, 6,387,702, 6,391,552, 6,358,742, 6,482,647, 6,335,160, 6,653,072, 6,355,484, 6,03,344, 6,319,713, 6,613,514, 6,455,253, 6,579,678, 6,586,182, 6,406,855, 6,946,296, 7,534,564, 7,776,598, 5,837,458, 6,391,640, 6,309,883, 7,105,297, 7,795,030, 6,326,204, 6,251,674, 6,716,631, 6,528,311, 6,287,862, 6,335,198, 6,352,859, 6,379,964, 7,148,054, 7,629,170, 7,620,500, 6,365,377, 6,358,740, 6,406,910, 6,413,745, 6,436,675, 6,961,664, 7,430,477, 7,873,499, 7,702,464, 7,783,428, 7,747,391, 7,747,393, 7,751,986, 6,376,246, 6,426,224, 6,423,542, 6,479,652, 6,319,714, 6,521,453, 6,368,861, 7,421,347, 7,058,515, 7,024,312, 7,620,502, 7,853,410, 7,957,912, 7,904,249, and all related non-US counterparts; Ling et al., Anal. Biochem., 254(2):157-78 [1997]; Dale et al., Meth. Mol. Biol., 57:369-74 [1996]; Smith, Ann. Rev. Genet., 19:423-462 [1985]; Botstein et al., Science, 229: 1193-1201 [1985]; Carter, Biochem. J., 237:1-7 [1986]; Kramer et al., Cell, 38:879-887 [1984]; Wells et al., Gene, 34:315-323 [1985]; Minshull et al., Curr. Op. Chem. Biol., 3:284-290 [1999]; Christians et al., Nat. Biotechnol., 17:259-264 [1999]; Crameri et al., Nature, 391:288-291 [1998]; Crameri, et al., Nat. Biotechnol., 15:436-438 [1997]; Zhang et al., Proc. Nat. Acad. Sci. U.S.A., 94:4504-4509 [1997]; Crameri et al., Nat. Biotechnol., 14:315-319 [1996]; Stemmer, Nature, 370:389-391 [1994]; Stemmer, Proc. Nat. Acad. Sci. USA, 91:10747-10751 [1994]; WO 95/22625; WO 97/0078; WO 97/35966; WO 98/27230; WO 00/42651; WO 01/75767; and WO 2009/152336, all of which are incorporated herein by reference).

Also suitable for use in the practice of the present invention are polynucleotides encoding a truncated xylose isomerase, xylitol dehydrogenase, and/or xylulokinase or sequence variant(s) thereof. These truncation variants may be truncated at the carboxy (C)-terminus and/or the amino (N)-terminus. Typically, the truncation is from about 1 to about 50 amino acid residues. However, it not intended that the present invention be limited to any specific number of truncated amino acid residues.

Those having ordinary skill in the art will understand that due to the degeneracy of the genetic code, a multitude of nucleotide sequences that encode the xylose isomerase, xylitol dehydrogenase, and xylulokinase polypeptides described herein exist. Table 1 provides the standard triplet genetic code for each amino acid. For example, the codons AGA, AGG, CGA, CGC, CGG, and CGU all encode the amino acid arginine. Thus, at every position in the nucleic acids referred to herein, where an arginine is specified by a codon, the codon can be altered to any of the corresponding codons described above without altering the encoded polypeptide. It is understood that U in an RNA sequence corresponds to T in a DNA sequence. The invention contemplates and provides each and every possible variation of nucleic acid sequence encoding a polypeptide of the invention that could be made by selecting combinations based on possible codon choices.

TABLE 1

Genetic Code

| Amino Acid | 3 Letter Code | Single Letter Code | Codon(s) |
| --- | --- | --- | --- |
| Alanine | Ala | A | GCA, GCC, GCG, GCU |
| Cysteine | Cys | C | UGC, UGU |
| Aspartic acid | Asp | D | GAC, GAU |
| Glutamic acid | Glu | E | GAA, GAG |
| Phenylalanine | Phe | F | UUC, UUU |
| Glycine | Gly | G | GGA, GGC, GGG, GGU |
| Histidine | His | H | CAC, CAU |
| Isoleucine | Ile | I | AUA, AUC, AUU |
| Lysine | Lys | K | AAA, AAG |
| Leucine | Leu | L | UUA, UUG, CUA, CUC, CUG, CUU |
| Methionine | Met | M | AUG |
| Asparagine | Asn | N | AAC, AAU |
| Proline | Pro | P | CCA, CCC, CCG, CCU |
| Glutamine | Gln | Q | CAA, CAG |
| Arginine | Arg | R | AGA, AGG, CGA, CGC, CGG, CGU |
| Serine | Ser | S | AGC, AGU, UCA, UCC, UCG, UCU |
| Threonine | Thr | T | ACA, ACC, ACG, ACU |
| Valine | Val | V | GUA, GUC, GUG, GUU |
| Tryptophan | Trp | W | UGG |
| Tyrosine | Tyr | Y | UAC, UAU |

In some embodiments, DNA sequences are designed for high codon usage bias (i.e., codons that are used at higher frequency in the protein coding regions than other codons that code for the same amino acid). The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. In particular, a DNA sequence can be optimized for expression in a particular host organism. References providing preference information for a wide range of organisms are readily available and known in the art (See e.g., Henaut and Danchin in Neidhardt et al. [eds.], *Escherichia coli and Salmonella*, ASM Press, Washington D.C., [1987], p. 2047-2066, which is incorporated herein by reference).

A variety of methods are known for determining the codon frequency (e.g., codon usage, relative synonymous codon usage) and codon preference in specific organisms, including multivariate analysis, for example, using cluster analysis or correspondence analysis, and the effective number of codons used in a gene (See, GCG CodonPreference, Genetics Computer Group Wisconsin Package; Peden, *Codon W*, University of Nottingham; McInerney, Bioinform., 14:372-73 [1998]; Stenico et al., Nucl. Acids Res. 222437-46 [1994]; Wright, Gene 87:23-29 [1990]; Wada et al., Nucl. Acids Res., 20:2111-2118 [1992]; Nakamura et al., Nucl. Acids Res., 28:292 [2000]; and Henaut and Danchin, supra; all of which are incorporated herein by reference). The data source for obtaining codon usage may rely on any available nucleotide sequence capable of coding for a protein. These data sets include nucleic acid sequences actually known to express proteins (e.g., complete protein coding sequences-CDS), expressed sequence tags (ESTs), or predicted coding regions of genomic sequences (See e.g., Mount, *Bioinformatics: Sequence and Genome Analysis*, Chapter 8, Cold Spring Harbor Laboratory Press, Cold Spring Harbor, N.Y. [2001]; Uberbacher, Methods Enzymol. 266:259-281 [1996]; and Tiwari et al., Comput. Appl. Biosci 13:263-270 [1997]; all of which are incorporated herein by reference). It is not intended that the present invention be limited to any particular method, data source and/or data set.

In some embodiments, the xylose isomerase, xylitol dehydrogenase and/or xylulokinase polynucleotide contains codons optimized for expression in a fungal cell, particularly a yeast cell. In some embodiments, silent mutations (i.e., DNA mutations that do not affect the amino acid sequence of the protein) are also present. In some embodiments, the xylose isomerase, xylitol dehydrogenase, and/or xylulokinase polynucleotides are employed in recombinant nucleic acid constructs that comprise a vector (e.g., a plasmid, a cosmid, a phage, a virus, a yeast artificial chromosome [YAC], and the like), into which xylose isomerase, xylitol dehydrogenase, and/or xylulokinase polynucleotide sequence(s) has/have been inserted. The xylose isomerase, xylitol dehydrogenase, and xylulokinase polynucleotides provided herein find use incorporated into any one of a variety of vectors. Suitable vectors include, but are not limited to chromosomal, nonchromosomal and synthetic DNA sequences, yeast plasmids, vectors derived from combinations of plasmids and phage DNA, and many others. Indeed, any suitable vector that transduces genetic material into a cell, and, if replication is desired, that is replicable and viable in the relevant host find use in the present invention.

Nucleic acid constructs of the present invention find use in transforming a host cell to permit the host to express the xylose isomerase, xylitol dehydrogenase, and/or xylulokinase polypeptide(s). Methods for recombinant expression of proteins in fungi are well known in the art, and a number of vectors are available or can be constructed using routine methods (See e.g., Zhu et al., Plasmid 6:128-33 [2009], incorporated herein by reference: and the many standard references in this field).

In some embodiments, recombinant nucleic acid constructs of the present invention further comprise a transcriptional regulatory element that is functional in a fungal cell. In some embodiments, the nucleic acid construct comprises the xylose isomerase, xylitol dehydrogenase and/or xylulokinase polynucleotide(s) operatively linked to a transcriptional regulatory sequence (e.g., a promoter, transcription termination sequence, and the like), that is functional in a fungal cell. Examples of promoters that are functional in a fungal host cell include, but are not limited to promoters from yeast and filamentous fungi. Promoters that are suitable for use in the practice of the present invention include endogenous or heterologous promoters and include both constitutive and inducible promoters that are natural or modified. Particularly useful promoters are those that are insensitive to catabolite (glucose) repression and/or do not require xylose for induction. Such promoters are well known in the art. In some embodiments, a promoter sequence is operably linked to the 5' region of the xylose isomerase, xylitol dehydrogenase, and/or xylulokinase coding sequence using routine methods that are well known in the art.

Promoters that are suitable for use in the practice of the present invention include, but are not limited to yeast promoters from glycolytic genes (e.g., yeast phosphofructokinase (PFK), triose phosphate isomerase (TPI), glyceraldehyde-3-phosphate dehydrogenase (GPD, TDH3 or GAPDH), pyruvate kinase (PYK), phosphoglycerate kinase (PGK) promoters, and the like; See e.g., WO 93/03159, incorporated herein by reference); promoters of glucose transporters; ribosomal protein encoding gene promoters; alcohol dehydrogenase promoters (e.g., ADH1, ADH4, and the like), and the enolase promoter (ENO).

Exemplary promoters useful for directing the transcription of the nucleic acid constructs of the present invention in yeast host cells include, but are not limited to those from the genes for *Saccharomyces cerevisiae* enolase (eno-1), *Saccharomyces cerevisiae* galactokinase (gal1), *Saccharomyces cerevisiae* alcohol dehydrogenase/glyceraldehyde-3-phosphate dehydrogenase (ADH1/ADH2/GAP), and *Saccharomyces cerevisiae* 3-phosphoglycerate kinase, *Saccharomyces cerevisiae* transcription elongation factor (TEF), *Saccharomyces cerevisiae* fructose 1,6-bisphosphate aldolase (FBA1), and *Saccharomyces cerevisiae* 3-phosphate glycerate kinase (PGK1). Other useful promoters for yeast host cells are well known in the art (See e.g., Romanos et al., Yeast 8:423-488 [1992], incorporated herein by reference).

Suitable filamentous fungal promoters useful in the practice of the present invention include, but are not limited to promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (See e.g., WO 96/00787, which is incorporated herein by reference), as well as the NA2-tpi promoter (a hybrid of the promoters from the genes for *Aspergillus niger* neutral alpha-amylase and *Aspergillus oryzae* triose phosphate isomerase), promoters such as cbh1, cbh2, egl1, egl2, pepA, hfb1, hfb2, xyn1, amy, and glaA (See, Nunberg et al., Mol. Cell Biol. 4:2306-2315 [1984]; Boel et al., EMBO J. 3:1581-85 [1984]; and EP 0 137 280A, all of which are incorporated herein by reference), and mutant, truncated, and hybrid promoters thereof. Promoters associated with chitinase production in fungi also find use in some embodiments (See e.g., Blaiseau and Lafay, Gene 120:243-248 [1992][filamentous fungus *Aphanocladium album*]; and Limon et al., Curr. Genet., 28:478-83 [1995][*Trichoderma harzianum*]; both of which are incorporated herein by reference).

Any other suitable promoter sequence that drives expression in a fungal host cell, particularly a yeast host cell finds use in the present invention. Suitable promoter sequences can be identified using well known methods. In one approach, a putative promoter sequence is linked 5' to a sequence encoding a reporter protein, the construct is transfected into the host cell and the level of expression of the reporter is measured. Expression of the reporter can be determined by measuring, for example, mRNA levels of the reporter sequence, an enzymatic activity of the reporter protein, or the amount of reporter protein produced. For example, promoter activity may be determined by using the green fluorescent protein as coding sequence (See e.g., Henriksen et al., Microbiol., 145:729-34 [1999], which is incorporated herein by reference) or a lacZ reporter gene (See e.g., Punt et al., Gene, 197:189-93 [1997], which is incorporated herein by reference). In some embodiments, functional promoters are derived from naturally occurring promoter sequences by directed evolution methods (See e.g., Wright et al., Hum. Gene Ther., 16:881-892 [2005], which is incorporated herein by reference).

In some embodiments, heterologous and/or recombinant transcription termination sequences find use in the present invention. There are various exemplary transcription termination sequences (terminators) functional in fungal host cells, include transcription termination sequences from yeast and filamentous fungi well known in the art. In some embodiments, the transcription termination sequence is a yeast sequence. Exemplary yeast transcription termination sequences include, but are not limited to CYC1, ADH1t, ADH2t, etc. In some embodiments, the nucleic acid constructs of the present invention contain a ribosome binding site for translation initiation. In some embodiments, the construct includes appropriate sequences for amplifying expression (e.g., an enhancer). Such elements are well known in the art and any suitable enhancers and/or transcription termination sequences, and/or ribosome binding sites find use in the present invention.

In some additional embodiments, nucleic acid constructs of the present invention contain one or more selectable marker genes to provide a phenotypic trait for selection of transformed host cells. Suitable marker genes include, but are not limited to those coding for antimicrobial resistance such as, ampicillin (ampR), kanamycin, chloramphenicol, tetracycline, streptomycin or spectinomycin (e.g., the aada gene); including but not limited to the streptomycin phosphotransferase (spt) gene coding for streptomycin resistance, the neomycin phosphotransferase (nptII) gene encoding kanamycin or geneticin resistance, the nourseothricin acetyltransferase (nat1) gene coding for nourseothricin resistance, the hygromycin phosphotransferase (hpt) gene coding for hygromycin resistance, genes encoding dihydrofolate reductase, phleomycin, or neomycin resistance for eukaryotic cell culture, and tetracycline or ampicillin resistance in *E. coli*, as well as other marker genes that are well known in the art. Indeed, any suitable marker gene finds use in the present invention.

In some embodiments, nucleic acid constructs of the present invention typically comprise a fungal origin of replication (e.g., a filamentous fungal or yeast origin of replication). In some embodiments, the recombinant nucleic acid constructs of the present invention comprise a yeast origin of replication. Examples include, but are not limited to constructs containing autonomous replicating sequences, constructs containing 2 micron DNA including the autonomous replicating sequence and rep genes, constructs containing centromeres like the CEN6, CEN4, CEN11, CDN3 and autonomous replicating sequences, and other like sequences that are well known in the art. Exemplary nucleic acid constructs include constructs suitable for transforming yeast. These include, but are not limited to episomal constructs based on the yeast 2µ or CEN origin based plasmids like pYES2/CT, pYES3/CT, pESC/His, pESC/Ura, pESC/

Trp, pES/Leu, p427TEF, pRS405, pRS406, pRS413, and other yeast-based constructs that are known in the art. Indeed, any suitable origin of replication finds use in the present invention.

In some embodiments, the nucleic acid constructs of the present invention comprise elements to facilitate integration of the xylose isomerase, xylitol dehydrogenase and/or xylulokinase polynucleotide(s) into a fungal host chromosome (i.e., the genome), by either homologous or non-homologous recombination and/or either site-directed and/or random mutagenesis. In some embodiments, the nucleic acid constructs comprise elements that facilitate homologous integration. In some embodiments, the xylose isomerase, xylitol dehydrogenase, and/or xylulokinase polynucleotide is integrated at one or more sites and is present in one or more copies. In some embodiments, the nucleic acid construct comprises the xylose isomerase, xylitol dehydrogenase, and/or xylulokinase polynucleotide(s) and no promoter that is operatively linked to the xylose isomerase, xylitol dehydrogenase, and/or xylulokinase polynucleotide(s). This type of construct typically comprises genetic elements to facilitate integration into the fungal host chromosome at a location that is downstream of a native promoter (i.e., in the host chromosome). In some embodiments, a second nucleic acid comprising a promoter and genetic elements to facilitate integration into the fungal host chromosome in a location upstream of the targeted integration site of the xylose isomerase, xylitol dehydrogenase, and/or xylulokinase polynucleotide finds use. In some embodiments, the nucleic acid construct comprises the xylose isomerase, xylitol dehydrogenase, and xylulokinase polynucleotides operatively linked to a promoter or promoter and terminator sequences such that all are integrated into the host chromosome (genome). It is contemplated that any suitable element that facilitates integration will find use in the present invention.

Genetic elements that facilitate integration by homologous recombination include those having sequence homology to targeted integration sites in the fungal host chromosome (genome). Suitable sites that find use as targets for integration include, but are not limited to the TY1 loci, the RDN loci, the ura3 locus, the GPD locus, aldose reductase (GRE3) locus, etc. Those having ordinary skill in the art will appreciate that additional sites for integration can be readily identified using methods known in the art, including but not limited to microarray analysis, metabolic flux analysis, comparative genome hybridization analysis, etc.

Genetic elements or techniques that facilitate integration by non-homologous recombination include, but are not limited to restriction enzyme-mediated integration (REMI) (See e.g., Manivasakam et al., Mol. Cell Biol., 18(3):1736-1745 [1998], incorporated herein by reference), transposon-mediated integration, and other elements and methods that are well known in the art. Indeed, any suitable method that facilitates homologous and/or non-homologous recombination finds use in the present invention.

In some embodiments, the nucleic acid constructs of the present invention comprise at least one further recombinant polynucleotide that is capable of conferring a desired phenotype to a fungal host cell, particularly in the context of xylose fermentation. In some embodiments, the recombinant polynucleotide that is capable of conferring an improved phenotype to the fungal host cell is a non-coding polynucleotide (e.g., a regulatory polynucleotide), a coding polynucleotide, or combination thereof.

Exemplary further desired phenotypes include, but are not limited to increased transport of xylose into the host cell, increased xylulokinase activity, increased xylitol dehydrogenase activity, increased xylose isomerase activity, increased xylose reductase activity, increased flux through the pentose phosphate pathway, decreased sensitivity to catabolite repression, increased tolerance to ethanol, increased tolerance to increased osmolarity, increased tolerance to organic acids, reduced production of by-products, and other similar properties related to increasing flux through the pentose phosphate and glycolysis pathways to produce a desired metabolic product/intermediate at higher levels as compared to the corresponding wild-type host cell. In some embodiments, the desired metabolic product is an alcohol (e.g., ethanol).

In some embodiments, nucleic acid constructs comprising at least one further polynucleotide that is capable of conferring a desired phenotype to a fungal host cell comprise a polynucleotide encoding a protein known to impact the desired phenotype, wherein the polynucleotide is either native or heterologous to the fungal host cell. In some embodiments, this polynucleotide is operatively linked to its native promoter, or to a heterologous promoter (i.e., a promoter that is not associated with the polynucleotide in the corresponding native gene). In some embodiments, at least one further polynucleotide is overexpressed. In some additional embodiments, the nucleic acid constructs comprise multiple copies of a least one polynucleotide. Suitable polynucleotides include, but are not limited to those that facilitate overexpression of proteins known to have an impact on the desired phenotype.

Exemplary recombinant polynucleotides that are capable of conferring a desired phenotype to a fungal host cell include, but are not limited to recombinant polynucleotides (either wild-type or mutated forms) that encode a xylose and/or hexose transporter, xylose reductase, at least one enzyme from the pentose phosphate pathway, at least one glycolytic enzyme (i.e., from the glycolytic metabolic pathway, at least one ethanologenic enzyme, regulatory sequences that enhance expression of these sequences, and/or combinations thereof. Additional recombinant polynucleotides (either wild-type or mutated forms) that find use in the present invention include, but are not limited to those that encode additional proteins involved in the pentose phosphate, glycolysis, and ethanologenic pathways, used alone or in combination in various embodiments of the present invention.

In some embodiments, transporter proteins find use in the present invention. Exemplary transporters include, but are not limited to GXF1, SUT1 and At6g59250 from *Candida intermedia*, *Pichia stipitis* and *Arabidopsis thaliana*, respectively (See e.g., Runquist et al., Biotechnol. Biofuels, 3:5 [2010], incorporated herein by reference), as well as HXT4, HXT5, HXT7, GAL2, AGT1, GXF2 (See e.g., Matsushika et al., Appl. Microbiol. Biotechnol. 84:37-53 [2009], incorporated herein by reference). In some embodiments, overexpression of native *S. cerevisiae* transporters is desirable, particularly HXT5 and HXT7.

In some embodiments, additional recombinant polynucleotides find use, including but not limited to those that encode: xylulose reductase (XR); an enzyme from the pentose phosphate pathway (e.g., a ribulose-5-phosphate 3-epimerase (RPE1), ribose-5-phosphate ketol-isomerase (RK11), transketolase (TKL1), transaldolase (TAL1), etc.); glycolytic enzyme(s) (e.g., a hexokinase (HXK1/HXK2), glyceraldehyde-3-phosphate dehydrogenase (GAPDH), pyruvate kinase (PVK2), etc.); and/or at least one ethanologenic enzyme (e.g., pyruvate decarboxylase, alcohol dehydrogenase, etc.).

In some embodiments of the present invention, regulatory polynucleotides find use. Exemplary regulatory polynucleotides include promoters, enhancers, terminators, and any other suitable regulatory element that functions to improve the expression of polynucleotides in a fungal host cell, particularly, a yeast host cell. These polynucleotides include, but are not limited to the regulatory elements described hereinabove.

The nucleic acid constructs described herein are useful for transforming fungal host cells to confer to these cells the property of xylose utilization.

Recombinant Fungal Host Cells

The present invention provides a recombinant fungal host cell comprising at least one xylose isomerase, xylitol dehydrogenase, and/or xylulokinase polynucleotide provided herein. In some embodiments, the recombinant fungal host cell comprises at least one polynucleotide sequence that encodes a polypeptide capable of catalyzing the isomerization of D-xylose directly to D-xylulose. In some embodiments, the polynucleotide is selected from: (a) a polynucleotide that encodes a polypeptide comprising an amino acid sequence that is at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:2, 8, 10, 12, 14, 16, 18, 20, 22, and/or 24; and (b) a polynucleotide that hybridizes under stringent hybridization conditions to the complement of a polynucleotide encoding a polypeptide having the amino acid sequence of SEQ ID NOS:1, 7, 9, 11, 13, 15, 17, 19, 21, and/or 23; SEQ ID NO:3; and/or SEQ ID NO:5. In some embodiments, the polypeptide(s) comprises at least one substitution and/or other mutation. In all of these embodiments, the polypeptides exhibit the activity associated with their sequences (i.e., xylose isomerase, xylitol dehydrogenase, or xylulokinase).

In some embodiments, the recombinant fungal host cell comprises at least one polynucleotide sequence that encodes at least one polypeptide, wherein the polynucleotide is selected from: (a) a polynucleotide that encodes a polypeptide comprising an amino acid sequence that is at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identical to SEQ ID NO:2, 8, 10, 12, 14, 16, 18, 20, 22, and/or 24; SEQ ID NO:4; and/or SEQ ID NO:6; and (b) a polynucleotide that hybridizes under stringent hybridization conditions to the complement of a polynucleotide encoding a polypeptide having the amino acid sequence of SEQ ID NO:1, 7, 9, 11, 13, 15, 17, 19, 21, and/or 23; SEQ ID NO:3; and/or SEQ ID NO:5. In some embodiments, the polypeptide(s) comprises at least one substitution and/or other mutation. In all of these embodiments, the polypeptides exhibit the activity associated with their sequences (i.e., xylose isomerase, xylitol dehydrogenase, or xylulokinase).

In some embodiments, the present invention provides a recombinant fungal host cell comprising and/or transformed with a nucleic acid construct of the present invention. In some embodiments, the xylose isomerase, xylitol dehydrogenase, and/or xylulokinase polynucleotide is integrated into the host cell genome. In some embodiments, the xylose isomerase, xylitol dehydrogenase, and xylulokinase polynucleotide are integrated into the host cell genome. Typically, the recombinant fungal host cell is a filamentous fungal or yeast host cell. More typically, the recombinant fungal host cell is a yeast host cell.

The present invention also provides methods for producing a recombinant fungal host cell, wherein the method comprises: (a) providing at least one nucleic acid construct of the present invention, wherein the nucleic acid construct comprises at least one xylose isomerase polynucleotide, at least one xylitol dehydrogenase polynucleotide, and/or at least one xylulokinase polynucleotide provided herein; and (b) transforming a fungal host cell with the nucleic acid construct to produce a recombinant fungal host cell. In some embodiments, the xylose isomerase polynucleotide sequence, xylitol dehydrogenase polynucleotide sequence, and/or xylulokinase polynucleotide sequence is integrated into the host cell genome.

The present invention further provides methods for producing a recombinant fungal host cell, wherein the method comprises: (a) providing at least one nucleic acid construct of the present invention, wherein the nucleic acid construct comprises at least one xylose isomerase polynucleotide, at least one xylitol dehydrogenase polynucleotide, and at least one xylulokinase polynucleotide provided herein; and (b) transforming a fungal host cell with the nucleic acid construct to produce a recombinant fungal host cell. In some embodiments, the xylose isomerase polynucleotide sequence, xylitol dehydrogenase polynucleotide sequence, and xylulokinase polynucleotide sequence is integrated into the host cell genome.

Introduction of the expression construct of the present invention into the host cell can be accomplished using any suitable method, including but not limited to calcium phosphate transfection, DEAE-dextran mediated transfection, electroporation, or any other suitable technique. Indeed, there are numerous methods known in the art and described in various standard reference texts.

In some embodiments of the present invention, the fungal host cells include yeast and filamentous fungal host cells. In some additional embodiments, the fungal host cell is a yeast cell. Exemplary yeast host cells useful in the present invention include, but are not limited to Candida, Hansenula, Saccharomyces, Schizosaccharomyces, Pichia, Kluyveromyces, and Yarrowia. In some embodiments of the invention, the yeast cell is Hansenula polymorpha, Saccharomyces cerevisiae. Saccharomyces carlsbergensis, Saccharomyces diastaticus, Saccharomyces norbensis, Saccharomyces kluyveri, Schizosaccharomyces pombe, Pichia pastoris, Pichia finlandica, Pichia trehalophila, Pichia kodamae, Pichia membranaefaciens. Pichia opuntiae, Pichia thermotolerans, Pichia salictaria, Pichia quercuum, Pichia pijperi, Pichia stipitis, Pichia methanolica, Pichia angusta, Kluveromyces lactis, Candida albicans, or Yarrowia lipolytica. In some embodiments, the yeast host cell is Saccharomyces species. In some additional embodiments, the yeast host cell is Saccharomyces cerevisiae. However, it is not intended that the present invention be limited to any particular genus and/or species of yeast cells.

Yeast strains that find use in the present invention include, but are not limited to those available from various yeast collections, such as Lallemand (e.g., Lallemand 6469, Lallemand LYCC 6391, Lallemand LYCC 6939, Lallemand LYCC 6469, Lallemand LYCC 6469; all from Lallemand, Inc., Montreal, Canada); ARS (NRRL) Collection, U.S. Department of Agriculture (e.g., NRRL Y-1528, and YB-1952); and ATCC (e.g., BY4741, which is also available from other sources).

Suitable fungal host cells include, but are not limited to, Ascomycota, Basidiomycota, Deuteromycota, Zygomycota, and Fungi Imperfecti. The filamentous fungal host cells of the present invention include, but are not limited to all filamentous forms of the subdivision Eumycotina and Oomycota. Filamentous fungi are characterized by a vegetative mycelium with a cell wall composed of chitin, cellulose and other complex polysaccharides. In some embodiments, the filamentous fungal host cells of the present invention are morphologically distinct from yeast.

In some embodiments, the filamentous fungal host cell is a cell of a species of *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothia, Fusarium, Gibberella, Gliocladium, Humicola, Hypocrea, Myceliophthora, Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Trametes, Tolypocladium, Trichoderma, Verticillium, Volvariella*, or teleomorphs, or anamorphs, and synonyms, basonyms, and/or taxonomic equivalents thereof. However, it is not intended that the present invention be limited to any particular genus and/or species of filamentous fungal cells.

In some embodiments of the invention, the filamentous fungal host cell is of the *Aspergillus* species, *Ceriporiopsis* species, *Chrysosporium* species, *Corynascus* species, *Fusarium* species, *Humicola* species, *Neurospora* species, *Penicillium* species, *Tolypocladium* species, *Tramates* species, or *Trichoderma* species. However, it is not intended that the present invention be limited to any particular genus and/or species of filamentous fungal cells.

Additionally, exemplary filamentous fungal host cells that find use in the present invention include, but are not limited to a filamentous fungal host cell of *Trichoderma* (e.g., *T. longibrachiatum, T. viride* [e.g., ATCC 32098 and 32086], *T. reesei* [NRRL 15709, ATTC 13631, 56764, 56765, 56466, 56767, and RL-P37 and derivatives thereof; See e.g., Sheir-Neiss et al., Appl. Microbiol. Biotechnol., 20:46-53 [1984], incorporated herein by reference), *T. koningii*, and *T. harzianum*), as well as *Hypocrea jecorina*. The term "*Trichoderma*" refers to any fungal strain that was previously classified as *Trichoderma* or is currently classified as *Trichoderma*.

In some embodiments of the present invention, the filamentous fungal host cell is an *Aspergillus* species (e.g., *A. awamori, A. funigatus, A. japonicas, A. nidulans, A. niger. A. aculeatus, A. foetidus, A. oryzae. A. sojae*, or *A. kawachi* (See e.g., Kelly and Hynes, EMBO J., 4:475479 [1985]; NRRL 3112, ATCC 11490, 22342, 44733, and 14331; Yelton et al., Proc. Natl. Acad. Sci. USA, 81, 1480-1474 [1984]; Tilburn et al., Gene 26,205-221 [1982]; and Johnston et al., EMBO J., 4:1307-1311 [1985], all of which are incorporated herein by reference). In some embodiments of the invention, the filamentous fungal host cell is a *Fusarium* species (e.g., *F. bacterioides, F. cerealis, F. crookwellense, F. culmorum, F. graminaearum. F. gramninum, F. oxyporum. F. rosium*, or *F. venenatum*). In some embodiments of the invention, the filamentous fungal host cell is of a *Neurospora* species (e.g., *N. crassa*; See e.g., Case, et al., Proc. Natl. Acad. Sci. USA, 76:5259-5263 [1979]; U.S. Pat. No. 4,486,553; and Kinsey and Rambosek, Mol. Cell. Biol., 4:117-122 [1984], all of which are incorporated herein by reference). In some embodiments of the invention, the filamentous fungal host cell is of a *Humicola* species (e.g., *H. insolens. H. grisea*, or *H. lanuginosa*). In some embodiments of the invention, the filamentous fungal host cell is a *Mucor* species (e.g., *M. miehei* or *M. circinelloides*). In some embodiments of the invention, the filamentous fungal host cell is a *Rhizopus* species (e.g., *R. oryzae* or *R. niveus*). In some embodiments of the invention, the filamentous fungal host cell is of a *Penicillium* species (e.g., *P. purpurogenum, P. chrysogenum*, or *P. verruculosum*). In some embodiments of the invention, the filamentous fungal host cell is a *Thielavia* species (e.g., *T. terrestris*). In some embodiments of the invention, the filamentous fungal host cell is a *Tolypocladium* species (e.g., *T. inflatum* or *T. geodes*). In some embodiments of the invention, the filamentous fungal host cell is a *Trametes* species (e.g., *T. villosa* or *T. versicolor*). In some embodiments of the invention, the filamentous fungal host cell is a *Chrysosporium* species, (e.g., *C. lucknowense, C. keratinophilum. C. tropicum, C. merdarium, C. inops, C. pannicola*, or *C. zonatum*). In some embodiments of the invention, the filamentous fungal host cell is of the *Myceliophthora* species, e.g., *M. thermophila*.

Strains that find use in the present invention include those that are readily accessible to the public from a number of culture collections, including but not limited to the American Type Culture Collection (ATCC), Deutsche Sammlung von Mikroorganismen und Zellkutlturen GmbH (DSM), Centraalbureau Voor Schimmelcultures (CBS), and Agricultural Research Service Patent Culture Collection, Northern Regional Research Center (NRRL). Strains that find use in the present invention include those that are readily accessible to the public from any commercial source.

Recombinant fungal host cells of the present invention are capable of growth in a xylose-based culture medium (i.e., a culture medium where xylose is the primary carbon source). In these xylose-based culture media, the carbon source comprises xylose. In some xylose-based culture media, the carbon source consists of xylose. In some embodiments, the recombinant fungal host cell is capable of faster growth in a xylose-based culture medium as compared to the corresponding wild-type fungal host cell. In some embodiments, the recombinant fungal host cell is capable of faster growth in a xylose-based culture medium as compared to wild-type *Saccharomyces cerevisiae*. In some embodiments, the recombinant fungal host cell is capable of growth at a rate of at least about 0.2 per hour ($h^{-1}$) in a xylose-based culture medium, while in some other embodiments, the growth rate is at least about 0.3 or 0.4 per hour ($h^{-1}$). Growth rate can be determined using any suitable method, including optical density, cell counting methods, etc. Indeed, there are various well known methods for determining cell growth that find use in the present invention. Exemplary xylose-based culture media include culture media that have been formulated to contain xylose (See, the Examples herein), as well as feedstock obtained from a cellulosic saccharification process and/or feedstock from a hemicellulose pre-treatment process (i.e., a "hemicellulosic feedstock").

In some embodiments, recombinant fungal host cells of the present invention are also capable of fermenting xylose when provided with a xylose based culture medium. Typically, the recombinant fungal host cells described herein are capable of fermenting xylose at a faster rate compared to the corresponding wild-type fungal host cell. In some embodiments, the recombinant fungal host cells are capable of fermenting xylose at a rate of at least about 0.5 g/L/h, at least about 1 g/L/h, at least about 2 g/L/h, at least about 3 g/L/h, at least about 4 g/L/h, at least about 5 g/L/h, at least about 6 g/L/h, at least about 7 g/L/h, at least about 8 g/L/h, at least about 9 g/L/h, or at least about 10 g/L/h. In some embodiments the recombinant fungal host cells are capable of fermenting xylose at a rate of at least about 0.1 g/g CDW/h, at least about 0.15 g/g CDW/h, at least about 2 g/g CDW/h, at least about 0.25 g/g CDW/h, at least about 0.3 g/g CDW/h, at least about 0.4 g/g CDW/h, at least about 0.5 g/g CDW/h, at least about 0.6 g/g CDW/h, at least about 0.7 g/g CDW/h, at least about 0.75 g/g CDW/h, at least about 1 g/g CDW/h, at least about 1.25 g/g CDW/h, at least about 1.5 g/g CDW/h, at least about 1.75 g/g CDW/h, at least about 2 g/g CDW/h, at least about 2.25 g/g CDW/h, at least about 2.5 g/g CDW/h, at least about 2.75 g/g CDW/h, or at least about 3 g/g CDW/h. Exemplary xylose-based culture media include, but are not limited to culture media that have been formulated to contain xylose, as well as feedstock from cellulosic saccharification processes and/or feedstock from a hemicellulose pre-treatment process (i.e., a "hemicellulosic feedstock").

In some embodiments, the fungal host cell is a wild-type fungal cell, while in some other embodiments, it is a mutated or otherwise altered or engineered form of a wild-type fungal cell (i.e., a recombinant cell). In some embodiments, the fungal host cell (either wild-type or otherwise altered or engineered) comprises polynucleotides encoding xylose isomerase, xylitol dehydrogenase, xylulokinase, and one or more enzymes. In some embodiments, the additional enzyme is used in the pentose phosphate, glycolytic, and/or ethanologenic pathways. In some embodiments, the fungal host cell comprises polynucleotides encoding at least one xylose isomerase, xylitol dehydrogenase, and xylulokinase, and all or some of the enzymes in the pentose phosphate, glycolytic, and ethanologenic pathways. In some embodiments, the fungal host cell comprises recombinant polynucleotides encoding enzymes that are heterologous to the fungal host cell (i.e., not native to the fungal host cell). In some additional embodiments, the fungal host cell is engineered to comprise other metabolic pathways that utilize products/intermediates from the pentose phosphate, glycolytic, and/or ethanologenic pathways to produce other desirable products. For example, in some embodiments, the fungal host cell is engineered to comprise at least one metabolic pathway for the biosynthesis of a fatty alcohol or fatty acid (See e.g., WO 2007/136762, incorporated herein by reference). In some embodiments, the fatty alcohol or fatty acid is a C8-C20 fatty acid or fatty alcohol. In some embodiments, the fungal host cell is altered or engineered to overexpress any one or more of the polynucleotides encoding the enzymes in one or more of these metabolic pathways.

In some embodiments, the recombinant fungal host cell of the present invention further comprises genetic modifications to the xylose isomerase, xylitol dehydrogenase, and/or xylulokinase polynucleotide(s). In some embodiments, the recombinant host cell comprises at least one different recombinant polynucleotide that is capable of conferring a further desired phenotype to the fungal host cell. In some embodiments, the present invention provides a recombinant fungal host cell comprising at least one xylose isomerase, xylitol dehydrogenase, and xylulokinase polynucleotide and/or variant(s) thereof, and at least one recombinant polynucleotide that encodes a polypeptide that differs from the xylose isomerase, xylitol dehydrogenase, and xylulokinase or variant(s) thereof, wherein the recombinant polynucleotide imparts a desired phenotype to the fungal host cell. It is contemplated that in some embodiments, the recombinant polynucleotide that is capable of conferring a desired phenotype to the fungal host cell is introduced to the fungal host cell in the same nucleic construct as the xylose isomerase, xylitol dehydrogenase, and/or xylulokinase polynucleotide(s), while in some other embodiments, the recombinant polynucleotide that is capable of conferring a desired phenotype to the fungal host cell is introduced to the fungal host cell in a different nucleic construct as the xylose isomerase, xylitol dehydrogenase, and/or xylulokinase polynucleotide(s). Nucleic acid constructs of the present invention comprising a xylose isomerase, xylitol dehydrogenase and/or xylulokinase polynucleotide(s) and at least one further recombinant polynucleotide capable of conferring a desired phenotype to the fungal host cell are described above.

In some embodiments, the recombinant polynucleotide that is capable of conferring a desired phenotype to the fungal host cell is a non-coding polynucleotide (e.g., a regulatory polynucleotide), a coding polynucleotide, or a combination thereof. As described above, exemplary further desired phenotypes include, but are not limited to increased transport of xylose into the host cell, increased xylose reductase activity, increased xylitol dehygrogenase activity, increased xylulokinase activity, increased xylose isomerase activity, increased flux through the pentose phosphate pathway, decreased sensitivity to catabolite repression, increased tolerance to ethanol, increased tolerance to increased osmolarity, increased tolerance to organic acids, reduced production of by-products, and other like properties related to increasing flux through the pentose phosphate, glycolysis, and/or ethanologenic pathways to produce the desired metabolic product/intermediate at higher levels as compared to the corresponding wild-type host cell. In some embodiments, the desired metabolic product is an alcohol (e.g., ethanol).

In some embodiments, recombinant fungal host cells comprising at least one further polynucleotide capable of conferring a desired phenotype to the fungal host cell comprise at least one polynucleotide encoding a protein known to impact the desired phenotype, wherein the polynucleotide is either native or heterologous to the fungal host cell. In some embodiments, the polynucleotide(s) is/are operatively linked to the native promoter(s), while in some other embodiments, the polynucleotide is operatively linked to a heterologous promoter (i.e., one not associated with the polynucleotide in the corresponding native gene). In some embodiments, the polynucleotide is overexpressed. In some embodiments, the recombinant fungal host cell comprises multiple copies of the polynucleotide. Suitable polynucleotides include, but are not limited to those that facilitate overexpression of proteins known to have an impact on the desired phenotype. Therefore, in some embodiments, the fungal host cell is altered or engineered to overexpress one or more polynucleotides.

In some embodiments, recombinant polynucleotides that are capable of imparting a desired phenotype to a fungal host cell find use in the present invention include, but are not limited to recombinant polynucleotides that encode a xylose or hexose transporter, xylose reductase, at least one enzyme from the pentose phosphate pathway (See e.g., FIG. 2A), at least one glycolytic enzyme (i.e., from the metabolic pathway of glycolysis; See e.g., FIG. 2B), ethanologenic enzyme(s) (See e.g., FIG. 2C), regulatory sequences associated with any of these sequences, and any combination thereof.

As indicated above, exemplary transporters that find use in the present invention include, but are not limited to GXF1, SUT1 and At6g59250 from *Candida intermedia*, *Pichia stipitis*, and *Arabidopsis thaliana*, respectively (See e.g., Runquist et al., 84:37-53 [2010], incorporated herein by reference), HXT4, HXT5, HXT7, GAL2, AGT1, and GXF2, (See e.g., Matsushika et al., Appl. Microbiol. Biotechnol., 84:37-53 [2009]). In some embodiments, overexpression of native *S. cerevisiae* transporters is desirable, particularly HXT5 and HXT7.

Also as indicated, above, recombinant polynucleotides suitable for use in the present invention include, but are not limited to those that encode: xylose reductase (XR); at least one enzyme from the pentose phosphate pathway (e.g., a ribulose-5-phosphate 3-epimerase (RPE1), ribose-5-phosphate ketol-isomerase (RKI1), transketolase (TKL1), transaldolase (TAL1), etc.); at least one glycolytic enzyme (e.g., hexokinase (HXK1/HXK2), glyceraldehyde-3-phosphate dehydrogenase (GAPDH), pyruvate kinase (PVK2), etc.; and at least one ethanologenic enzyme (e.g., pyruvate decarboxylase, alcohol dehydrogenase, etc.).

As indicated above, exemplary regulatory polynucleotides that find use in the present invention include promoters, enhancer, terminator, and other regulatory elements that function to improve the expression of polynucleotides in a fungal host cell, particularly, a yeast host cell, as described above.

In some embodiments, recombinant host cells of the present invention comprise one or more native genes deleted from its genome. In some embodiments, the deletion(s) cause removal or reduction of a biological activity that is otherwise exhibited by the fungal host cell. In some embodiments, the cumulative effect of the deletion(s) also leads to an improvement in a phenotype of the fungal host cell. Any suitable method for deleting gene finds use in the present invention. There are numerous methods well known in the art. For example, in some embodiments, recombinant host cells of the present invention have certain native genes deleted from the host genome in order to improve the utilization of pentose sugars (e.g., xylose), increase transport of xylose into the host cell, increase xylose reductase activity, increase xylitol dehygrogenase activity, increase xylulokinase activity, increase xylose isomerase activity, increase flux through the pentose phosphate pathway, decrease sensitivity to catabolite repression, increase tolerance to ethanol/acetate, increase tolerance to increased osmolarity, increase tolerance to organic acids (low pH), reduce production of by-products, and other like properties related to increasing flux through the relevant pathways to produce ethanol and other desired metabolic products at higher levels, where comparison is made with respect to the corresponding host cell without the deletion(s). Genes targeted for deletion include, but are not limited to genes encoding enzymes in the pentose phosphate pathway, a glycolytic enzyme, and/or an ethanologenic enzyme, as well as any other gene, the deletion of which provides an advantage.

In some embodiments, other genes are targeted for deletion, including but not limited to those encoding aldose reductase (GRE3) (See e.g., Matsushika et al., Appl. Microbiol. Biotechnol., 84:37-53 [2009]), sorbitol dehydrogenases (SOR1/SOR2), glutamate dehydrogenase (GDH1), 6-phosphogluconate dehydrogenase (GND), glucose-5-phosphate dehydrogenase (ZWF1), and any enzyme for which its deletion is known in the art to improve the utilization of a pentose sugar, decrease by-product formation, and/or increase the ethanol yield of a fungal host cell. The genes encoding these enzymes in many fungi are known in the art. Those having ordinary skill in the art appreciate that additional genes encoding these and other enzymes of interest can be readily identified using various suitable techniques, such as by microarray analysis (See e.g., Sedlak et al., Yeast 21:671-684 [2004]), metabolic flux analysis (See e.g., Sonderegger et al., Appl. Environ. Microbiol., 70:2307-2317 [2004]), in silico modeling (See e.g., Hjersted et al., Biotechnol. Bioengineer. 97:1190-1204 [2007]), chemogenomics (See e.g., Teixeira et al., Appl. Environ. Microbiol., 75:5761-5772 [2009]), and other well known methods. Indeed, any suitable method finds use in the present invention.

In some embodiments, the host cells employed in the practice of the present invention are mutagenized and/or evolved to exhibit further desired phenotypes. For example, further improvements include, but are not limited to improvements in the utilization of pentose sugars (e.g., xylose, arabinose, etc.), increased transport of xylose into the host cell, increased xylulose kinase activity, increased xylose reductase activity, increased xylitol dehydrogenase activity, increased xylose isomerase activity, increased flux through the pentose phosphate pathway, decreased sensitivity to catabolite repression, increased tolerance to ethanol/acetate, increased tolerance to increased osmolarity, increased tolerance to organic acids (low pH), reduced production of by-products, and other like properties related to increasing flux through the pentose phosphate and glycolysis pathways to produce a desired metabolic product/intermediate at higher levels. In some embodiments, the desired metabolic product is an alcohol (e.g., ethanol). In some embodiments, the host cells are mutagenized and/or evolved using known methods either prior to or after transformation with one or at least one xylose isomerase, xylitol dehydrogenase, and xylulokinase polynucleotide. In some embodiments, the host cells are mutagenized and/or evolved using known methods either prior to or after transformation with one or at least one xylose isomerase, xylitol dehydrogenase, and/or xylulokinase polynucleotide. These methods include, but are not limited to classical mutagenesis, whole genome shuffling, evolutionary engineering methods, methods that employ screening and/or selection methods, and/or any combination of such well known methods.

Classical mutagenesis methods that find use in the present invention include, but are not limited to treatment of the host cell with a mutagen such as a chemical mutagen or irradiation exposure (e.g., ultraviolet or gamma-irradiation). Whole genome shuffling methods involving, for example, recombination of genomic DNA between native genomic DNA sequences and/or variants thereof, can be facilitated by sexual mating, protoplast fusion methods and other methods well known in the art (See e.g., WO 98/31837 and WO 2000/04190, incorporated herein by reference) also find use. In some embodiments, these methods are coupled with screening and/or selection methods to identify altered fungal host cells that exhibit the desired phenotype. For example, such methods find use in altering or engineering a fungal host cell to overexpress one or more desired polynucleotides. Indeed, any suitable method finds use in the present invention.

In some embodiments, evolutionary engineering is accomplished by prolonged cultivation and selection of strains under desired conditions through chemostat, turbidostat and/or batch cultures. Evolutionary engineering methods can be practiced under aerobic, microaerophilic or anaerobic conditions. Selection strategies can be optimized by varying culture conditions, for example, carbon source, nitrogen source, aeration, pH, temperature, etc. Methods for evolutionary engineering are well known in the art (See e.g., Wisselink et al., Appl. Environ. Microbiol., 75(4):907-914 [2009]; Kuyper et al., FEMS Yeast Res., 5:399-409 [2005]; and Sauer, Adv. Biochem. Engineer. Biotechnol., 73:129-169 [2001], all of which are incorporated herein by reference). Indeed, any suitable method finds use in the present invention.

In some embodiments of the present invention, the recombinant fungal host cell comprising a xylose isomerase, xylitol dehydrogenase and/or xylulokinase polynucleotide exhibits an improved phenotype relative to the corresponding fungal host cell without the xylose isomerase polynucleotide, xylitol dehydrogenase and/or xylulokinase polypeptide. In some embodiments, the recombinant fungal host cell comprises all three polynucleotides (i.e., xylose isomerase, xylitol dehydrogenase, and xylulokinase). In some embodiments, the improved phenotype comprises further improvement in the utilization of pentose sugars (e.g., xylose, arabinose, etc.), increased transport of xylose into the host cell, increased xylulose kinase activity, increased xylose reductase activity, increased xylitol dehydrogenase activity, increased xylose isomerase activity, increased flux through the pentose phosphate pathway, decreased sensitivity to catabolite repression, increased tolerance to ethanol/acetate, increased tolerance to increased osmolarity, increased tolerance to organic acids (low pH), and reduced production of by products, and/or other properties.

Enzyme Mixtures

In some embodiments, the present invention provides an enzyme mixture that comprises at least one xylose isomerase, xylitol dehydrogenase, and/or xylulokinase polypeptide as provided herein. In some embodiments, the present invention provides an enzyme mixture that comprises at least one xylose isomerase, xylitol dehydrogenase, and xylulokinase polypeptide as provided herein. In some embodiments, the enzyme mixture is cell-free (i.e., an enzyme mixture comprising enzymes that have been separated from cells), while in some alternative embodiments, the enzymes are not separated from the host cells that secrete at least one enzyme mixture component. Cell-free enzyme mixtures can be prepared by any of a variety of methodologies known in the art (e.g., filtration and/or centrifugation methodologies). In some embodiments, the enzyme mixtures are partially cell-free, substantially cell-free, or entirely cell-free.

In some embodiments, at least one xylose isomerase, xylitol dehydrogenase, xylulokinase, and any additional enzymes present in the enzyme mixture are secreted from a single genetically modified cell (e.g., a fungal host cell), while in some additional embodiments, at least one xylose isomerase, xylitol dehydrogenase, and xylulokinase, and any additional enzymes present in the enzyme mixture are secreted from different microbes in combined or separate fermentations. Similarly, in some additional embodiments, at least one xylose isomerase, xylitol dehydrogenase, and xylulokinase, and any additional enzymes present in the enzyme mixture are expressed individually or in sub-groups from different strains of different organisms and the enzymes are combined in vitro to make the enzyme mixture. It is also contemplated that the xylose isomerases and any additional enzymes in the enzyme mixture are expressed individually or in sub-groups from different strains of a single organism, and the enzymes combined to make the enzyme mixture. In some embodiments, all of the enzymes are expressed from a single host organism, such as a genetically modified fungal cell. In some embodiments, the enzymes described in WO 2011/041594, WO 2011/066457, WO 2011/14363, WO 2011/150318, WO 2012/024698, WO 2012/027282, WO 2010/148148, WO 2012/024662, WO 2012/044868, WO 2012/061432, US Pat. Appln. Publ. No. 2012/0003703, US Pat. Appln. Publ. No. 2012/0083019. US Pat. Appln. Publ. No. 2012/0077216, US Pat. Appln. Publ. No. 2012/0045793, US Pat. Appln. Publ. No. 2012/0088271, US Pat. Appln. Publ. No. 2012/0107881, and/or U.S. Pat. No. 8,143,050 (all of which are incorporated herein by reference), find use in the present invention.

In some embodiments, the enzyme mixture comprises at least one cellulase, selected from cellobiohydrolase (CBH), endoglucanase (EG), and/or beta-glucosidase (BGl) cellulases. Cellulase enzymes of the cellulase mixture work together in decrystallizing and hydrolyzing the cellulose from a biomass substrate to yield soluble sugars, such as but not limited to glucose (See e.g., Brigham et al. in Wyman ([ed.], *Handbook on Bioethanol*, Taylor and Francis, Washington D.C. [1995], pp 119-141, incorporated herein by reference). In some embodiments, the cellobiohydrolase is *T. reesei* cellobiohydrolase 11. In some embodiments, the endoglucanase comprises a catalytic domain derived from the catalytic domain of a *Streptomyces avermitilis* endoglucanase. In some embodiments, at least one cellulase is *Acidothermus cellulolyticus, Thermobifida fusca, Humicola grisea, Myceliophthora* (e.g., *M. thermophila*) and/or a *Chrysosporium* sp. cellulase. It is intended that the present invention encompass enzyme mixtures comprising any suitable cellulase obtained from any suitable source. It is not intended that the present invention be limited to any particular cellulase and/or cellulase source.

Cellulase mixtures for efficient enzymatic hydrolysis of cellulose are known (See e.g., Viikari et al., Adv. Biochem. Eng. Biotechnol., 108:121-45 [2007]; and US Pat. Publns. 2009/0061484; US 2008/0057541; and US 2009/0209009, each of which is incorporated herein by reference). In some embodiments, mixtures of purified naturally occurring or recombinant enzymes are combined with cellulosic feedstock or a product of cellulose hydrolysis. In some embodiments, one or more cell populations, each producing one or more naturally occurring or recombinant cellulases, are combined with cellulosic feedstock or a product of cellulose hydrolysis.

In some embodiments, at least one xylose isomerase, xylitol dehydrogenase, and/or xylulokinase polypeptide(s) of the present invention is present in mixtures comprising at least one additional enzyme other than cellulases that degrade cellulose, hemicellulose, pectin, and/or lignocellulose. In some embodiments, the enzyme mixtures comprise at least one xylose isomerase, xylitol dehydrogenase, and/or xylulokinase polypeptide(s) of the present invention, at least one cellulase, and at least one additional enzyme. In some embodiments, the enzymes comprise at least one xylanase, xylosidase, furanosidase, glucoronidase, esterase, acetylxylanesterase, feruloyl esterase, coumaroyl esterase, galactosidases, mannanases, mannosidases, pectinase, lyase, polygalacturonate lyase, galacturonase, pectin methyl esterase, galactanase, pectin acetyl esterase, pectin lyase, pectate lyase, rhamnosidase, polygalacturonate lyase, rhamnogalacturonanase, rhamnogalacturonan lyase, galacturonohydrolase, arabinase, lignin-degrading enzyme, laccase, peroxidase, lipase, protease, amylase, expansin, expansin-like protein, cellulose integrating protein, scaffoldin, scaffoldin-like protein, cellulose-induced protein or modulating protein, and/or any additional enzyme of interest. It is intended that the present invention encompasses any enzyme combination and any enzyme concentration(s). Indeed, it is not intended that the present invention be limited to any particular enzyme combination(s) and/or enzyme concentrations, as those of skill in the art know to produce useful enzyme combinations and concentrations as needed for their particular uses.

A "hemicellulase" as used herein, refers to a polypeptide that can catalyze hydrolysis of hemicellulose into small polysaccharides such as oligosaccharides, or monomeric saccharides. Hemicelluloses include xylan, glucuonoxylan, arabinoxylan, glucomannan and xyloglucan. Hemicellulases include, for example, the following: endoxylanases, b-xylosidases, a-L-arabinofuranosidases, a-D-glucuronidases, feruloyl esterases, coumarolyl esterases, a-galactosidases, b-galactosidases, b-mannanases, and b-mannosidases. In some embodiments, the present invention provides enzyme mixtures that comprise at least one xylose isomerase, xylitol dehydrogenase, and/or xylulokinase polypeptide(s) of the present invention and one or more hemicellulases.

In some additional embodiments, the present invention provides at least one xylose isomerase, xylitol dehydrogenase, and xylulokinase, and at least one endoxylanase. Endoxylanases (EC 3.2.1.8) catalyze the endohydrolysis of 1,4-β-D-xylosidic linkages in xylans. This enzyme may also be referred to as endo-1,4-β-xylanase or 1,4-β-D-xylan xylanohydrolase. In some embodiments, an alternative is EC 3.2.1.136, a glucuronoarabinoxylan endoxylanase, an enzyme that is able to hydrolyze 1,4 xylosidic linkages in glucuronoarabinoxylans.

In some additional embodiments, the present invention provides at least one xylose isomerase, xylitol dehydrogenase, and xylulokinase, and at least one β-xylosidase. β-xylosidases (EC 3.2.1.37) catalyze the hydrolysis of 1,4-β-D-xylans, to remove successive D-xylose residues from the non-reducing termini. This enzyme may also be referred to as xylan 1,4-β-xylosidase, 1,4-β-D-xylan xylohydrolase, exo-1,4-β-xylosidase or xylobiase.

In some additional embodiments, the present invention provides at least one xylose isomerase, xylitol dehydrogenase, and xylulokinase, and at least one α-L-arabinofuranosidase. α-L-arabinofuranosidases (EC 3.2.1.55) catalyze the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, arabinofuranosidase, polysaccharide alpha-L-arabinofuranosidase, alpha-L-arabinofuranoside hydrolase, L-arabinosidase and alpha-L-arabinanase.

In some additional embodiments, the present invention provides at least one xylose isomerase, xylitol dehydrogenase, and xylulokinase, and at least one alpha-glucuronidase. Alpha-glucuronidases (EC 3.2.1.139) catalyze the hydrolysis of an alpha-D-glucuronoside to D-glucuronate and an alcohol.

In some additional embodiments, the present invention provides at least one xylose isomerase, xylitol dehydrogenase, and xylulokinase, and at least one acetylxylanesterase. Acetylxylanesterases (EC 3.1.1.72) catalyze the hydrolysis of acetyl groups from polymeric xylan, acetylated xylose, acetylated glucose, alpha-napthyl acetate, and p-nitrophenyl acetate.

In some additional embodiments, the present invention provides at least one xylose isomerase, xylitol dehydrogenase, and xylulokinase, and at least one feruloyl esterase. Feruloyl esterases (EC 3.1.1.73) have 4-hydroxy-3-methoxycinnamoyl-sugar hydrolase activity (EC 3.1.1.73) that catalyzes the hydrolysis of the 4-hydroxy-3-methoxycinnamoyl (feruloyl) group from an esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase. FAEA, cinnAE, FAE-I, or FAE-II.

In some additional embodiments, the present invention provides at least one xylose isomerase, xylitol dehydrogenase, and xylulokinase, and at least one coumaroyl esterase. Coumaroyl esterases (EC 3.1.1.73) catalyze a reaction of the form: coumaroyl-saccharide+$H_2O$=coumarate+saccharide. In some embodiments, the saccharide is an oligosaccharide or a polysaccharide. This enzyme may also be referred to as trans-4-coumaroyl esterase, trans-p-coumaroyl esterase, p-coumaroyl esterase or p-coumaric acid esterase. The enzyme also falls within EC 3.1.1.73 so may also be referred to as a feruloyl esterase.

In some additional embodiments, the present invention provides at least one xylose isomerase, xylitol dehydrogenase, and xylulokinase, and at least one alpha-galactosidase. Alpha-galactosidases (EC 3.2.1.22) catalyze the hydrolysis of terminal, non-reducing α-D-galactose residues in α-D-galactosides, including galactose oligosaccharides, galactomannans, galactans and arabinogalactans. This enzyme may also be referred to as melibiase.

In some additional embodiments, the present invention provides at least one xylose isomerase, xylitol dehydrogenase, and xylulokinase, and at least one beta-galactosidase. Beta-galactosidases (EC 3.2.1.23) catalyze the hydrolysis of terminal non-reducing β-D-galactose residues in β-D-galactosides. In some embodiments, the polypeptide is also capable of hydrolyzing α-L-arabinosides. This enzyme may also be referred to as exo-(1→4)-β-D-galactanase or lactase.

In some additional embodiments, the present invention provides at least one xylose isomerase, xylitol dehydrogenase, and xylulokinase, and at least one beta-mannanase. Beta-mannanases (EC 3.2.1.78) catalyze the random hydrolysis of 1,4-β-D-mannosidic linkages in mannans, galactomannans and glucomannans. This enzyme may also be referred to as mannan endo-1,4-β-mannosidase or endo-1, 4-mannanase.

In some additional embodiments, the present invention provides at least one xylose isomerase, xylitol dehydrogenase, and xylulokinase, and at least one beta-mannosidase. Beta-mannosidases (EC 3.2.1.25) catalyze the hydrolysis of terminal, non-reducing β-D-mannose residues in β-D-mannosides. This enzyme may also be referred to as mannanase or mannase.

In some embodiments one or more enzymes that degrade pectin are included in enzyme mixtures that comprise at least one xylose isomerase, xylitol dehydrogenase, and xylulokinase of the present invention. A pectinase catalyzes the hydrolysis of pectin into smaller units such as oligosaccharide or monomeric saccharides. In some embodiments, the enzyme mixtures comprise any pectinase, for example an endo-polygalacturonase, a pectin methyl esterase, an endo-galactanase, a pectin acetyl esterase, an endo-pectin lyase, pectate lyase, alpha rhamnosidase, an exo-galacturonase, an exo-polygalacturonate lyase, a rhamnogalacturonan hydrolase, a rhamnogalacturonan lyase, a rhamnogalacturonan acetyl esterase, a rhamnogalacturonan galacturonohydrolase and/or a xylogalacturonase.

In some additional embodiments, the present invention provides at least one xylose isomerase, xylitol dehydrogenase, and xylulokinase, and at least one endo-polygalacturonase. Endo-polygalacturonases (EC 3.2.1.15) catalyze the random hydrolysis of 1,4-α-D-galactosiduronic linkages in pectate and other galacturonans. This enzyme may also be referred to as polygalacturonase pectin depolymerase, pectinase, endopolygalacturonase, pectolase, pectin hydrolase, pectin polygalacturonase, poly-α-1,4-galacturonide glycanohydrolase, endogalacturonase; endo-D-galacturonase or poly(1,4-α-D-galacturonide) glycanohydrolase.

In some additional embodiments, the present invention provides at least one xylose isomerase, xylitol dehydrogenase, and xylulokinase, and at least one pectin methyl esterase. Pectin methyl esterases (EC 3.1.1.11) catalyze the reaction: pectin+n H$_2$O=n methanol+pectate. The enzyme may also been known as pectin esterase, pectin demethoxylase, pectin methoxylase, pectin methylesterase, pectase, pectinoesterase or pectin pectylhydrolase.

In some additional embodiments, the present invention provides at least one xylose isomerase, xylitol dehydrogenase, and xylulokinase, and at least one endo-galactanase. Endo-galactanases (EC 3.2.1.89) catalyze the endohydrolysis of 1,4-β-D-galactosidic linkages in arabinogalactans. The enzyme may also be known as arabinogalactan endo-1,4-β-galactosidase, endo-1,4-β-galactanase, galactanase, arabinogalactanase or arabinogalactan 4-β-D-galactanohydrolase.

In some additional embodiments, the present invention provides at least one xylose isomerase, xylitol dehydrogenase, and xylulokinase, and at least one pectin acetyl esterase. Pectin acetyl esterases catalyze the deacetylation of the acetyl groups at the hydroxyl groups of GalUA residues of pectin.

In some additional embodiments, the present invention provides at least one xylose isomerase, xylitol dehydrogenase, and xylulokinase, and at least one endo-pectin lyase. Endo-pectin lyases (EC 4.2.2.10) catalyze the eliminative cleavage of (1→4)-α-D-galacturonan methyl ester to produce oligosaccharides with 4-deoxy-6-O-methyl-α-D-galact-4-enuronosyl groups at their non-reducing ends. The enzyme may also be known as pectin lyase, pectin transeliminase; endo-pectin lyase, polymethylgalacturonic transeliminase, pectin methyltranseliminase, pectolyase. PL, PNL or PMGL or (1→4)-6-O-methyl-α-D-galacturonan lyase.

In some additional embodiments, the present invention provides at least one xylose isomerase, xylitol dehydrogenase, and xylulokinase, and at least one pectate lyase. Pectate lyases (EC 4.2.2.2) catalyze the eliminative cleavage of (1→4)-α-D-galacturonan to produce oligosaccharides with 4-deoxy-α-D-galact-4-enuronosyl groups at their non-reducing ends. The enzyme may also be known polygalacturonic transeliminase, pectic acid transeliminase, polygalacturonate lyase, endopectin methyltranseliminase, pectate transeliminase, endogalacturonate transeliminase, pectic acid lyase, pectic lyase, α-1,4-D-endopolygalacturonic acid lyase. PGA lyase, PPase-N, endo-α-1,4-polygalacturonic acid lyase, polygalacturonic acid lyase, pectin trans-eliminase, polygalacturonic acid trans-eliminase or (1→4)-α-D-galacturonan lyase.

In some additional embodiments, the present invention provides at least one xylose isomerase, xylitol dehydrogenase, and xylulokinase, and at least one alpha-rhamnosidase. Alpha-rhamnosidases (EC 3.2.1.40) catalyze the hydrolysis of terminal non-reducing α-L-rhamnose residues in α-L-rhamnosides or alternatively in rhamnogalacturonan. This enzyme may also be known as α-L-rhamnosidase T, α-L-rhamnosidase N or α-L-rhamnoside rhamnohydrolase.

In some additional embodiments, the present invention provides at least one xylose isomerase, xylitol dehydrogenase, and xylulokinase, and at least one exo-galacturonase. Exo-galacturonases (EC 3.2.1.82) hydrolyze pectic acid from the non-reducing end, releasing digalacturonate. The enzyme may also be known as exo-poly-α-galacturonosidase, exopolygalacturonosidase or exopolygalacturanosidase.

In some additional embodiments, the present invention provides at least one xylose isomerase, xylitol dehydrogenase, and xylulokinase, and at least one exo-galacturonase. Exo-galacturonases (EC 3.2.1.67) catalyze a reaction of the following type: (1,4-α-D-galacturonide)n+H2O=(1.4-α-D-galacturonide)n-i+D-galacturonate. The enzyme may also be known as galacturan 1,4-α-galacturonidase, exopolygalacturonase, poly(galacturonate) hydrolase, exo-D-galacturonase, exo-D-galacturonanase, exopoly-D-galacturonase or poly(1,4-α-D-galacturonide) galacturonohydrolase.

In some additional embodiments, the present invention provides at least one xylose isomerase, xylitol dehydrogenase, and xylulokinase, and at least one exopolygalacturonate lyase. Exopolygalacturonate lyases (EC 4.2.2.9) catalyze eliminative cleavage of 4-(4-deoxy-α-D-galact-4-enuronosyl)-D-galacturonate from the reducing end of pectate (i.e. de-esterified pectin). This enzyme may be known as pectate disaccharide-lyase, pectate exo-lyase, exopectic acid transeliminase, exopectate lyase, exopolygalacturonic acid-trans-eliminase, PATE, exo-PATE, exo-PGL or (1→4)-α-D-galacturonan reducing-end-disaccharide-lyase.

In some additional embodiments, the present invention provides at least one xylose isomerase, xylitol dehydrogenase, and xylulokinase, and at least one rhamnogalacturonanase. Rhamnogalacturonanases hydrolyze the linkage between galactosyluronic acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

In some additional embodiments, the present invention provides at least one xylose isomerase, xylitol dehydrogenase, and xylulokinase, and at least one rhamnogalacturonan lyase. Rhamnogalacturonan lyases cleave α-L-Rhap-(1→4)-α-D-GalpA linkages in an endo-fashion in rhamnogalacturonan by beta-elimination.

In some additional embodiments, the present invention provides at least one xylose isomerase, xylitol dehydrogenase, and xylulokinase, and at least one rhamnogalacturonan acetyl esterase. Rhamnogalacturonan acetyl esterases catalyze the deacetylation of the backbone of alternating rhamnose and galacturonic acid residues in rhamnogalacturonan.

In some additional embodiments, the present invention provides at least one xylose isomerase, xylitol dehydrogenase, and xylulokinase, and at least one rhamnogalacturonan galacturonohydrolase. Rhamnogalacturonan galacturonohydrolases hydrolyze galacturonic acid from the non-reducing end of strictly alternating rhamnogalacturonan structures in an exo-fashion. This enzyme may also be known as xylogalacturonan hydrolase.

In some additional embodiments, the present invention provides at least one xylose isomerase, xylitol dehydrogenase, and xylulokinase, and at least one endo-arabinase. Endo-arabinanases (EC 3.2.1.99) catalyze endohydrolysis of 1,5-α-arabinofuranosidic linkages in 1,5-arabinans. The enzyme may also be known as endo-arabinase, arabinan endo-1,5-α-L-arabinosidase, endo-1,5-α-L-arabinanase, endo-α-1,5-arabanase; endo-arabanase or 1,5-α-L-arabinan 1.5-α-L-arabinanohydrolase.

In some additional embodiments, the present invention provides at least one xylose isomerase, xylitol dehydrogenase, and xylulokinase, and at least one enzyme that participates in lignin degradation in an enzyme mixture. Enzymatic lignin depolymerization can be accomplished by lignin peroxidases, manganese peroxidases, laccases and cellobiose dehydrogenases (CDH), often working in synergy. These extracellular enzymes are often referred to as "lignin-modifying enzymes" or "LMEs." Three of these enzymes comprise two glycosylated heme-containing peroxidases, namely lignin peroxidase (LIP), Mn-dependent peroxidase (MNP), and a copper-containing phenoloxidase laccase (LCC).

In some additional embodiments, the present invention provides at least one xylose isomerase, xylitol dehydrogenase, and xylulokinase, and at least one laccase. Laccases are copper containing oxidase enzymes that are found in many plants, fungi and microorganisms. Laccases are enzymatically active on phenols and similar molecules and perform a one electron oxidation. Laccases can be polymeric and the enzymatically active form can be a dimer or trimer.

In some additional embodiments, the present invention provides at least one xylose isomerase, xylitol dehydrogenase, and xylulokinase, and at least one Mn-dependent peroxidase. The enzymatic activity of Mn-dependent peroxidase (MnP) in is dependent on $Mn^{2+}$. Without being bound by theory, it has been suggested that the main role of this enzyme is to oxidize $Mn^{2+}$ to $Mn^{3+}$ (See e.g., Glenn et al., Arch. Biochem. Biophys., 251:688-696 [1986]). Subsequently, phenolic substrates are oxidized by the generated $Mn^{3+}$.

In some additional embodiments, the present invention provides at least one xylose isomerase, xylitol dehydrogenase, and xylulokinase, and at least one lignin peroxidase. Lignin peroxidase is an extracellular heme that catalyses the oxidative depolymerization of dilute solutions of polymeric lignin in vitro. Some of the substrates of LiP, most notably 3,4-dimethoxybenzyl alcohol (veratryl alcohol. VA), are active redox compounds that have been shown to act as redox mediators. VA is a secondary metabolite produced at the same time as LiP by ligninolytic cultures of *P. chrysosporium* and without being bound by theory, has been proposed to function as a physiological redox mediator in the LiP-catalyzed oxidation of lignin in vivo (See e.g., Harvey, et al., FEBS Lett., 195:242-246 [1986]).

In some additional embodiments, the present invention provides at least one xylose isomerase, xylitol dehydrogenase, and xylulokinase, and at least one protease and/or a lipase that participates in cellulose degradation.

As used herein, "protease" includes enzymes that hydrolyze peptide bonds (peptidases), as well as enzymes that hydrolyze bonds between peptides and other moieties, such as sugars (glycopeptidases). Many proteases are characterized under EC 3.4, and are suitable for use in the present invention. Some specific types of proteases include, cysteine proteases including pepsin, papain and serine proteases including chymotrypsins, carboxypeptidases and metalloendopeptidases.

As used herein, "lipase" includes enzymes that hydrolyze lipids, fatty acids, and acylglycerides, including phosphoglycerides, lipoproteins, diacylglycerols, and the like. In plants, lipids are used as structural components to limit water loss and pathogen infection. These lipids include waxes derived from fatty acids, as well as cutin and suberin.

In some additional embodiments, the present invention provides at least one xylose isomerase, xylitol dehydrogenase, and xylulokinase, and at least one expansin or expansin-like protein, such as a swollenin (See e.g., Salheimo et al., Eur. J. Biochem., 269:4202-4211 [2002]) or a swollenin-like protein. Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. In some embodiments, an expansin-like protein or swollenin-like protein comprises one or both of such domains and/or disrupts the structure of cell walls (such as disrupting cellulose structure), optionally without producing detectable amounts of reducing sugars.

In some additional embodiments, the present invention provides at least one xylose isomerase, xylitol dehydrogenase, and xylulokinase, and at least one polypeptide product of a cellulose integrating protein, scaffoldin or a scaffoldin-like protein, for example CipA or CipC from *Clostridium thermocellum* or *Clostridium cellulolyticum* respectively. Scaffoldins and cellulose integrating proteins are multifunctional integrating subunits which may organize cellulolytic subunits into a multi-enzyme complex. This is accomplished by the interaction of two complementary classes of domain (i.e. a cohesion domain on scaffoldin and a dockerin domain on each enzymatic unit). The scaffoldin subunit also bears a cellulose-binding module that mediates attachment of the cellulosome to its substrate. A scaffoldin or cellulose integrating protein for the purposes of this invention may comprise one or both of such domains.

In some additional embodiments, the present invention provides at least one xylose isomerase, xylitol dehydrogenase, and xylulokinase, and at least one cellulose-induced protein or modulating protein, for example as encoded by cip1 or cip2 gene or similar genes from *Trichoderma reesei* (See e.g., Foreman et al., J. Biol. Chem., 278:31988-31997 [2003]), *M. thermophila*, and/or any other suitable organism.

In some additional embodiments, the present invention provides at least one xylose isomerase, xylitol dehydrogenase, and xylulokinase, and at least one member of each of the classes of the polypeptides described above, several members of one polypeptide class, or any combination of these polypeptide classes to provide enzyme mixtures suitable for various uses.

Other Components of Xylose Isomerase/Xylitol Dehydrogenase/Xylulokinase Compositions In some embodiments, xylose isomerase, xylitol dehydrogenase, and xylulokinase polypeptides of the present invention are used in combination with other optional ingredients such as at least one buffer, surfactant, and/or scouring agent. In some embodiments, at least one buffer is used with at least one xylose isomerase, xylitol dehydrogenase, and xylulokinase polypeptides of the present invention (optionally combined with other enzymes) to maintain a desired pH within the solution in which the xylose isomerase, xylitol dehydrogenase, and xylulokinase are utilized. The exact concentration of buffer employed will depend on several factors which the skilled artisan can determine. Suitable buffers are well known in the art and any suitable buffer finds use in the present invention.

In some embodiments, at least one surfactant is used with at least one xylose isomerase, xylitol dehydrogenase, and xylulokinase of the present invention. Suitable surfactants include any surfactant compatible with the xylose isomerase(s), xylitol dehydrogenase(s), and xylulokinase(s), and any other enzymes present in the mixture. Exemplary surfactants include, but are not limited to anionic, non-ionic, and ampholytic surfactants. Suitable anionic surfactants include, but are not limited to, linear or branched alkylbenzenesulfonates; alkyl or alkenyl ether sulfates having linear or branched alkyl groups or alkenyl groups; alkyl or alkenyl sulfates; olefinsulfonates; alkanesulfonates, and the like. Suitable counter-ions for anionic surfactants include, but are not limited to alkali metal ions, such as sodium and potassium; alkaline earth metal ions, such as calcium and magnesium; ammonium ion; and alkanolamines having from 1 to 3 alkanol groups of carbon number 2 or 3. Ampholytic surfactants suitable for use in the practice of the present invention include, but are not limited to surfactants such as quaternary ammonium salt sulfonates, betaine-type ampholytic surfactants, and the like. Suitable nonionic surfactants include, but are not limited to polyoxalkylene ethers, as well as higher fatty acid alkanolamides or alkylene oxide adduct thereof, fatty acid glycerine monoesters, and the like. Mixtures of surfactants also find use in the present invention, as known in the art. Indeed, any suitable mixture of surfactants finds use in the present invention.

Fermentation

The present invention provides processes for producing fermentation products, wherein the method comprises: (a) providing the recombinant fungal cell of the present invention: (b) providing a fermentation medium comprising xylose; (c) contacting the fermentation medium with the recombinant fungal cell under conditions suitable for generating the fermentation product; and optionally (d) recovering the fermentation product. In some embodiments, the fermentation product is an alcohol (e.g., ethanol, butanol, etc.), a fatty alcohol (e.g., a C8-C20 fatty alcohol), a fatty acid (e.g., a C8-C20 fatty acid), lactic acid, 3-hydroxypropionic acid, acrylic acid, acetic acid, succinic acid, citric acid, malic acid, fumaric acid, an amino acid, 1,3-propanediol, ethylene, glycerol, and/or a β-lactam (e.g., cephalosporin). However, it is contemplated that other fermentation products will be produced using the methods of the present invention.

In some embodiments, the fermentation medium is feedstock from a cellulosic saccharification process and/or feedstock from a hemicellulose pre-treatment process. Such feedstocks include, but are not limited to carbohydrates (e.g., lignocellulose, xylans, cellulose, starch, etc.), other sugars (e.g., glucose, xylose, arabinose, etc.), and other compositions of fermentation media suitable for the growth of yeast and filamentous fungi are well known in the art and there are various reference texts that provide recipes for these media. Any suitable medium finds use in the present invention.

Fermentation conditions suitable for generating desired fermentation products are well known in the art and any suitable method finds use in the present invention. In some embodiments, the fermentation process is carried out under aerobic or microaerophilic (i.e., where the concentration of oxygen is less than that in air), or anaerobic conditions. In some embodiments, fermentation is conducted under anaerobic conditions (i.e., no detectable oxygen), or less than about 5, about 2.5, or about 1 mmol/L/h oxygen. In the absence of oxygen, the NADH produced in glycolysis cannot be oxidized by oxidative phosphorylation. Under anaerobic conditions, pyruvate or a derivative thereof may be utilized by the host cell as an electron and hydrogen acceptor in order to generate NAD+. In some embodiments of the present invention, when the fermentation process is carried out under anaerobic conditions, pyruvate is reduced to a fermentation product such as ethanol, butanol, lactic acid, 3-hydroxypropionic acid, acrylic acid, acetic acid, succinic acid, citric acid, malic acid, fumaric acid, an amino acid, 1,3-propanediol, ethylene, glycerol, and/or a β-lactam (e.g., a cephalosporin).

In some embodiments, the fermentation process is run at a temperature that is optimal for the recombinant fungal cell. For example, in some embodiments, the fermentation process is performed at a temperature in the range of from about 20° C. to about 42° C. In some embodiments, the process is carried out a temperature that is less than about 38° C., less than about 35° C., less than about 33° C., or less than about 38° C., but at least about 20° C., 22° C. or 25° C. However, in some embodiments, the temperature is much higher (e.g., up to 100° C. or greater). In some embodiments, recombinant host cells of the present invention are grown under batch or continuous fermentation conditions. Classical batch fermentation is a closed system, wherein the composition of the medium is set at the beginning of the fermentation and is not subject to artificial alterations during the fermentation. A variation of the batch system is a fed-batch fermentation, which also finds use in the present invention. In this variation, the substrate is added in increments as the fermentation progresses. Fed-batch systems are useful when catabolite repression is likely to inhibit the metabolism of the cells and/or where it is desirable to have limited amounts of substrate in the medium. Batch and fed-batch fermentations are common and well known in the art. Continuous fermentation is an open system where a defined fermentation generally maintains the culture at a constant high density where cells are primarily in log phase growth. Continuous fermentation systems strive to maintain steady state growth conditions. Methods for modulating nutrients and growth factors for continuous fermentation processes, as well as techniques for modulating nutrients and growth factors for continuous fermentation processes as well as techniques for maximizing the rate of product formation are well known in the art of industrial microbiology. It is intended that any suitable fermentation method will find use in the present invention.

The foregoing and other aspects of the invention may be better understood in connection with the following non-limiting examples.

EXPERIMENTAL

The present invention is described in further detail in the following Examples, which are not in any way intended to limit the scope of the invention as claimed.

In the experimental disclosure below, the following abbreviations apply: wrt (with regard to); pm (parts per million); M (molar); mM (millimolar), uM and µM (micromolar); nM (nanomolar); mol (moles); gm and g (gram); mg (milligrams); ug and µg (micrograms); L and l (liter); ml and mL (milliliter); cm (centimeters); mm (millimeters); um and µm (micrometers); sec. (seconds); min(s) (minute(s)); h(s) and hr(s) (hour(s)); U (units); MW (molecular weight); rpm (rotations per minute); ° C. (degrees Centigrade); DNA (deoxyribonucleic acid); RNA (ribonucleic acid); CDW (cell dry weight); HPLC (high pressure liquid chromatography); HMF (hydroxymethylfurfural); ARS (ARS Culture Collection or NRRL Culture Collection, Peoria, Ill.); Lallemand (Lallemand Ethanol Technology, Milwaukee, Wis.); Dualsystems (Dualsystems Biotech AG, Basel, Switzerland); Megazyme (Megazyme International Ireland, Ltd., Wicklow, Ireland); Dasgip (Dasgip Biotools, LLC, Shrewsbury, Mass.); Difco (Difco Laboratories, BD Diagnostic Systems, Detroit, Mich.); PCRdiagnostics (PCRdiagnostics, *E coli*

SRO, Slovak Republic); Agilent (Agilent Technologies, Inc., Santa Clara, Calif.); and Bio-Rad (Bio-Rad Laboratories, Hercules, Calif.).

The following media were used in the work described in the Examples below.

YPD:
- 10 g/L Yeast Extract
- 20 g/L Peptone
- 20 g/L Dextrose

YP[5.5%]G (YPD with 5.5% glucose):
- 10 g/L Yeast Extract (BD Difco Cat. No. 212750)
- 20 g/L Peptone (BD Difco Cat. No. 211677)
- 55 g/L Glucose YP[5.5%]G[3.0%]X (YPD with 5.5% glucose and 3% xylose):
- 10 g/L Yeast Extract (BD Difco Cat. No. 212750)
- 20 g/L Peptone (BD Difco Cat. No. 211677)
- 55 g/L Glucose
- 30 g/L Xylose SD Minimal Medium (also referred to as "synthetic medium," "minimal medium" and "defined minimal medium"):
- 6.7 g/L Yeast Nitrogen Base, without amino acids, with ammonium sulfate (Sigma Y0626)
- 2 g/L Synthetic Defined Mix (SD Complete, US Biological Cat. No. D9515)
- 3.06 g/L Sodium phosphate, monobasic (Sigma S8282)
- 0.804 g/L Sodium phosphate, dibasic (Sigma S7907)

Trace elements solution:
- 1.5 g/L EDTA
- 450 µg/L Zinc sulfate (Sigma 221376)
- 100 µg/L Manganese chloride (Sigma M3634)
- 30 µg/L Cobalt(II)chloride (Sigma 202185)
- 30 µg/L Copper(II)sulfate (Sigma C7631)
- 40 µg/L Disodiummolybdate (Sigma M1003)
- 450 µg/L Calcium chloride (Sigma C3881)
- 300 µg/L Iron(II)sulfate (Sigma F8048)
- 100 µg/L Boric acid (Sigma B0394)
- 10 µg/L Potassium iodide (US Bio P5000)

The following sequences find use in the present invention. SEQ ID NO:2 corresponds to a synthetic chimeric xylose isomerase polypeptide sequence ("Chimera 1") derived from various sources and SEQ ID NO:1 is the polynucleotide sequence encoding SEQ ID NO:2. SEQ ID NOS:7, 8, 9 and 10 are from *G. trabeum*, SEQ ID NOS: 11 and 12 are from *Orpinomyces*, SEQ ID NOS: 13 and 14 correspond to a xylose isomerase isolated from a cow's rumen, SEQ ID NOS:15 and 16 corresponds to a xylose isomerase isolated from a human gut. SEQ ID NO:17, 18, 19, and 20 correspond to xylose isomerases from *C. boidinii*, SEQ ID NOS:21 and 22 correspond to a xylose isomerase from *P. infestans*, and SEQ ID NOS:23 and 24 is from *B. hominus*; SEQ ID NO:4 corresponds to the xylitol dehydrogenase (XD) from *Pichia stipitis*, encoded by SEQ ID NO:3. SEQ ID NO:6 corresponds to the xylulokinase (XK) from *Saccharomyces cerevisiae* encoded by SEQ ID NO:5

Chimera 1:
(SEQ ID NO: 1)
```
ATGAAGAACTATTTCCCCAACGTCCCAGAAATTAAATACGAAGGTCCA

AACTCCACAAATCCTTTCGCTTTTAAATATTATGATGCTAATAAAGTA

GTCGCCGGTAAGACCATGAAGGAGCATTTGAGATTCGCTCTATCCTGG

TGGCACACTTTGTGTGCCGGTGGTGCTGATCCATTCGGAGTAACTACT
```
```
ATGGACAGGAGCTACGGTAACATTACCGACCCAATGGAACTAGCTAAG

GCCAAAGTTGATGCTGGTTTCGAACTGATGACTAAGCTGGGCATCGAG

TTCTTCTGCTTCCATGATGCCGACATTGCTCCAGAAGGTGACACCTTC

GAAGAGTCCAAGAAAAATCTGTTCGAGATTGTTGATTACATCAAGGAG

AAGATGGACCAAACCGGCATCAAGTTGTTATGGGGCACTGCTAACAAC

TTTAGTCACCCCAGGTTCATGCACGGTGCAGGAACTTCTCCTAGTGCC

GATGTTTTCGCTTATGCTGCTGCGAAAATAAAGAACGCTTTAGATGCG

ACCATCAAGTTGGGCGGTAGAGGTTATGTCTTTTGGGGTGGTAGAGAA

GGTTACGAGACCCTGCTGAATACTAACATGGGCTTAGAACTGGACAAC

ATGGCTAGGTTGATGAAGATGGCCGTTGAGTATGGTAGGTCTATTGGA

TTCAAAGGTGACTTCTACATCGAGCCTAAACCCAAGGAACCTATGAAG

CACCAGTACGACTTCGACACTGCTACCGTATTAGGTTTTTTAAGGCAG

TACGGGTTGGATAAAGACTTCAAATTGAACATCGAAGCCAATCACGCC

ACACTAGCAGGACACTCATTCCAGCATGAGTTACGTATTGCTAGTATT

AACGGTATGTTGGGTTCTGTTGATGCTAACCAAGGTGACGTATTGTTA

GGATGGGACACGGATCAATTCCCCACAAACATTTATGATACTACTATG

TGTATGTATGAGGTCATTAAAGCCGGTGGTTTCACAAATGGCGGCCTG

AACTTTGATGCTAAAGCTAGAAGAGGTTCATTCACGCCTGAAGATATT

TTCTATTCTTACATTGCTGGTATGGATGCTTTCGCGTTAGGGTTTAGA

GCAGCTCTTAAATTGATTGAAGACGGTAGAATTGACAAGTTTGTGGCT

GACAGGTATGCCTCTTGGAATACCGGTATTGGTGCAGATATTATTGCC

GGAAAAGCCGATTTTGCATCATTGGAAAAATATGCTTTGGAGAAAGGA

GAGGTTACCGCGTCATTGTCTTCTGGTAGACAAGAGATGCTGGAATCT

ATTGTCAACAACGTATTGTTTAGTTTGTAA
```

(SEQ ID NO: 2)
```
MKNYFPNVPEIKYEGPNSTNPFAFKYYDANKVVAGKTMKEHLRFALSW

WHTLCAGGADPFGVTTMDRTYGNITDPMELAKAKVDAGFELMTKLGIE

FFCFHDADIAPEGDTFEESKKNLFEIVDYIKEKMDQTGIKLLWGTANN

FSHPRFMHGAGTSPSADVFAYAAAKIKNALDATIKLGGRGYVFWGGRE

GYETLLNTNMGLELDNMARLMKMAVEYGRSIGFKGDFYIEPKPKEPMK

HQYDFDTATVLGFLRQYGLDKDFKLNIEANHATLAGHSFQHELRIASI

NGMLGSVDANQGDVLLGWDTDQFPTNIYDTTMCMYEVIKAGGFTNGGL

NFDAKARRGSFTPEDIFYSYIAGMDAFALGFRAALKLIEDGRIDKFVA

DRYASWNTGIGADIIAGKADFASLEKYALEKGEVTASLSSGRQEMLES

IVNNVLFSL
```

P. stipitis XD:
(SEQ ID NO: 3)
```
ATGACCGCTAATCCCTCTCTTGTTTTGAATAAGATTGACGACATTTCT

TTTGAAACTTACGATGCTCCCGAAATTAGCGAACCCACAGACGTTTTA

GTTCAAGTTAAAAAAACTGGTATCTGCGGTTCTGACATCCACTTCTAC

GCTCATGGAAGGATCGGCAACTTCGTCTTAACAAAGCCAATGGTTCTG

GGTCATGAAAGCGCGGGTACTGTTGTTCAAGTCGGTAAAGGTGTTACT
```

```
TCACTGAAGGTTGGTGATAACGTCGCAATCGAGCCCGGTATTCCATCT
AGGTTCAGTGATGAGTACAAATCTGGTCACTACAACCTGTGTCCACAC
ATGGCATTTGCTGCTACTCCCAATTCTAAAGAGGGTGAACCAAACCCA
CCAGGAACTCTATGTAAGTACTTCAAATCTCCAGAAGACTTCCTGGTT
AAGTTACCCGATCATGTTTCTTTGGAGTTGGGTGCTTTGGTCGAGCCA
CTATCTGTTGGGGTCCATGCTAGTAAATTAGGCTCCGTTGCATTTGGC
GATTACGTTGCTGTTTTTGGTGCTGGTCCAGTAGGATTACTGGCTGCC
GCTGTCGCTAAGACATTTGGTGCCAAGGGTGTGATTGTCGTTGATATA
TTTGACAACAAGCTGAAGATGGCCAAAGACATAGGTGCCGCTACACAT
ACCTTCAACTCCAAGACGGGAGGTAGTGAAGAATTGATCAAAGCCTTC
GGTGGTAATGTACCAAATGTTGTCTTGGAATGTACTGGGGCTGAACCA
TGTATTAAGCTAGGTGTTGATGCCATCGCACCAGGTGGTAGATTCGTG
CAAGTTGGTAATGCTGCTGGTCCCGTGTCCTTTCCCATAACAGTGTTC
GCTATGAAAGAACTTACTTTGTTTGGTTCATTTCGTTATGGTTTCAAC
GACTATAAGACAGCCGTGGGTATCTTTGATACTAACTACCAGAACGGT
AGAGAGAATGCTCCCATTGACTTTGAACAGCTTATCACGCACAGATAC
AAATTCAAAGACGCCATTGAAGCCTACGACCTAGTAAGAGCAGGTAAA
GGGGCTGTCAAGTGTTTGATTGATGGTCCAGAATAA
                                              (SEQ ID NO: 4)
MTANPSLVLNKIDDISFETYDAPEISEPTDVLVQVKKTGICGSDIHFY
AHGRIGNFVLTKPMVLGHESAGTVVQVGKGVTSLKVGDNVAIEPGIPS
RFSDEYKSGHYNLCPHMAFAATPNSKEGEPNPPGTLCKYFKSPEDFLV
KLPDHVSLELGALVEPLSVGVHASKLGSVAFGDYVAVFGAGPVGLLAA
AVAKTFGAKGVIVVDIFDNKLKMAKDIGAATHTFNSKTGGSEELIKAF
GGNVPNVVLECTGAEPCIKLGVDAIAPGGRFVQVGNAAGPVSFPITVF
AMKELTLFGSFRYGFNDYKTAVGIFDTNYQNGRENAPIDFEQLITHRY
KFKDAIEAYDLVRAGKGAVKCLIDGPE

S. cerevisiae xylulokinase:
                                              (SEQ ID NO: 5)
ATGCTGTGCTCCGTTATACAAAGGCAAACAAGAGAAGTATCCAACACT
ATGTCTTTAGATAGTTATTATCTAGGATTCGATTTAAGTACACAACAA
TTGAAATGTCTTGCTATAAACCAGGATCTAAAGATCGTCCATTCCGAA
ACTGTCGAGTTCGAGAAGGACTTACCACATTATCACACCAAGAAGGC
GTCTACATTCATGGTGACACCATCGAATGCCCAGTTGCTATGTGGTTA
GAAGCCCTGGATCTTGTCCTGTCCAAATATAGGGAGGCAAAGTTCCCA
CTGAACAAGGTCATGGCTGTTTCCGGTTCTTGTCAGCAGCATGGCTCC
GTCTACTGGTCATCACAGGCTGAATCTCTGTTAGAACAACTGAACAAG
AAGCCAGAGAAGGACCTGTTACACTACGTCTCCTCTGTTGCATTTGCC
AGACAAACTGCTCCTAATTGGCAAGACCATTCCACTGCTAAACAATGT
CAGGAGTTCGAAGAGTGTATTGGTGGACCAGAGAAAATGGCCCAGTTA
ACTGGTTCCCGTGCTCATTTCAGGTTCACAGGCCCACAAATCCTGAAG
ATTGCTCAGTTAGAACCAGAGGCTTATGAAAAGACTAAGACCATCTCT
```
-continued
```
TTGGTCTCTAATTTCTTAACTTCCATTCTGGTTGGTCACTTGGTCGAA
CTGGAAGAAGCTGATGCGTGTGGTATGAACCTGTACGACATCCGTGAG
AGGAAGTTCTCTGACGAACTGCTGCATCTTATCGACTCCTCCTCTAAG
GACAAGACCATCAGGCAGAAACTGATGAGGGCACCAATGAAGAACCTG
ATTGCCGGTACATTTGCAAGTACTTCATCGAAAAGTATGGCTTCAAC
ACCAACTGCAAAGTCTCCCCTATGACTGGCGATAACCTAGCCACCATT
TGTAGCTTGCCCTTAAGAAAAAACGATGTTCTTGTGTCTTTGGGTACT
TCCACAACCGTCTTGTTGGTTACCGACAAATATCACCCTTCACCAAAC
TACCACCTGTTCATCCACCCGACGTTGCCTAACCACTACATGGGCATG
ATCTGCTACTGCAATGGCAGTTTAGCAAGGGAAAGGATAAGGGACGAG
TTGAACAAGGAGAGGGAGAACAACTACGAGAAGACCAACGATTGGACC
CTGTTCAACCAAGCTGTCCTGGATGATAGCGAATCCTCCGAGAATGAA
CTGGGCGTTTACTTTCCACTAGGCGAGATCGTTCCATCTGTCAAGGCC
ATCAACAAGAGAGTAATCTTCAACCCCAAGACTGGCATGATCGAAAGG
GAAGTCGCCAAGTTCAAGGACAAGAGACATGACGCCAAGAACATCGTT
GAATCTCAAGCCTTATCTTGCCGTGTTAGGATTTCTCCCCTACTAAGC
GACTCCAATGCTTCTTCCCAGCAACGTTTGAACGAGGATACGATTGTT
AAATTCGACTACGACGAGAGTCCATTGAGAGACTACTTGAACAAACGT
CCTGAGAGGACATTCTTTGTTGGTGGCGCATCCAAGAACGATGCTATT
GTTAAGAAGTTTGCTCAGGTCATAGGAGCAACCAAAGGTAACTTTCGT
TTAGAAACTCCAAACTCATGCGCTTTAGGTGGTTGGTACAAGGCTATG
TGGTCTTTGTTGTATGATAGCAATAAAATCGCTGTTCCTTTCGACAAG
TTCCTAAACGATAACTTCCCTTGGCACGTCATGGAATCCATCAGCGAT
GTAGACAACGAGAATTGGGATAGATACAATTCTAAAATAGTTCCCTTG
TCTGAGTTAGAGAAGACCTTGATTTAA (SEQ ID NO: 6)
MLCSVIQRQTREVSNTMSLDSYYLGFDLSTQQLKCLAINQDLKIVHSE
TVEFEKDLPHYHTKKGVYIHGDTIECPVAMWLEALDLVLSKYREAKFP
LNKVMAVSGSCQQHGSVYWSSQAESLLEQLNKKPEKDLLHYVSSVAFA
RQTAPNWQDHSTAKQCQEFEECIGGPEKMAQLTGSRAHFRFTGPQILK
IAQLEPEAYEKTKTISLVSNFLTSILVGHLVELEEADACGMNLYDIRE
RKFSDELLHLIDSSSKDKTIRQKLMRAPMKNLIAGTICKYFIEKYGFN
TNCKVSPMTGDNLATICSLPLRKNDVLVSLGTSTTVLLVTDKYHPSPN
YHLFIHPTLPNHYMGMICYCNGSLARERIRDELNKERENNYEKTNDWT
LFNQAVLDDSESSENELGVYFPLGEIVPSVKAINKRVIFNPKTGMIER
EVAKFKDKRHDAKNIVESQALSCRVRISPLLSDSNASSQQRLNEDTIV
KFDYDESPLRDYLNKRPERTFFVGGASKNDAIVKKFAQVIGATKGNFR
LETPNSCALGGCYKAMWSLLYDSNKIAVPFDKFLNDNFPWHVMESISD
VDNENWDRYNSKIVPLSELEKTLI
```

Sequences of Eukaryotic XI Genes:
EUK.1.XI:

(SEQ ID NO: 7)
ATGGATGGCGACTTAGATCCTAAAGAATATTTTCCTGAAATTCCTAAA
ATAAAGTATGAAGGACCCGAATCTAAAAATCCAATGGCGTTTCATTAT
TATGATGCAGAAAAGGTGGTGATGGGTAAAAAGATGAAAGATTGGTTA
AGGTTCGCAATGTGTTGGTGGCACACACTATGTGCAGATGGCGCCGAC
CAATTTGGTGCTGGCACTAAGACATTCCCATGGAATGAAGGCTCAGAT
CCAATCGCGATAGCTAAACAAAAAGTAGACGCTGGTTTTGAAATAATG
CAAAAGCTGGGGATTGAATACTACTGCTTCCACGATGTGGATCTAGTG
TCTGAAGGGAATAGCGTTGAAGAGTATGAGGCTAACTTAAAGCAGGTA
GTTGCCTACTTGAAAGAAAAGCAACAACAAACGGGTATTAAACTGTTG
TGGTCTACCGCAATGTCTTCGGTAATAAGAGATACATGAATGGTGCT
TCTACAAACCCGGATTTCGATGTTGTCGCTAGAGCAATAGTGCAAATA
AAAAATGGTATGGATGCAGGGATTGAATTGGGAGCAGAAAATTATGTC
TTCTGGGGAGGAAGAGAAGGATATATGTCTTTATTGAATACTGACCAG
AAGAGAGAAAAGAACACATGGCTAGAATGCTTACTATGGCCAGAGAT
TACGCTAGAAGCAAGGGTTTTAAAGGTACGTTCTTAATCGAACCCAAA
CCCTGCGAGCCCTCTAAGCATCAGTATGATGTAGATACGGAAACTGTA
ATAGGCTTCCTGAGGGCTCACAATCTAGACAAAGATTTCAAGGTAAAT
ATCGAAGTCAACCACGCGACCCTTGCTGGACATACTTTTGAACACGAA
CTTGCGTGTGCAGTAGATGCGGGTATGTTAGGTAGCATAGACGCAAAT
AGAGGTGATTATCAGAATGGATGGGATACCGATCAGTTCCCTATTGAC
CAATACGAATTAGTACAAGCTTGGATGGAAATTATCAGGGGTGGCGGC
TTTACAACGGGCGGGACAAACTTTGATGCTAAAACCAGACGTAATTCT
ACTGACTTAGAGGATATTTTTATCGCTCATATAAGTGGTATGGACGCT
ATGGCACGTGCTTTGGAGAATGCCGCAAAGTTACTGGAGGAATCTCCA
ATCCCCAAGATGAAGAAGGAAAGATACGCTTCATTCGATTCTGGAATG
GGTAAAGATTTCGAGGATGGTAAGTTAACGCTAGAGCAGGTTTATGAG
TACGGGAAGAAGAATGGTGAACCGAAGGATACTTCTGGAAAACAAGAA
CTTTACGAGGCCATAGTAGCAATGTACGCTTAG (SEQ ID NO: 8)
MDGDLDPKEYFPEIPKIKYEGPESKNPMAFHYYDAEKVVMGKKMKDWL
RFAMCWWHTLCADGADQFGAGTKTFPWNEGSDPTAIAKQKVDAGFEIM
QKLGIEYYCFHDVDLVSEGNSVEEYEANLKQVVAYLKEKQQQTGIKLL
WSTANVFGNKRYNINGASTNPDFDWARAIVQIKNAMDAGTELGAENYV
FWGGREGYMSLLNTDQKREKEHMARMLTMARDYARSKGFKGTFLIEPK
PCEPSKHQYDVDTETVIGFLRAHNLDKDFKVNIEVNHATLAGHTFEHE
LACAVDAGMLGSIDANRGDYQNGWDTDQFPIDQYELVQAWMEIIRGGG
ETTGGTNEDAKTRRNSTDLEDIFIAHISGMDAMARALENAAKLLEESP
IPKMKKERYASFDSGMGKDFEDGKLTLEQVYEYGKKNGEPKDTSGKQE
LYEATVMAYA

EUK.2.XI:

(SEQ ID NO: 9)
ATGGATGGTGATTTAGATCCAAAAGAATATTTTCCAGAAATTCCTAAG
ATTAAATATGAAGGTCCTGAATCCAAAAATCCAATGGCTTTTCATTAT
TATGATGCAGAAAAAGTTGTGATGGGTAAAAAAATGAAAGATTGGTTA
AGATTCGCANTGTGTTGGTGGCACACATTATGTGCAGATGGTGCAGAC
CAATTTGGTGCTGGTACTAAGACTTTTCCATGGAATGAAGGTTCTGAT
CCAATCGCTATCGCTAAACAAAAAGTTGATGCTGGTTTTGAAATTATG
CAAAAGCTTGGGATTGAATACTACTGTTTCCACGATGTCGATTTAGTC
TCTGAAGGCAATTCCGTTGAAGAATATGAAGCTAACTTGAAGCAGGTT
GTTGCATACTTGAAAGAAAAGCAACAACAAACCGGTATTAAACTTTTG
TGGTCTACAGCCAATGTATTCGGTAATAAGAGATACATGAATGGTGCT
TCTACAAACCCTGATTTTGATGTTGTTGCTAGAGCTATTGTCCAAATT
AAAAATGCTATGGATGCTGGCATTGAATTGGGTGCTGAAAATTATGTA
TTTTGGGGTGGAAGAGAAGGTTATATGTCTTTGTTGAATACTGATCAA
AAGAGAGAAAAAGAACACATGGCTAGAATGCTAACTATGGCAAGAGAT
TACGCTAGATCCAAGGGTTTTAAAGGTACTTTTTTGATAGAACCTAAA
CCTTGCGAGCCTTCTAAACATCAGTATGATGTTGATACCGAAACTGTT
ATTGGTTTTTTAAGGGCTCACAATTTAGACAAAGATTTTAAGGTTAAT
ATCGAAGTTAATCACGCCACATTAGCTGGTCATACTTTTGAACACGAA
TTAGCCTGTGCTGTTGATGCCGGTATGTTGGGTTCCATAGATGCTAAT
AGAGGTGATTATCAAAATGGTTGGGATACAGATCAATTCCCAATTGAC
CAATATGAATTGGTTCAAGCTTGGATGGAAATTATCAGAGGTGGAGGT
TTTACAACGGGTGGGACAAACTTTGATGCTAAAACAAGGAGTTCTACT
GACTTAGAAGATATTTTTATCGCTCATATTTCAGGTATGGATGCTATG
GCTAGGGCTTTGGAGAATGCCGCATTACTGGAAGAATCTCCAATACCT
AAGATGAAGAAGGAAAGATACGCTTCTTTTGATTCTGGTATGGGTAAA
GATTTCGAAGATGGTAAGTTCTACCTTAGAACAAGTTTATGAATACGG
CAAAAAAAATGGTGAACCTAAGGATACTTCTGGTAAACAAGAATTATA
CGAAGCAATTGTTGCTATGTACGCTTAG (SEQ ID NO: 10)
MDGDLDPKEYFPEIPKIKYEGPESKNPIVIAMYYDAEKWIVIGKKMKD
WIRFAMCWWIITLCADGADQFGAGTKTFPWNEGSDPIAIAKQKVDAGF
EIMQKLGIEYYCFHDVDLVSEGNSVEEYEANLKQVVAYLKEKQQQTGI
KLLWSTANVFGNKRYMNGASTNPDFDVVARAIVQIKNAMPCEPSKHQY
DVDTETVIGFLRAHNLDKDFKVNIEVNHATLAGHTFEHELACAVDAGM
LGSIDANRGDYQNGWDTDQFPIDQYELVQAWMEHRGGGFTTGGTNFDA
KTRRNSTDLEDIFIAHISGMDAMARALENAAKLLEESPIPKMKKERYA
SFDSGMGKDFEDGKLTLEQVYEYGKKNGEPKDTSGKQELYEAIVAMYA

EUK.3.XI:

(SEQ ID NO: 11)
ATGACCAAAGAATACTTCCCAACTATAGGTAAAATTAGATTTGAAGGT
AAAGATAGCAAGAATCCAATGGCATTTCACTACTACGATGCAGAAAAA

GAAGTTATGGGCAAAAAGATGAAAGATTGGCTGAGGTTCGCAATGGCT
TGGTGGCACACACTTTGCGCAGATGGTGCAGATCAATTTGGCGTCGGT
ACTAAATCATTCCCATGGAACGAAGGTACAGATCCTATTGCTATCGCG
AAACAGAAGGTTGATGCAGGATTCGAAATTATGACTAAATTGGGGATA
GAGCATTACTGCTTTCATGATGTGGATCTTGTCTCCGAAGGGAACTCT
ATTGAAGAATATGAATCAAACTTGAAGCAAGTAGTTGCCTACTTGAAA
CAAAAGCAACAAGAAACGGGTATTAAACTGTTGTGGTCTACCGCGAAT
GTCTTCGGTAATCCAAGATACATGAATGGTGCAAGCACTAACCCTGAC
TTCGATGTGGTTGCACGTGCCATAGTTCAAATTAAGAACGCAATGGAT
GCAGGCATTGAGCTAGGTGCTGAAAATTATGTCTTCTGGGGAGGAAGA
GAAGGATATATGTCTTTATTGAATACTGACCAGAAGAGAGAAAAAGAA
CACATGGCTACTATGCTTACTATGGCCAGAGATTACGCTAGAAGCAAG
GGTTTTAAAGGTACGTTCTTAATCGAACCCAAACCCATGGAGCCCACG
AAACATCAGTATGACGTTGATACAGAAACGGTCATTGGATTCCTGCGT
GCCCACAACTTAGATAAAGATTTCAAAGTCAACATTGAAGTTAATCAT
GCGACCCTTGCTGGACATACTTTTGAACACGAACTTGCGTGTGCAGTA
GATGCGGGTATGTTAGGTAGCATAGACGCAAATAGAGGTGATTATCAG
AATGGATGGGATACCGATCAGTTCCCTATTGACCAATACGAATTAGTA
CAAGCTTGGATGGAAATTATCAGGGGTGGCGGCTTTGTAACGGGCGGG
ACAAACTTTGATGCTAAAACCAGACGTAATTCTACTGACTTAGAGGAT
ATTATTATCGCTCATATAAGTGGTATGGACGCTATGGCACGTGCTTTG
GAGAATGCCGCAAAGTTATTGCAAGAATCTCCATACTGTAATATGAAG
AAGGAGAGATACGCTTCATTCGATTCTGGAATCGGTAAAGATTTCGAG
GATGGTAAGTTAACGCTAGAGCAGGTTTATGAGTACGGGAAGAAGAAT
GGTGAACCGAAGGTCACTTCTGGAAAACAAGAACTTTACGAGGCCATA
GTAGCAATGTACCAATAA (SEQ ID NO: 12)
MTKEYFPTIGKIRFEGKDSKNPMAFHYYDAEKEVMGKKMKDWLRFAMA
WWHTLCADGADQFGVGTKSFPWNEGTDPIAIAKQKVDAGFEIMTKLGI
EHYCFHDVDLVSEGNSIEEYESNLKQVVAYLKQKQQETGIKLLWSTAN
VFGNPRYMNGASTNPDFDVVARAIVQIKNAMDAGIELGAENYVFWGGR
EGYMSLLNTDQKREKEHMATMLTMARDYARSKGFKGTFLIEPKPMEPT
KHQYDVDTETVIGFLRAHNLDKDFKVNIEVNHATLAGHTFEHELACAV
DAGMLGSIDANRGDYQNGWDTDQFPIDQYELVQAWMEIIRGGGFVTGG
TNFDAKTRRNSTDLEDIIIAHISGMDAMARALENAAKLLQESPYCNMK
KERYASFDSGIGKDFEDGKLTLEQVYEYGKKNGEPKVTSGKQELYEAI
VAMYQ

EUK.4.XI:
(SEQ ID NO: 13)
ATGGCAAAAGAATATTTCCCGTTTACAGGTAAAATCCCATTCGAAGGT
AAGGATTCAAAAAATGTCATGGCTTTTCACTACTACGAGCCGGAAAAA
GTGGTCATGGGCAAAAAAATGAAAGATTGGTTGAAATTCGCAATGGCA

TGGTGGCACACACTCTGGGAGGAGCAAGTGCAGATCAATTTGGCGGTCAA
ACCAGATCATACGAATGGGATAAGGCTGAATGTCCTGTTCAAAGAGCG
AAAGACAAGATGGACGCTGGATTCGAAATTATGGACAAGTTGGGTATT
GAATATTTTTGCTTTCATGACGTGGATCTTGTCGAGGAAGCGCCAACT
ATAGCTGAATACGAAGAAAGAATGAAGGCTATTACTGATTATGCTCAA
GAAAAGATGAAACTTTCCGAATATTAAATTGCTGTGGGGTACTGCTAA
TGTGTTTGGCAACAAAAGATACGCTAACGGCGCTTCTACTAACCCTGA
CTTTGATGTCGTTGCCAGAGCGATTGTACAAATAAAAAATAGCATTGA
TGCAACAATAAAGCTTGGCGGTACAAATTATGTCTTTTGGGGCGGAAG
GGAAGGTTATATGTCTTTATTGAATACTGACCAGAAGAGAGAAAAAGA
ACACATGGCTACTATGCTTGGTATGGCCAGAGATTACGCTAGAGCCAA
AGGTTTTAAAGGTACGTTCTTAATCGAACCCAAACCCATGGAGCCCTC
TAAGCATCAGTATGATGTAGATACGGAAACTGTAATAGGCTTCCTGAA
AGCTCATGGTCTGGATAAGGACTTTAAAGTTAATATCGAGGTGAATCA
CGCAACTCTTGCTGGTCATACATTCGAGCATGAACTTGCGTGTGCAGT
AGATGCGGGTATGTTAGGTAGCATAGACGCAAATAGAGGTGATGCGCA
GAATGGATGGGATACCGATCAGTTCCCTATTGACAATTTCGAATTAAC
ACAAGCTATGTTAGAGATCATAAGGAATGGCGGCTTGGGAAATGGGGG
CACGAACTTTGACGCTAAAATTAGACGTAATTCTACTGACTTAGAGGA
TTTATTTATCGCTCATATAAGTGGTATGGACGCTATGGCACGTGCTTT
GATGAACGCCGCAGACATCTTGGAAAACAGTGAATTGCCAGCCATGAA
GAAGGCTAGATACGCTAGTTTTGATTCCGGTATCGGCAAGGATTTCGA
GGATGGTAAACTAACTTTTGAGCAGGTGTACGAATATGGTAAAAAAGT
CGAAGAACCAAAACAAACCTCTGGAAAGCAGGAGAAGTATGAAACAAT
TGTTGCTCTACACTGTAAGTAG (SEQ ID NO: 14)
MAKEYFPFTGKIPFEGKDSKNVMAFHYYEPEKVVMGKKMKDWLKFAMA
WWHTLGGASADQFGGQTRSYEWDKAECPVQRAKDKMDAGFEIMDKLGI
EYFCFHDVDLVEEAPTIAEYEERMKAITDYAQEKMKQFPNIKLLWGTA
NVFGNKRYANGASTNPDFDVVARAIVQIKNSIDATIKLGGTNYVFWGG
REGYMSLLNTDQKREKEHMATMLGMARDYARAKGFKGTFLIEPKPMEP
SKHQYDVDTETVIGFLKAHGLDKDFKVNIEVNHATLAGHTFEHELACA
VDAGMLGSIDANRGDAQNGWDTDQFPIDNFELTQAMLEIIRNGGLGNG
GTNFDAKIRRNSTDLEDLFIAHISGMDAMARALMNAADILENSELPAM
KKARYASFDSGIGKDFEDGKLTFEQVYEYGKKVEEPKQTSGKQEKYET
IVALHCK

EUK.5.XI:
(SEQ ID NO: 15)
ATGGCGACTAAAGAGTACTTTCCAGGAATAGAAAAATTAAATTCGAA
GGTAAAGAGTCCAAGAATCCAATGGCTTTCAGATATTACGATGCGGAA
AAGGTAATAATGGGTAAAAAAATGAAGGATTGGCTGAAATTCTCCATG
GCATGGTGGCACACTCTGTGTGCAGAAGGTGGAGATCAATTTGGCGGC

```
GGTACTAAACATTTCCCATGGAACGGTGATGCTGACAAGTTACAAGCT
GCGAAAAACAAGATGGACGCTGGATTCGAATTTATGCAGAAGATGGGT
ATTGAATATTATTGTTTCCATGATGTGGATTTATGTGACGAAGCGGAC
ACTATTGAAGAATATGAAGCTAACTTGAAGGCTATTGTTGCCTACGCT
AAACAAAAGCAAGAAGAAACGGGTATTAAACTGTTGTGGGGCACTGCC
AACGTGTTTGGCCACGCTAGATACATGAATGGCGCCGCAACTAACCCT
GACTTTGATGTCGTTGCCAGAGCGGCTGTACAAATAAAAAATGCAATT
GATGCAACAATAGAGCTTGGCGGTTCCAATTATGTCTTTTGGGGCGGA
AGGGAAGGTTATATGTCTTTATTGAATACTGACCAGAAGAGAGAAAAA
GAACATTTGGCTCAAATGTTGACCATTGCTAGAGACTATGCCCGTGCT
AGAGGATTTAAGGGGACCTTCTTAATCGAACCCAAACCCATGGAGCCC
ACGAAACATCAGTATGACGTTGATACAGAAACGGTCGTTGGATTCCTG
AAAGCACATGGTCTGGATAAAGACTTTAAGGTCAACATTGAAGTTAAT
CATGCGACCCTTGCTGGACATACTTTTGAACACGAACTTGCCGGTCGCA
GTAGATAACGGGATGTTGGGCTCAATTGATGCGAACAGAGGTGACTAC
CAGAATGGTTGGGATACCGATCAGTTTCCTATTGACAATTATGACTCT
TACACAGGCCATGATGCAAATTATCAGAAACGGAGGTTTTGGTGACGG
GGGTACAAATTTTGATGCTAAAACGAGCTAGAAATTCAACCGACTTGG
AAGATATTTTCATTGCCCATATAGCAGGTATGGATGTTATGGCCAGGG
CTTTGGAATCCGCAGCTAAATTGTTAGAGGAATCTCCATATAAGAAAA
TGTTGGCTGACAGATACGCTTCATTCGATTCTGGAAAGGGTAAAGAAT
TTGAGGAAGGTAAGTTAACGCTAGAGGACGTTGTTGCGTACGCTAAGG
CTAATGGGGAGCCCAAACAAACTAGCGGCAAACAAGAATTGTATGAAG
CTATTGTAAACATGTATTGCTAG
                                        (SEQ ID NO: 16)
MATKEYFPGIGKIKFEGKESKNPMAFRYYDAEKVIMGKKMKDWLKFSM
AWWHTLCAEGGDQFGGGTKHFPWNGDADKLQAAKNKMDAGFEFMQKMG
IEYYCFHDVDLCDEADTIEEYEANLKAIVAYAKQKQEETGIKLLWGTA
NVFGHARYMNGAATNPDFDVVARAAVQIKNAIDATIELGGSNYVFWGG
REGYMSLLNTDQKREKEHLAQMLTIARDYARARGFKGTFLIEPKPMEP
TKHQYDVDTETVVGFLKAHGLDKDFKVNIEVNHATLAGHTFEHELAVA
VDNGMLGSIDANRGDYQNGWDTDQFPIDNYELTQAMMQIIRNGGFGDG
GGTNFDAKTRRNSTDLEDIFIAHIAGMDVMARALESAAKLLEESPYKK
MLADRYASFDSGKGKEFEEGKLTLEDVVAYAKANGEPKQTSGKQELYE
AIVNMYC
EUK.6.XI:
                                        (SEQ ID NO: 17)
ATGCCAGCCTACTTTGACCAATTAGATAGAGTTAGATTCGAAGGTACA
CAAAGCACAAATCCATTGGCCTTTAGACATTACAACCCCGATGAAATA
GTTCTAGGAAAAAGAATGGAAGACCACTTGAGATTTGCAGCCTGTTAT
TGGCATACCTTTTGTTGGAATGGTGCTGACATGTTTGGTATGGGTGCTT
TCGACAGACCATGGCAACAACCCGGTGAAGCACTGGCTTTAGCAAAAC

GTAAGGCGGATGTCGCGTTTGAATTTTTCCATAAGTTGAATGTGCCAT
ATTACTGTTTCCACGATGTTGACGTTTCCCCAGAAGGAGCTAGCCTAA
AAGAATATAAAAATAATTTCGCACAAATGGTCGATGTCTTAGCCGCTA
AACAGGAACAGTCTGGTGTTAAGCTTCTGTGGGGACTGCTAATTGTTT
TACCAATCCTCGTTATGGTGCAGGTGCGGCAACCAACCCAGACCCTGA
AGTTTTTAGCTGGGCAGCTACTCAAGTGGTTACTGCCATGGACGCTAC
TCATAAGTTGGGTGGAGAAAATTACGTTTTATGGGGAGGTAGAGAAGG
TTACGAAACCCTGTTGAATACGATTTAAGGCAGGAAAGAGAGCAAATT
GGAAGGTTCATGCAGCTGGTTGTAGAGCATAAACACAAGATAGGCTTC
CAGGGTACACTACTGATCGAACCTAAACCACAAGAACCGACCAAGCAT
CAATATGATTACGACGCTGCGACAGTCTATGGATTGTAAAGCAATTTG
GTTTGGAGAAGGAAATAAAGTTAAACATTGAAGCGAAGTATGCAACCT
TAGCAGGCCATTCTTTTCACCATGGCATAGCAACAGCCATAGCATTAG
GATTATTTGGTAGTGTTGATGCCAATAGGGGGGACGCCCAGCTTGGTT
GGGATACTGATCAGTTTCCAAATTCTGTTGAGGAAAACGCCTTAGTCA
TGTACGAGATTCTAAAGGCTGGCGGATTTACTACAGGAGGTTTGAACT
TTGACGCTAAGGTTAGGAGACAATCTACTGACAAATATGACTTGTTCT
ACGGTCATATCGGTGCTATGGATACAATGGCATTGTCTTTAAAAATAG
CAGCTAGAATGATAGAGGCTGGAGGTTTAGATCAAAGAGTCGCCAAAA
GATATGCCGGTTGGAATGGTGAGTTGGGACAACAAATATTAAAAGGGC
AGATGACGTTAACTGAAATAGCGCAGTACGCAGAACAACATAACCTTG
CCCCAGTTCATCAAAGCGGTCACCAGGAATTACTAGAGAATCTTGTTA
ATCATTACTTATTTGATAAGTGA
                                        (SEQ ID NO: 18)
MPAYFDQLDRVRFEGTQSTNPLAFRHYNPDEIVLGKRMEDHLRFAACY
WHTFCWNGADMFGMGAFDRPWQQPGEALALAKRKADVAFEFFHKLNVP
YYCFHDVDVSPEGASLKEYKNNFAQMVDVLAAKQEQSGVKLLWGTANC
FTNPRYGAGAATNPDPEVFSWAATQVVTAMDATHKLGGENYVLWGGRE
GYETLLNTDLRQEREQIGRFMQLVVEHKHKIGFQGTLLIEPKPQEPTK
HQYDYDAATVYGFLKQFGLEKEIKLNIEANYATLAGHSFHHGIATAIA
LGLFGSVDANRGDAQLGWDTDQFPNSVEENALVMYEILKAGGFTTGGL
NFDAKVRRQSTDKYDLFYGHIGAMDTMALSLKIAARMIEAGGLDQRVA
KRYAGWNGELGQQILKGQMTLTEIAQYAEQHNLAPVHQSGHQELLENL
VNHYLFDK
EUK.7.XI:
                                        (SEQ ID NO: 19)
ATGCCCTATTTCCCAGGTGTTGAAAAAGTTAGATTCGAAGGCCCTGCA
AGTACATCTGCACTAGCATTTAGACATTACGATGCGAATAAACTGATA
CTTGGAAAGCCAATGCGTGAACACTTGAGAATGGCAGCATGTTATTGG
CATACCTTTGTTTGGCCCGGTGCTGACATGTTTGGTATGGGTACTTTC
AAGAGACCATGGCAAAGAAGTGGAGAGCCAATGGAAGTAGCTATAGGG
AAGGCAGAAGCGGCTTTTGAGTTCTTCTCCAAACTAGGGATTGATTAT
```

-continued
```
TATAGCTTTCATGATACCGACGTTGCTCCTGAAGGATCTAGCCTAAAA
GAATATAGGAATCATTTCGCACAAATGGTCGATCATTTAGAAAGACAT
CAGGAACAGACCGGTATTAAGTTGCTTTGGGGGACAGCTAACTGCTTT
TCTAATCCAAGGTTTGCCGCAGGCGCAGCTTCAAATCCTGATCCTGAA
GTTTTCGCATTTGCAGCTGCGCAAGTCTTCAGCGCAATGAATGCTACA
TTGAGATTGAAAGGTGCTAATTATGTTTTGTGGGGTGGAAGAGAAGGT
TATGAGACTTTGCTGAACACTGATTAAAGAGAGAAAGGGAGCAATTG
GGTCGTTTTATGCGTATGGTTGTAGAGCATAAACACAAGATAGGCTTC
ACTGGTGATTTGCTGATCGAACCTTAAACCACAAGAACCGACCAAGCA
TCAATATGATTACGACTCAGCGACAGTCTTTGGATTCTTACACGAATA
TGGTTTGGAGCACGAAATAAAGGTTAACGTTGAAGCGAACCATGCAAC
CTTAGCAGGCCATTCTTTTCACCATGAAATAGCAACAGCCGTATCACT
AGGTATATTTGGGAGTATTGATGCCAATAGGGGGGACCCCCAGAATGG
GTGGGACACAGACCAATTTCGAAATTCTGTAGAAGAGATGACTTTAGC
CACATACGAAATTCTAAAGGCTGGCGGATTTAAGAATGGAGGATACAA
CTTTGATTCTAAGGTTAGGAGACAATCTTTAGACGAAGTGGACTTGTT
CCACGGTCATGTTGCAGCTATGGATGTACTAGCCTTGGCTCTAGAGAG
AGCTGCGGCTATGGTTCAAGATGACAGATTGCAACAATTTAAAGATCA
GAGATATGCAGGTTGGAGTCAGCCTTTAGGGCAGGCGGTATTAGCGGG
CGAGTTCTCCTTAGAAAGTCTTGCCGAACATGCTTTTGCCAACGCATT
AGACCCTCAAGCTGTATCTGGGCGTCAAGAAATGCTTGAGGGTGTTGT
TAACCGTTTTATTTAA
```
(SEQ ID NO: 20)
```
MPYFPGVEKVRFEGPASTSALAFRHYDANKLILGKPMREHLRMAACYW
HTFVWPGADMFGMTFKRPWQRSGEPMEVAIGKAEAAFEFFSKLGIDY
YSFHDTDVAPEGSSLKEYRNHFAQMVDHLERHQEQTGIKLLWGTANCF
SNPRFAAGAASNPDPEVFAFAAAQVFSAMNATLRLKGANYVLWGGREG
YETLLNTDLKREREQLGRFMRMVVEHKHKIGFTGDLLIEPKPQEPTKH
QYDYDSATVFGFLHEYGLEHEIKVNVEANHATLAGHSFHHEIATAVSL
GIFGSIDANRGDPQNGWDTDQFPNSVEEMTLATYEILKAGGFKNGGYN
FDSKVRRQSLDEVDLFHGHVAAMDVLALALERAAAMVQDDRLQQFKDQ
RYAGWSQPLGQAVLAGEFSLESLAEHAFANALDPQAVSGRQEMLEGVV
NRFI
```
EUK.8.XI:
(SEQ ID NO: 21)
```
ATGCAGCATCAAGTTAAAGAATATTTTCCAAACGTTCCAAAAATTACA
TTCGAGGGTCAAAACGCTAAATCCGTACTTGCATACAGAGAATACAAT
GCTTCAGAAGTTATCATGGGAAAGACTATGGAGGAATGGTGCAGGTTC
GCAGTTTGTTACTGGCATACCTTCGGCAATTCTGGCTCAGACCCATTC
GGTGGAGAAACCTATACTAATAGATTATGGAATGAGTCTTTAGAAAGA
GCGAATATATCTTCCAGGGAAAGATTGTTGGAAGCCGCAAAGTGCAAA
GCTGACGCAGCTTTTGAAACTTTTACGAAACTAGGTGTTAAGTATTAT
```

-continued
```
ACCTTTCATGACGTGGATTTAATTTCTGAGGGCGCTAACTTGGAGGAG
TCTCAGTCCCTGTTGGACGAGATATCTGATTATCTTCTTGATAAACAA
AATCAAACAGGGGTAAGATGCCTATGGGGTACTACCAATCTGTTCGGA
CATAGACGTTTTATGAATGGTGCTTCTACTAATCCAGATATGAAAGTT
TTTGCTCACGCCGCAGCTAGAGTTAAGAAGGCTATGGAGATTACCCTG
AAGTTGGGTGGACAAAACTTTGTGTTCTGGGGGGGTAGGGAGGGCTTC
CAGTCTATCTTAAATACAGATATGAAGACGGAATTGGATCACATGGCA
GCCTTCTTCAAGCTGGTGGTTGCATATAAAAAGGAACTGGGAGCTACC
TTCCAGTTTCTTGTTGAACCAAAGCCAAGGGAGCCCATGAAACACCAA
TATGATTACGATGCAGCTACGGTTGTCGCGTTCTTACACACTTATGGG
TTACAAAACGACTTCAAATTAAATATAGAACCAAATCATACAACCCTT
GCAGGCCATGATTACGAGCATGACATTTACTATGCCGCAAGTTACAAG
ATGCTAGGTTCTGTAGATTGTAACACGGGCGACCCGCTTGTTGGATGG
GACACTGATCAGTTTTTGATGGATGAAAAGAAAGCTGTCTTAGTCATG
AAGAAGATTGTAGAAATTGGCGGATTGGCTCCTGGAGGTTTGAACTTT
GACGCTAAGGTTAGACGTGAGTCTACTGACTTGGAGGATATCTTTATC
GCTCATATTGGTTCCATGGATTGTTTTGCCAGAGGTCTAAGACAAGCG
GCTAAGTTATTGGAAAAGAATGAATTGGGAGAATTGGTAAAGCAGAGA
TATGCATCTTGGAAAAGTACCTTAGGGGAGAGGATTGAACAGGGCCAG
GCGACATTAGAAGAAGTAGCCGCTTATGCAAAAGAAAGCGGTGAACCT
GACCACGTTAGTGGTAAGCAAGAACTTGCTGAATTGATGTGGTCAACT
GTTGCATTAGCTACAGGTATATGGCAGGATCATGTTACGTGTTCTCTT
ACAAAGAATTGGTGCTAG
```
(SEQ ID NO: 22)
```
MQHQVKEYFPNVPKITFEGQNAKSVLAYREYNASEVIMGKTMEEWCRF
AVCYWHTFGNSGSDPFGGETYTNRLWNESLERANISSRERLLEAAKCK
ADAAFETFTKLGVKYYTFHDVDLISEGANLEESQSLLDEISDYLLDKQ
NQTGVRCLWGTTNLFGHRRFMNGASTNPDMKVFAHAAARVKKAMEITL
KLGGQNFVFWGGREGFQSILNTDMKTELDHMAAFFKLVVAYKKELGAT
FQFLVEPKPREPMKHQYDYDAATVVAFLHTYGLQNDFKLNIEPNHTTL
AGHDYEHDIYYAASYKMLGSVDCNTGDPLVGWDTDQFLMDEKKAVLVM
KKIVEIGGLAPGGLNFDAKVRRESTDLEDIFIAHIGSMDCFARGLRQA
AKLLEKNELGELVKQRYASWKSTLGERIEQGQATLEEVAAYAKESGEP
DHVSGKQELAELMWSTVALATGIWQDHVTCSLTKNWC
```
EUK.9.XI:
(SEQ ID NO: 23)
```
ATGGAATATTTCCCAGGAATAAGTAATATCAAATATGAAGGGTCTGCG
TCAATGAATGATCTAAGTTTTAAATGGTATAATGCTGAACAAGTTGTT
TTAGGAAAGAAAATGAAGGACCATTTAAGATTTGCGGTTTGTTATTGG
CATACCTTTTGCTACCAAGGTAATGATCAATTCGGTGGACCTACTTTA
AACAGACCGTGGTGCGGTGATGCAGATCCAATGGTTGAAGCTAAAAAA
AAGTGTGATGCGGCTTTTGAGTTCTTCACGAAACTTGGCGTAGAATAC
```

-continued
```
TATTGCTTCCAGATAGAGATATCCTTTCTCCGAGGGTGAGACTCTTGA

AGAAACCAACAGGAGATTGGATGAAATCAGTGATTATATGCTGGAAAA

GCAAAAACAAACGGGTGTGTTATTATGGGGTACTGCTAACATGTTTGG

TGACCGTGTGTTTATGAACGGAGCTTCTACGAATCCTGATGCCCATGT

GTTTGCTTTAGCAGCAGCGCAGGTAAAAAAGGCTATGGACATTACAAA

AAAACTGGGAGGTGAAAATTATGTGTTTTGGGGTGGCAGAGAAGGTTA

CCAGTCTATTTTAAATTCTTTACCTGGTAAAGAATTAGACCACATGGG

TCAATTTATGCCTTATGGCTGTTGAATATAAGAAAAAGATAGGGGCTA

CGTTCCAACTTTTGATCGAGCCAAAACCTAGGGAGCCGACAAAACATC

AGTATGATTACGATGCACAAACTGTCATCGGTTTCCTGAGGAAATACG

GTCTTGAAAAGATTTCAAGTTAAATATTGAGCCCAATCACACGACAT

TAGCAGGTCACGATTATGAGCACGATATAGTTTTCGCTTGTAATGAGG

GTATGCTAGGCTCAGTAGATGCGAACACTGGAGATACCCTTCTGGGCT

GGGATACAGACCAGTTTCCAATGGACGTAAAGAAAGCCGTTATCGTGA

TGTACCATATTATAAGAGCAGGGGGCCTTCACTCAGGAGGTTTGAATT

TTGACGCTCACGTTAGGAGAGAATCTACCGATATGGAAGATAGATTTA

TTGCACACATTGGTGCTATGGACACTTTCGCTAGAGCATTGTTAATCG

TGGAGAAGATCATGAATGACAAAATTTATCAAGAAATGGTTGATAAAA

GATACGAGTCCTACACAACCGGTATTGGGGCCAGGATCGAAAATGGGG

AGGCTACTTTTGAAGAGTGTGAAAAATACATTCTGGAAAATGGTAAAC

CCGAACCTCAATCTGCTAAGCAAGAGAAATTCGAAATGTTATTAAATC

ATTACGTCTGA
```
(SEQ ID NO: 24)
```
MEYFPGISNIKYEGSASMNDLSFKWYNAEQVVLGKKMKDHLRFAVCYW

HTFCYQGNDQFGGPTLNRPWCGDADPMVEAKKKCDAAFEFFTKLGVEY

YCFHDRDIVAEGETLEETNRRLDEISDYMLEKQKQTGVKLLWGTANMF

GDRVFMNGASTNPDAHVFALAAAQVKKAMDITKKLGGENYVFWGGREG

YQSILNSLPGKELDHMGQFMRMAVEYKKKIGATFQLLIEPKPREPTKH

QYDYDAQTVIGFLRKYGLEKDFKLNIEPNHTTLAGHDYEHDIVFACNE

GMLGSVDANTGDTLLGWDTDQFPMDVKKAVIVMYHIIRAGGLHSGGLN

FDAHVRRESTDMEDRFIAHIGAMDTFARALLIVEKIMNDKIYQEMVDK

RYESYTTGIGARIENGEATFEECEKYILENGKPEPQSAKQEKFEMLLN

HYV
```

Example 1

Cloning the XI-XD-XK Pathway

Figure 8:
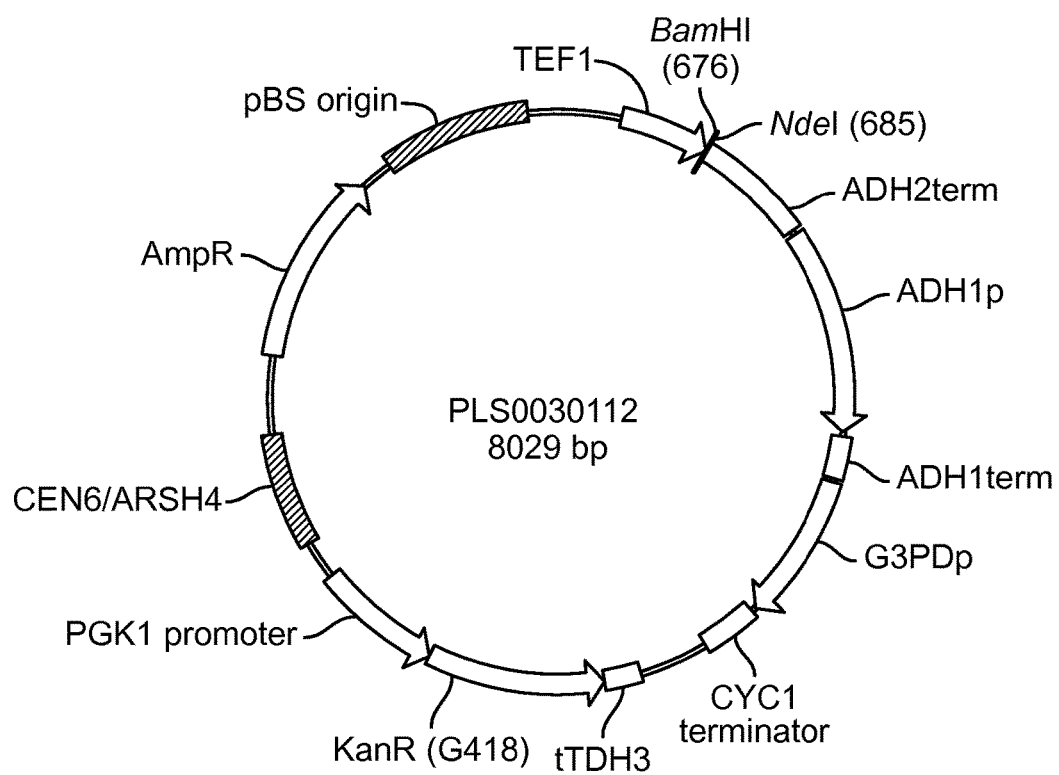
FIG. 8 provides a map of the plasmid PLS0030112.
Figure 9:
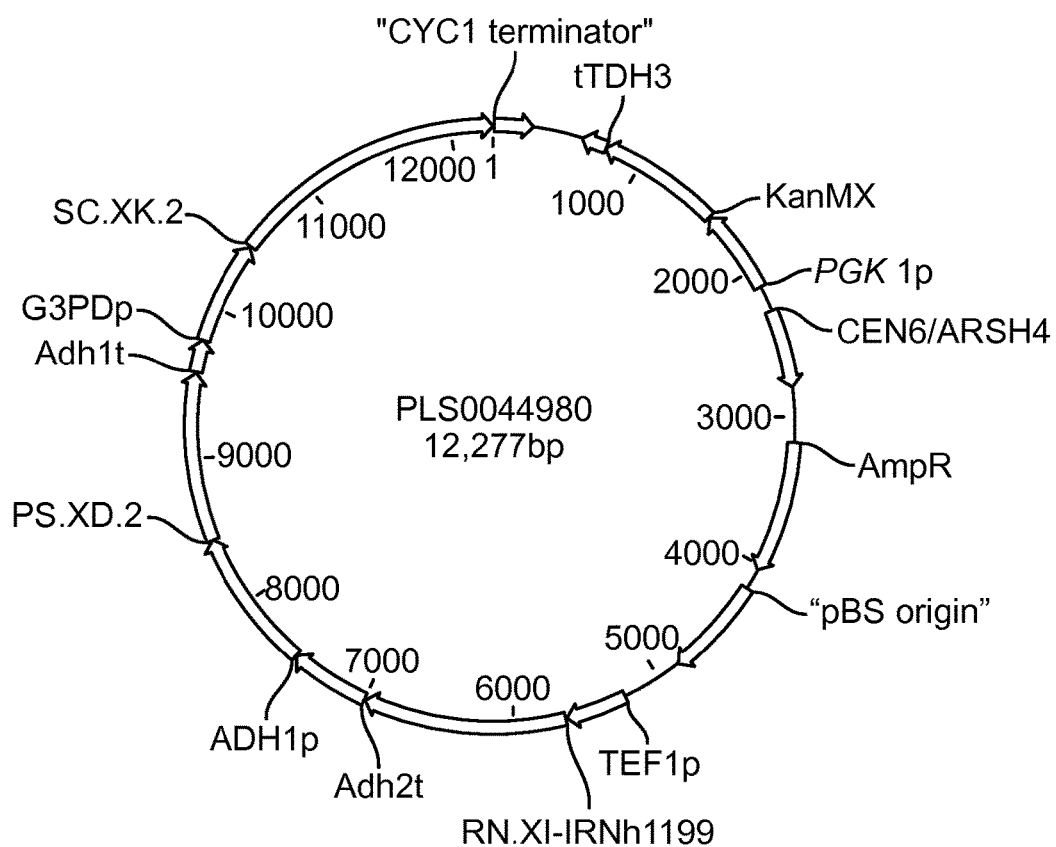
FIG. 9 provides a map of the plasmid PLS0044980.

The three genes, XI, XD and XK were cloned into the plasmid PLS0030112 (See, FIG. 8) using restriction enzymes (BamHI and NdeI for XI, SpeI and AatII for XD, NotI and XhoI for XK) and ligated. Each gene was cloned under different promoter (TEF1, ADH1, and G3PD, respectively) resulting in the plasmid PLS0044980 (See, FIG. 9). This plasmid was used to transform three yeast strains: Thermosacc® yeast (Lallemand), Thermosacc®-derived haploid progeny, and NRRL Y1528-derived haploid progeny. Transformation was performed based on the Sigma-Aldrich yeast transformation kit protocol and colonies were selected based on antibiotic resistance as observed by growth on YPD plates containing 200 ug/ml G418. In parallel experiments, these strains were also transformed with the control plasmids comprising the following gene combinations: XI only, XI+XD, XI+XK, XD+XK and a negative control (i.e., an empty vector).

Example 2

Characterization of Strains Containing the XI-XD-XK Pathway

Colonies grown on YPD with 200 ug/ml G418 were picked after 48 hours of growth in five replicates into 96-well plates filled with 400 ul of inoculation medium (YPD amended with 200 ug/ml G418, 1 mM MgSO$_4$ and trace elements solution as provided above) and were grown for 24 hours at 30° C. and 85% relative humidity, in a incubator-shaker at 2" throw and shaking speed of 250 RPM. After incubation, 80 ul of the culture were used to inoculate each well of a 96-deep well plate filled with 320 ul of YP[5.5%]G supplemented with 200 ug/ml G418, 1 mM MgSO$_4$ and the trace elements solution provided above. Strains were grown for an additional 24 hours under the same conditions. By the end of the propagation step, the plate was spun down (4000 RPM for ten minutes), and the cells were used to inoculate 400 ul YP[5.5%]G[3.0%]X amended with 200 ug/ml G418, 1 mM MgSO$_4$ and trace elements solution as provided above). The fermentation process was performed in cap-mat sealed 96-well plates at 30° C. and 85% relative humidity, in incubator-shakers with 2" throw and a shaking speed of 100 RPM. At the end of 96 hours, the plate was spun down (4000 RPM for ten minutes) and the supernatant was filtered and analyzed for metabolites by a HPLC using standard methods known in the art. In some experiments, the residual xylose in supernatant was measured using a spectrophotometric assay (e.g. Megazyme xylose assay; CAT No. K-XYLOSE) performed according to the manufacturer's protocol. The improvement in performance for xylose utilization was calculated based on a comparison with the performance of a control strain that was only transformed with the antibiotic marker.

Figure 3:
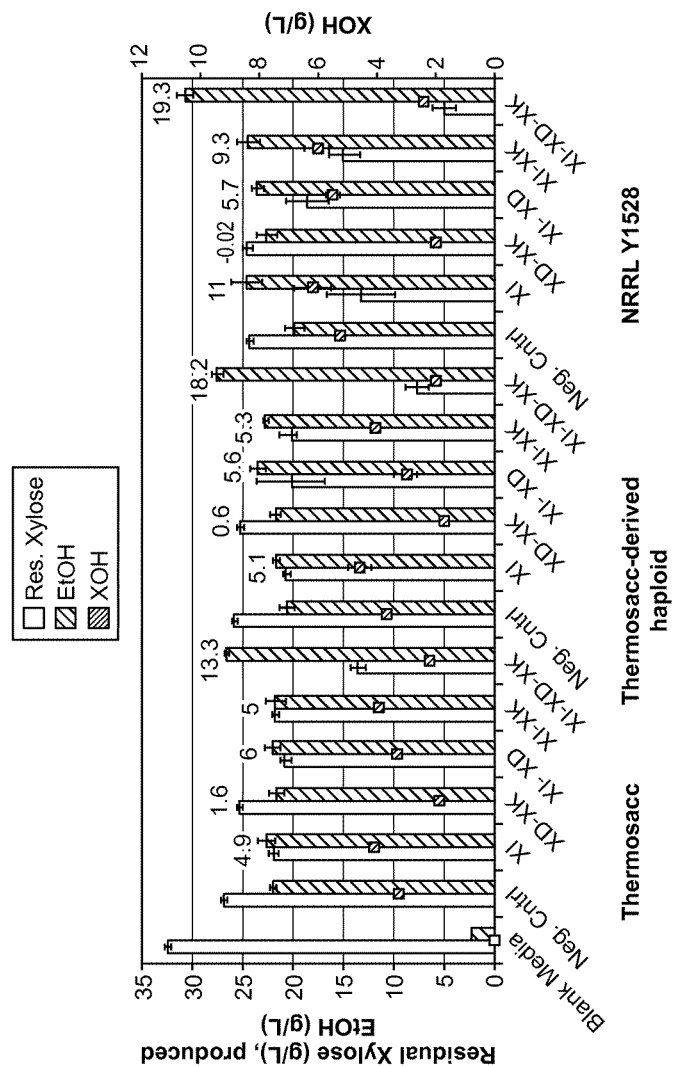
FIG. 3 provides a graph showing the fermentation results of strains comprising XI, XD and XK genes in different combinations. Fermentation performed in 96-well plates for 96 hours in YPD media supplemented with 30 g/l xylose. Residual xylose, as well as produced ethanol and xylitol are shown. Numbers in boxes represent xylose consumed in comparison with a control strain comprising an empty plasmid (n=7, error bars±SD).

FIG. 3 provides a graph showing the fermentation results. Fermentation analysis indicated a significant improvement in xylose consumption and ethanol production for all three strains comprising the XI-XD-XK pathways compared with the control strains comprising the XI gene only. While strains comprising XI in combination with XD or XK alone did not result in xylose utilization improvement, strains with the combined XI-XD-XK pathway achieved 2-3× fold higher xylose consumption than the corresponding parent strains comprising only XI. Moreover, these strains demonstrated lower xylitol (XOH) production, possibly due to the combined activity of XD and XK genes resulting in an increased in flux towards the pentose phosphate pathway (it is not intended that the present invention be limited to any specific mechanism and/or theory).

Figure 4:
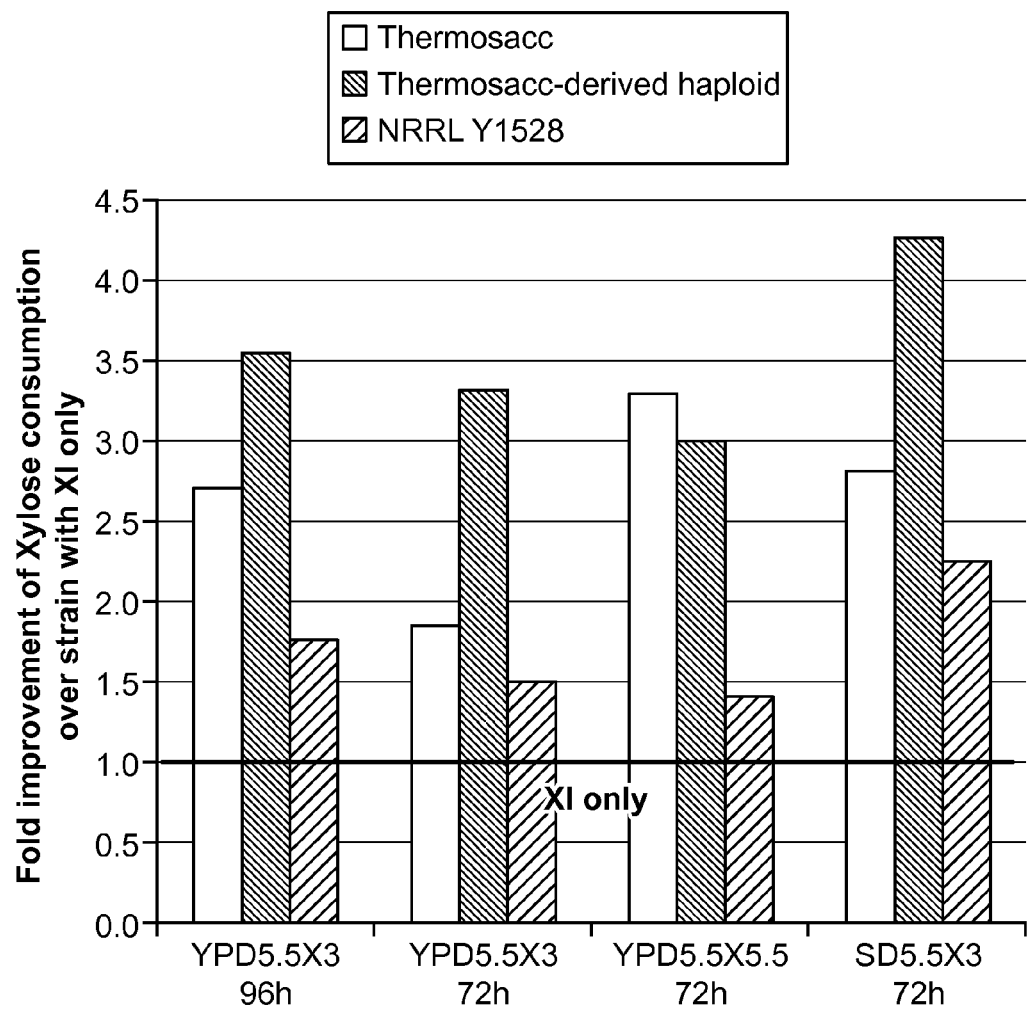
FIG. 4 provides a graph showing the fold improvement in xylose consumption under several fermentation conditions by different strains comprising the XI-XD-XK pathway relative to xylose consumption by the same strains comprising the XI gene only.

FIG. 4 provides a graph showing the fold improvement in xylose consumption by different strains tested under several fermentation conditions. Xylose consumption by strains comprising the XI-XD-XK pathway were compared to those only comprising the XI gene. Xylose consumption was calculated over the consumption measured from a reference strain comprising the empty plasmid. In this Figure, "YPD5.5X3" refers to YP[5.5%]G[3.0%]X medium, "YPD5.5X5.5" is YP[5.5%]G medium with 5.5% xylose, and "SD5.5X3" is SD minimal medium with 5.5% glucose and 3.0% xylose. The coefficients of variation were between 2-6%. As shown in FIG. 4, strains harboring the XI-XD-XK pathway maintained improved performance as observed by higher xylose consumption and corresponding ethanol production under a number of conditions, such as a fermentation time of 72 hours instead of 96 hours, xylose concentration of 5.5% instead of 3%, and minimal SD based media instead of YPD based media. The relative improvement was also observed when scaled up to 25 ml.

Figure 5:
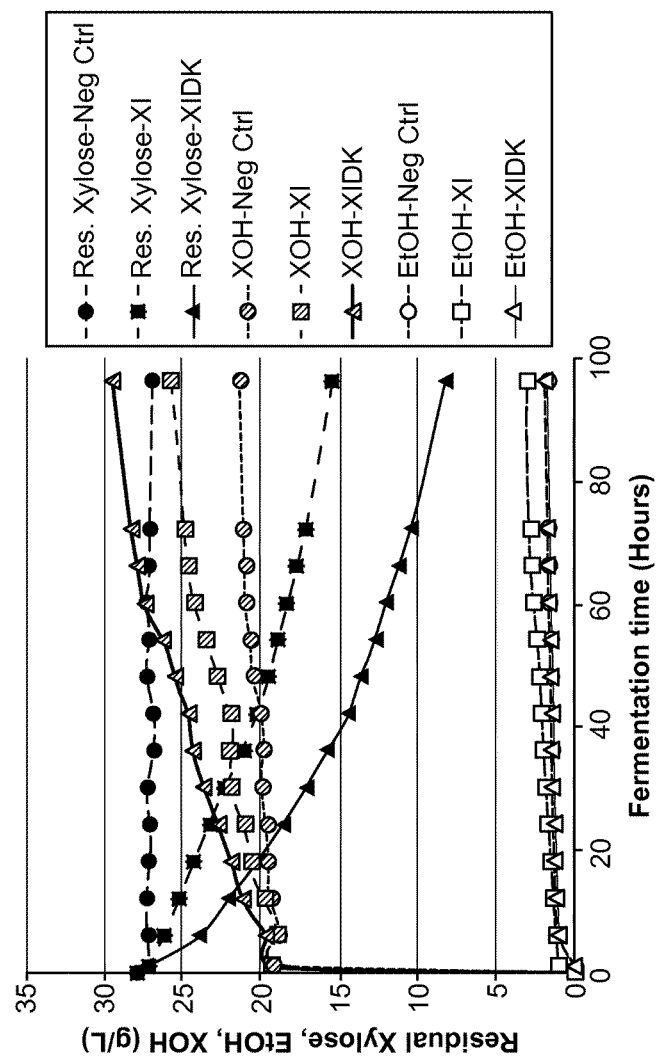
FIG. 5 provides a graph showing the time course analysis of 25-ml fermentation of haploid strains comprising an empty plasmid (negative control), XI-XD-XK pathway or XI gene only.
Figure 6:
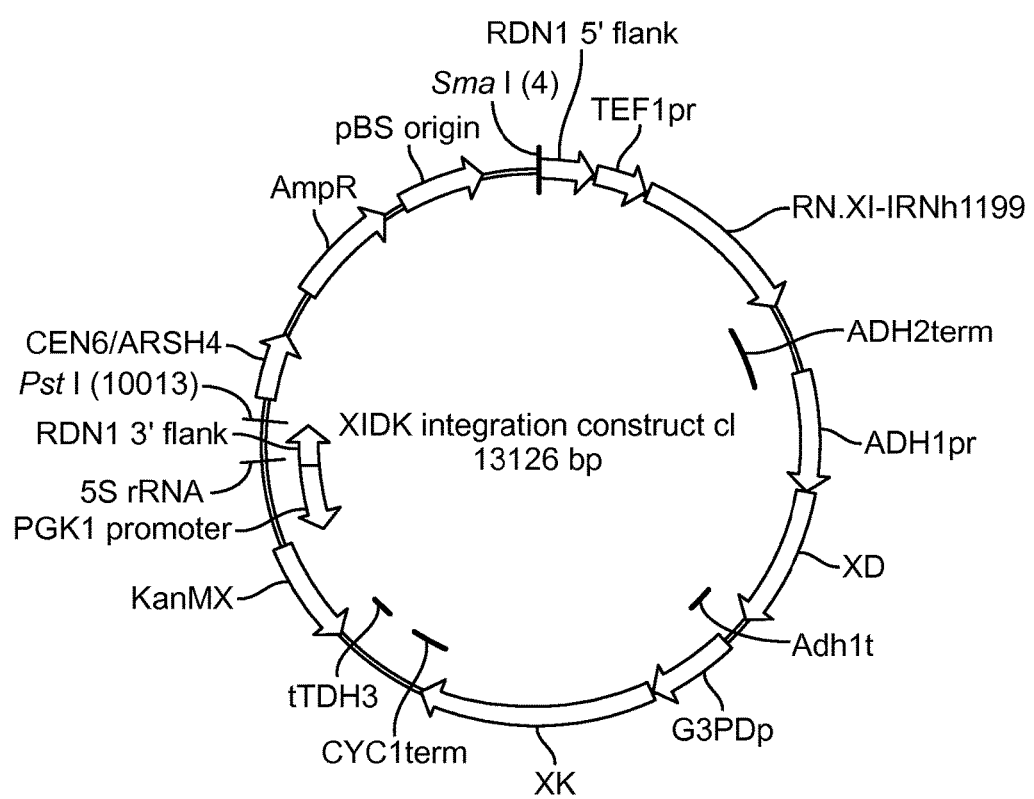
FIG. 6 provides a map of the XIDK integration construct.

FIG. 5 provides a time course analysis of 25 ml fermentation of haploid strains comprising the empty plasmid (i.e., the negative control), XI-XD-XK pathway, or XI gene only. Fermentation was performed in 25 ml scintillation vials in YPD5.5X3 (YPD medium containing 5.5% glucose and 3% xylose). Automated samples analysis demonstrated higher xylose consumption rate, higher ethanol (EtOH) production, and lower xylitol (XOH) production by strains comprising the XI-XD-XK pathway compared with strain comprising only the XI gene.

Example 3

Growth Rate Evaluation of XI-XD-XK Strains in Xylose Minimal Media

Strains NRRL-Y1528 and a Thermosacc®-derived haploid yeast strain comprising the XI-XD-XK pathway and control strains harboring only the XI gene were grown in defined mineral xylose medium in order to compare their specific growth rate on xylose. Samples were taken in order to measure the level of biomass and thus calculate the specific rate of growth.

Glycerol stocks containing the NRRL-Y1528 and Thermosacc®-derived haploid yeast strains prepared in Example 1 were inoculated into 5 ml of SD minimal medium containing 2% glucose. Cells were grown for 24 hours in an incubator at 30° C. with shaking at 250 rpm. After incubation, 0.5 mls of this culture were then diluted into 50 ml of SD minimal medium containing 2% xylose as the only carbon source in a 250 ml shake flask. The cultures were allowed to grow at 30° C. with shaking at 160 rpm. Samples from the culture were removed for optical density measurements at 600 nm once or twice per day. Once the optical density of the culture reached a value above 5 it was diluted 10-fold with minimal medium containing 2% xylose as the only carbon source. The process was continued for 150 hours. During this time, the XI-only strains did not grow significantly, whereas the XI-XD-XK strains grew at a growth rate of 0.08 to 0.09 $hr^{-1}$.

In order to calculate the specific growth rate, a plot of the natural log of biomass concentration versus time was used to generate a linear correlation. The slope of this correlation yielded the specific growth rate for the strain under the specified conditions.

| | Growth Rate $hr^{-1}$ | |
| --- | --- | --- |
| Genes | NRRL Y-1528 Strains | Thermosacc ®-Derived Haploid Strains |
| XI only | No growth | 0.01 |
| XI-XD-XK | 0.08 | 0.09 |
| Fold improvement over XI-only strain | N/A | 9 |

Example 4

XI-XD-XK Integration at rDNA Locus

Integration of the genes encoding the XI-XD-XK pathway at the rDNA locus allows for stable co-expression of pathway components in yeast without continuous selection for the plasmid. Plasmid PLS0047984 is constructed by subcloning 5' and 3' homologous sequences from the RDN 1 locus using standard yeast recombination cloning techniques. PLS0047984 is linearized by digestion with SmaI and PstI to generate a linear fragment suitable for integrative transformation of target strains. Following outgrowth, selection for frequent recombination events is carried out on YPD containing 200 ug/ml G418 selective plates. PCR on the emergent colonies is performed to verify the presence of the XI gene following transformation.

Example 5

Evaluation of XI Gene Diversity

Nine diverse copies of XI genes from eukaryotic origin were reconstructed from cDNA sequences or found in DNA sequences translated BLAT (See e.g., Kent, Genome Res. 12:656-664 [2002]) or BLAST searches. The sequences were harvested, codon optimized (in one case, the same gene was subjected to two alternate codon optimizations), synthesized with BamHI and Kozak sequences upstream of their start codons and an NdeI sequence downstream of their stop codons. Sequences were subcloned into the BamHI and NdeI sites of PLS030112, under the control of the *S. cerevisiae* TEF1 promoter. These plasmids were transformed into a yeast expression strain that does not encode any other exogenous genes for xylose utilization.

Colonies grown on YPD with 200 ug/ml G418 were picked after 48 hours of growth in five replicates into 96-well plate filled with 400 ul of (YPD containing 200 ug/ml G418, 1 mM MgSO4 and the trace elements solution provided above) and were grown for 24 hours at 30° C. and 85% relative humidity, in a incubator-shaker at 2" throw and shaking speed of 250 RPM. After incubation, 80 ul of the culture were used to inoculate 96-deep well plate filled with 320 ul of YP[5.5%]G amended with 200 ug/ml G418, 1 mM $MgSO_4$ and Trace elements solution. Strains were grown for an additional 24 hours under the same conditions. At the end of the propagation step, the plate was spun down (4000 RPM for ten minutes), and the cells were used to inoculate 400 ul of fermentation medium (YP[5.5%]G[3.0%]X amended with 200 ug/ml G418, 1 mM MgSO4 and Trace elements solution). The fermentation process was performed in capmat sealed 96-well plates at 30° C. degree and 85% relative humidity, in an incubator-shaker 2" throw and shaking speed of 100 RPM. At the end of 72 hours, the plate was spun down (4000 RPM for ten minutes) and the supernatant was analyzed for residual xylose in the supernatant by using a spectrophotometric assay (e.g., Megazyme xylose assay; CAT No. K-XYLOSE) performed according to the manufacturer's protocol. Improvement in xylose utilization was determined by comparing the performance of the XI-transformed strain with that of a control strain that was transformed with only the antibiotic marker and a background strain comprising only the original XI gene.

Figure 7:
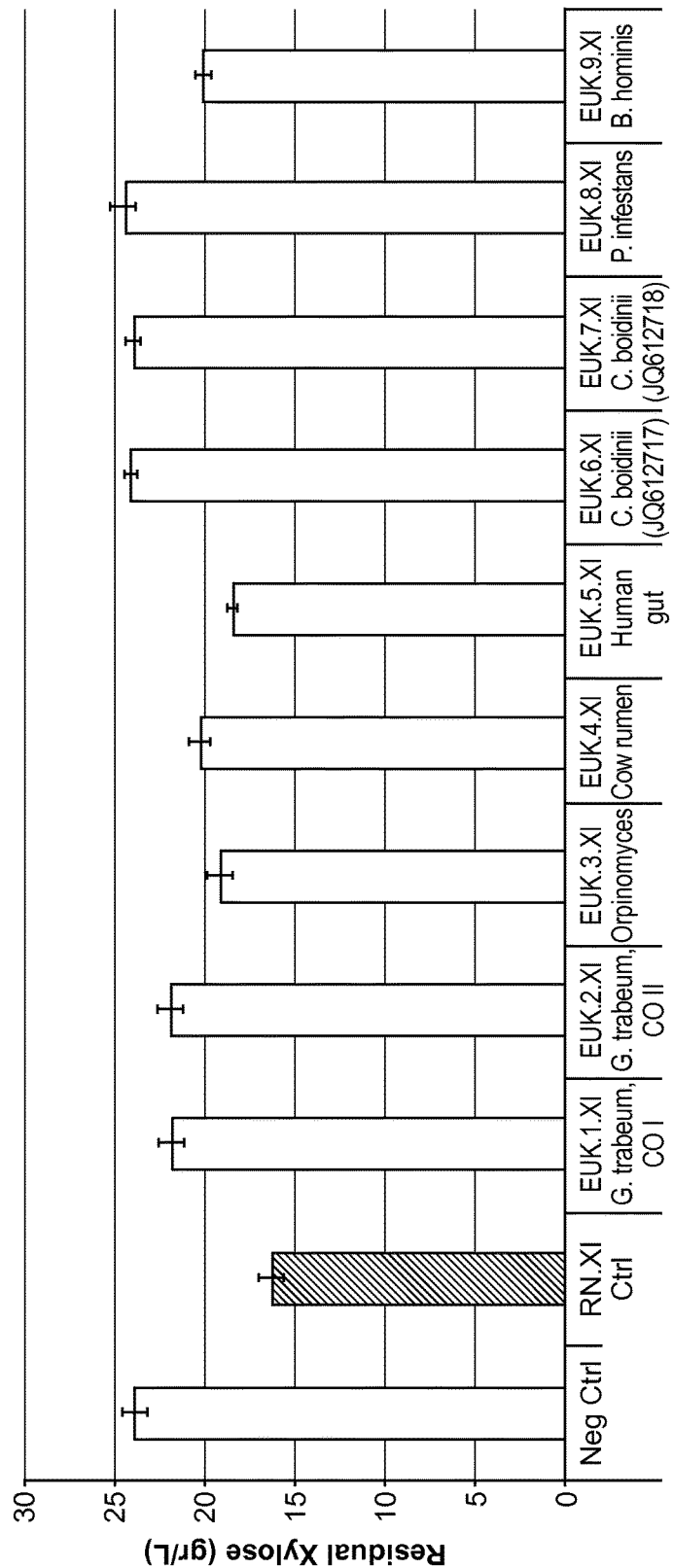
FIG. 7 provides a graph showing the residual xylose as measured after fermentation of NRRL Y1528-derived haploid strains comprising XI genes from diverse origins. Fermentation was performed in 96-well plates for 72 hours in YPD media supplemented with 30 g/l xylose (n=7, error bars±SD).

Four of the nine strains (i.e., comprising one of the new XI sequences) consumed significantly more xylose than the negative control. The best strains were EUK.3 (*Orpinomyces* XI), EUK.4 (XI obtained from cow rumen), EUK.5 (XI obtained from human gut), and EUK.9 (*B. hominis* XI). FIG. 7 provides a graph showing the residual xylose as measured after fermentation of the control and transformed NRRL Y1528-derived haploid strains described in Example 1.

While particular embodiments of the present invention have been illustrated and described, it will be apparent to those skilled in the art that various other changes and modifications can be made without departing from the spirit and scope of the present invention. Therefore, it is intended that the present invention encompass all such changes and modifications with the scope of the present invention.

The present invention has been described broadly and generically herein. Each of the narrower species and subgeneric groupings falling within the generic disclosure also form part(s) of the invention. The invention described herein suitably may be practiced in the absence of any element or elements, limitation or limitations which is/are not specifically disclosed herein. The terms and expressions which have been employed are used as terms of description and not of limitation. There is no intention that in the use of such terms and expressions, of excluding any equivalents of the features described and/or shown or portions thereof, but it is recognized that various modifications are possible within the scope of the claimed invention. Thus, it should be understood that although the present invention has been specifically disclosed by some preferred embodiments and optional features, modification and variation of the concepts herein disclosed may be utilized by those skilled in the art, and that such modifications and variations are considered to be within the scope of this invention.

We claim:

1. A recombinant fungal host cell comprising at least one nucleic acid construct, wherein said nucleic acid construct comprises one polynucleotide encoding a xylose isomerase of SEQ ID NO:2, and one polynucleotide encoding a xylitol dehydrogenase having at least 90% identity to SEQ ID NO:4, and one polynucleotide encoding a xylulokinase having at least 90% sequence identity to SEQ ID NO:6.

2. The recombinant fungal host cell of claim 1, wherein said xylose isomerase, xylitol dehydrogenase, and xylulokinase are eukaryotic or prokaryotic enzymes.

3. The recombinant fungal host cell of claim 1, wherein said nucleic acid construct further comprises at least one genetic element that facilitates stable integration into a fungal host genome.

4. The recombinant fungal host cell of claim 3, wherein said genetic element facilitates integration into a fungal host genome by homologous recombination.

5. The recombinant fungal host cell of claim 1, wherein at least one of said polynucleotide sequences is operatively linked to a promoter sequence that is functional in a said recombinant fungal host cell.

6. The recombinant fungal host cell of claim 1, wherein said polynucleotide sequence contains codons optimized for expression in a yeast cell.

7. The recombinant fungal host cell of claim 1, wherein the recombinant fungal host cell has had one or more native genes deleted from its genome.

8. The recombinant fungal host cell of claim 1, wherein the recombinant fungal host cell is altered to overexpress one or more polynucleotides.

9. The recombinant fungal host cell of claim 8, wherein overexpression results in one or more phenotypes selected from increased transport of xylose into the recombinant fungal host cell, increased xylulokinase activity, increased xylitol dehydrogenase activity, increased xylose isomerase activity, increased xylose reductase activity, increased flux through the pentose phosphate pathway, decreased sensitivity to catabolite repression, increased tolerance to ethanol, increased tolerance to acetate, increased tolerance to increased osmolarity, increased tolerance to low pH, and reduced product of by products, wherein comparison is made to the corresponding unaltered fungal host cell.

10. A recombinant fungal host cell of claim 1 comprising one nucleic acid construct, wherein said nucleic acid construct comprises at least one polynucleotide encoding a xylose isomerase of SEP ID NQ:2.

11. A method for producing a fermentation product, comprising:
(a) providing the recombinant fungal host cell of claim 1;
(b) providing a fermentation medium; and
(c) contacting said fermentation medium with said recombinant fungal host cell under conditions suitable for generating said fermentation product.

* * * * *